United States Patent [19]
Murai et al.

[11] Patent Number: 5,998,334
[45] Date of Patent: Dec. 7, 1999

[54] PYRAZOLE COMPOUNDS, PROCESSES FOR THEIR PRODUCTION AND HERBICIDES CONTAINING THEM

[75] Inventors: Shigeo Murai; Hiroshi Kikugawa; Hitoshi Nakayama; Makiko Sano; Akihiko Isogai, all of Kusatsu, Japan

[73] Assignee: Ishihara Sangyo Kaisha Ltd., Osaka, Japan

[21] Appl. No.: 09/147,191

[22] PCT Filed: Apr. 25, 1997

[86] PCT No.: PCT/JP97/01457

§ 371 Date: Oct. 26, 1998

§ 102(e) Date: Oct. 26, 1998

[87] PCT Pub. No.: WO97/41106

PCT Pub. Date: Nov. 6, 1997

[30] Foreign Application Priority Data

Apr. 26, 1996 [JP] Japan .................................. 8-130879
Aug. 9, 1996 [JP] Japan .................................. 8-227767

[51] Int. Cl.$^6$ ........................... A01N 43/56; C07D 231/20
[52] U.S. Cl. ................... 504/282; 546/276.1; 548/369.4
[58] Field of Search ...................... 548/369.4; 546/276.1; 504/286

[56] References Cited

U.S. PATENT DOCUMENTS 4,063,925 12/1977 Takuo et al. .
5,824,802 10/1998 Benko et al. ............................ 544/140

FOREIGN PATENT DOCUMENTS 2 002 375 2/1970 United Kingdom .
0 630 555 2/1995 WIPO .

OTHER PUBLICATIONS

T. Aono et al, "Preparation of pyrazole and peroxylipid formation inhibitors. lipoxygenase Inhibitors, and colagenase inhibitors containing them," Feb. 18, 1991, p. 690, Chemical Abstracts, Abstract No. 62091m, vol. 114, No. 7.

*Primary Examiner*—Robert W. Ramsuer
*Attorney, Agent, or Firm*—Oblon, Spivak, McClelland, Maier & Neustadt, P.C.

[57] ABSTRACT

A pyrazole compound of the formula (I) or its salt:

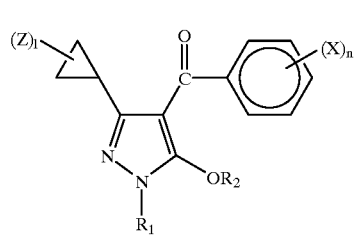

which is useful as a herbicide.

18 Claims, No Drawings

PYRAZOLE COMPOUNDS, PROCESSES FOR THEIR PRODUCTION AND HERBICIDES CONTAINING THEM

This application is a 371 of PCT/JP97/01437 filed Apr. 25, 1997.

TECHNICAL FIELD

The present invention relates to novel pyrazole compounds useful as active ingredients for herbicides.

1. Background Art

UK 2002375A and EP 282944A disclose pyrazole derivatives having various substituents at the 3-position of a pyrazole ring. However, the pyrazole compounds of the present invention are clearly distinguished from such derivatives in that they have a cycloalkyl group substituted at the 3-position of a pyrazole ring.

Further, EP 638555A discloses pyrazole glycolic acid amide derivatives having various substituents at the 3- and 4-positions of a pyrazole ring. However, the pyrazole compounds of the present invention are clearly distinguished from such derivatives in that they have a substituted benzoyl group substituted at the 4-position of a pyrazole ring.

2. Disclosure of the Invention

The present inventors have conducted various studies paying attention to pyrazole compounds to find out an excellent herbicide and as a result, have accomplished the present invention. Namely, the present invention provides novel pyrazole compounds of the formula (I) or their salts:

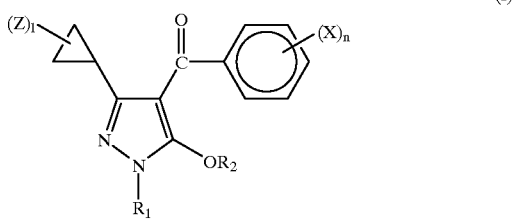

(I)

wherein $R_1$ is an alkyl group, $R_2$ is a hydrogen atom, a methyl group, —A—$R_3$, a phenyl group which may be substituted, a pyridyl group which may be substituted, or an allyl group which is substituted by a phenyl group, A is —$SO_2$—, —CO—, —CH($R_6$)— or —CH($R_7$)CO—, $R_3$ is an alkyl group which may be substituted, an alkenyl group which may be substituted, an alkynyl group which may be substituted, an alkoxy group which may be substituted, a cyano group, a dialkylamino group or a phenyl group which may be substituted, each of $R_6$ and $R_7$ is a hydrogen atom or an alkyl group, X is a hydrogen atom, a halogen atom, an alkyl group, a haloalkyl group, an alkoxy group, an alkylthio group, an alkylsulfinyl group, an alkylsulfonyl group, a nitro group, an alkoxycarbonyl group, —$SO_2N(R_8)R_9$, —$N(R_{10})SO_2R_{11}$, —$CH_2S(O)qR_{12}$ or —$OSO_2R_{13}$, each of $R_8$, $R_9$, $R_{10}$, $R_{11}$, $R_{12}$ and $R_{13}$ is an alkyl group, Z is an alkyl group, l is an integer of from 0 to 5, n is an integer of from 1 to 5, and q is an integer of from 0 to 2, provided that when l is at least 2, a plurality of Z may be the same or different, and when n is at least 2, a plurality of X may be the same or different; processes for their production; herbicides containing them; and novel intermediate compounds useful for producing them.

Now, the present invention will be described in detail with reference to the preferred embodiments.

The alkyl group or the alkyl moiety for $R_1$ and $R_3$ may be a $C_{1-10}$, preferably $C_{1-5}$, linear or branched alkyl group, and the alkyl group for $R_6$ and $R_7$ may be a $C_{1-2}$ alkyl group. The alkyl group or the alkyl moiety for $R_8$, $R_9$, $R_{10}$, $R_{11}$, $R_{12}$, $R_{13}$, X and Z may be a $C_{1-4}$ linear or branched alkyl group. Specific examples of such an alkyl group or moiety include methyl, ethyl, propyl, isopropyl, butyl, tert-butyl, pentyl, octyl and decyl. The alkenyl group for $R_3$ may be a $C_{2-10}$ linear or branched alkenyl group, such as vinyl, allyl, butadienyl or isopropenyl. The alkynyl group for $R_3$ may be a $C_{2-10}$ liner or branched alkynyl group, such as ethynyl, propynyl or 2-penten-4-ynyl.

The substituent for the phenyl group which may be substituted or the pyridyl group which may be substituted, for $R_2$, may be halogen, $C_{1-4}$ haloalkyl or nitro. The number of substituents may be one or more, and when the number is at least 2, a plurality of such substituents may be the same or different.

The substituent for the alkyl which may be substituted, the alkenyl which may be substituted, the alkynyl which may be substituted, or the alkoxy group which may be substituted, for $R_3$, may be halogen, $C_{1-4}$ alkoxy, $C_{1-6}$ alkoxycarbonyl or cyano. The number of substituents may be one or more, and if it is at least 2, a plurality of such substituents may be the same or different.

The substituent for the phenyl group which may be substituted, for $R_3$, may be halogen, $C_{1-4}$ alkyl, $C_{1-4}$ haloalkyl, $C_{1-4}$ alkoxy-$C_{1-4}$ alkyl, $C_{1-4}$ alkoxy, nitro or cyano. The number of substituents may be one or more, and if it is at least 2, a plurality of such substituents may be the same or different.

The halogen atom form X and the halogen as the substituent contained in $R_2$, $R_3$ and X, may be a fluorine atom, a chlorine atom, a bromine atom or an iodine atom. The number of halogen atoms as substituents, may be one or more, and if it is at least 2, a plurality of halogen atoms may be the same or different.

Among pyrazole compounds of the formula (I), a compound wherein $R_2$ is a hydrogen atom, is capable of forming a salt. The salt may be any salt so long as it is agriculturally acceptable, and it may, for example, be an alkali metal salt such as a sodium salt or a potassium salt, an alkaline earth metal salt such as a magnesium salt or a calcium salt, or an ammonium salt such as a dimethylamine salt or a triethylamine salt.

The pyrazole compounds of the formula (I) or their salts (hereinafter referred to as the compounds of the present invention) can be prepared in accordance with the following reactions (A) to (E) and conventional methods for producing salts.

(A) When $R_2$ is a hydrogen atom:

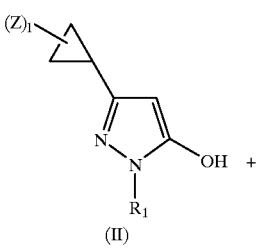

(II)

-continued

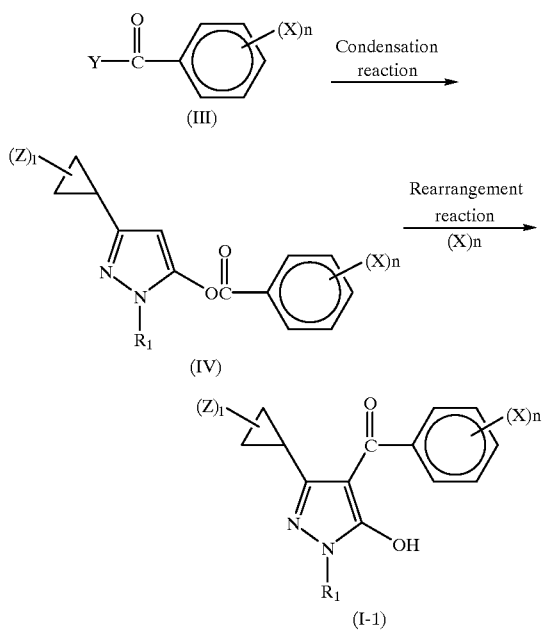

(B) When R₂ is a hydrogen atom:

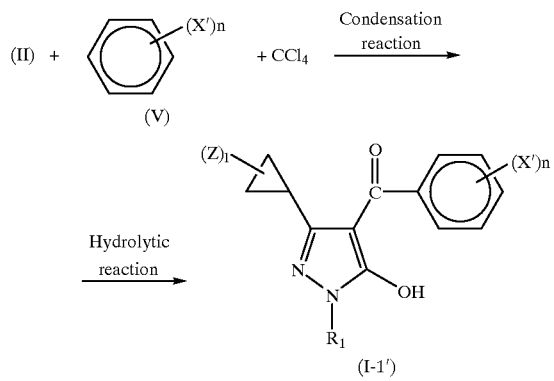

(C) When R₂ is a hydrogen atom:

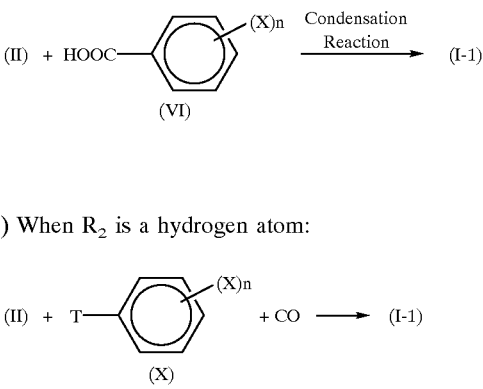

(D) When R₂ is a hydrogen atom:

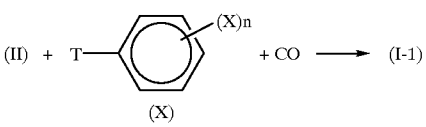

(E) When R₂ is other than a hydrogen atom:

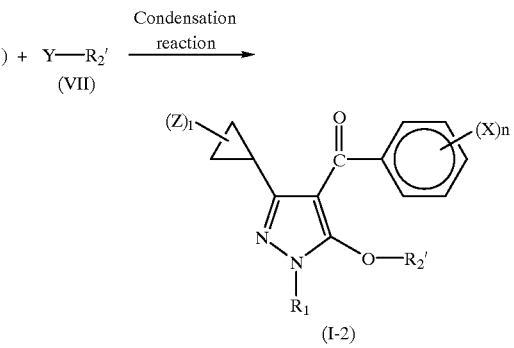

Among the compounds of the present invention, those having certain predetermined substituents can be prepared in accordance with the following reactions (F) to (G) and conventional methods for preparing salts.

(F) When R₂ is a hydrogen atom, and (X)n contains at least one alkylsulfinyl or alkylsulfonyl group:

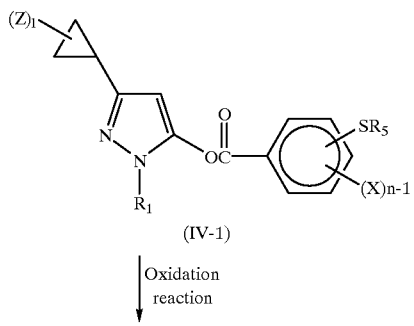

-continued

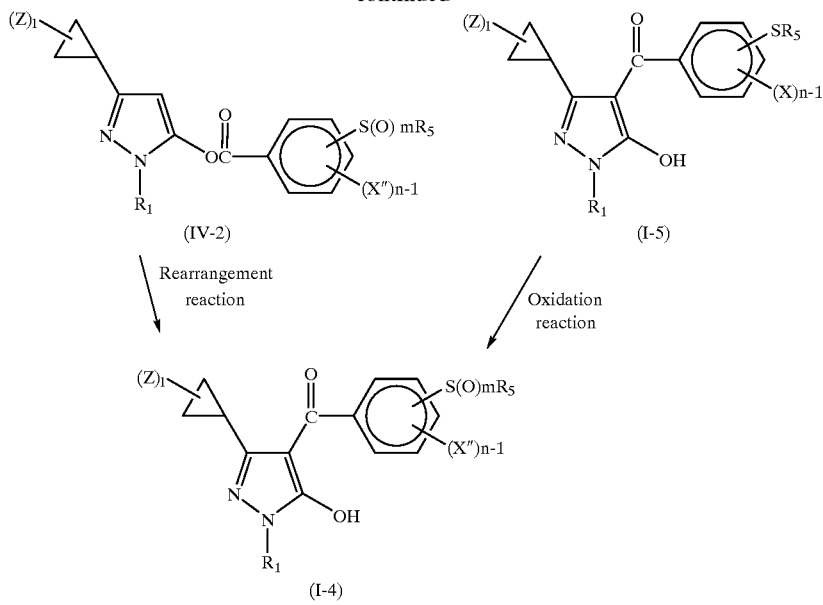

(G) When $R_2$ is other than a hydrogen atom, and $(X)n$ contains at least one alkylsulfinyl or alkylsulfonyl group:

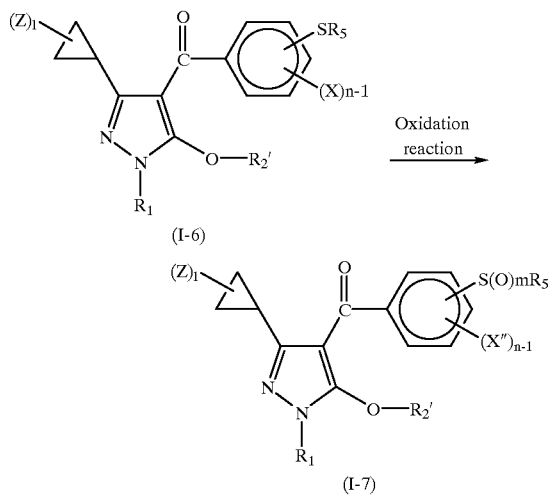

Now, the above reaction (A) will be described. In the reaction (A), $R_1$, X, Z, l and n are as defined above, and Y is a halogen atom.

The condensation reaction in the reaction (A) can be carried out, if necessary, in the presence of a base. As such a base, one or more members may be suitably selected for use from carbonates such as potassium carbonate and sodium carbonate; hydrogencarbonates such as potassium hydrogencarbonate and sodium hydrogencarbonate; metal hydrides such as potassium hydride and sodium hydride; amines such as monomethylamine, dimethylamine and triethylamine; and pyridines such as pyridine and 4-dimemthylaminopyridine.

Further, the condensation reaction in the reaction (A) can be carried out, if necessary, in the presence of a solvent. As such a solvent, any solvent may be used so long as it is a solvent inert to the reaction, and one or more members may be suitably selected for use from aromatic hydrocarbons such as benzene, toluene, xylene and chlorobenzene; cyclic or noncyclic aliphatic hydrocarbons such as carbon tetrachloride, methylene chloride, chloroform, dichloromethane, dichloroethane, trichloroethane, hexane and cyclohexane; ethers such as dioxane, tetrahydrofuran and diethyl ether; esters such as methyl acetate and ethyl acetate; polar aprotic solvents such as dimethylsulfoxide, sulfolane, dimethylacetamide, dimethylformamide, N-methylpyrrolidone, pyridine and hexamethylphosphoric triamide; nitriles such as acetonitrile, propionitrile and acrylonitrile; ketones such as acetone and methyl ethyl ketone; and water.

Further, the condensation reaction in the reaction (A) can be carried out, if necessary, in the presence of a phase transfer catalyst. As such a phase transfer catalyst, one or more members may be suitably selected for use from e.g. benzyltriethylammonium chloride, benzyltriethylammonium bromide, tetraethylammonium chloride and tetraethylammonium bromide.

The reaction temperature of the condensation reaction in the reaction (A) is usually from 0 to 250° C., preferably from 15 to 150° C., and the reaction time is usually from 0.1 to 48 hours, preferably from 0.1 to 24 hours.

The compound of the formula (IV) which can be produced by the condensation reaction in this reaction (A), is a novel intermediate compound useful for producing the compounds of the present invention.

The rearrangement reaction in the reaction (A) comprises the following two steps i.e. (1) a rearrangement reaction step and (2) a pH adjusting reaction step. The rearrangement reaction step is carried out usually in the presence of a base. As such a base, one or more members may be suitably selected for use from carbonates such as potassium carbonate and sodium carbonate; and calcium hydroxide. The base is used usually in an amount of from 0.5 to 5 mols per mol of the compound of the formula (IV).

Further, the rearrangement reaction step of the rearrangement reaction in the reaction (A) can be carried out, if necessary, in the presence of a solvent. As such a solvent, any solvent may be used so long as it is a solvent inert to the reaction, and one or more members may suitably be selected for use from aromatic hydrocarbons such as benzene, toluene, xylene and chlorobenzene; ethers such as dioxane, tetrahydrofuran and diethyl ether; and polar aprotic solvents such as dimethylsulfoxide, sulfolane, dimethylacetamide, dimethylforamide, N-methylpyrrolidone, pyridine and hexamethylphosphoric triamide.

The rearrangement reaction step of the rearrangement reaction in the reaction (A) is preferably carried out under an azeotropic dehydrating condition, whereby the rearrangement reaction will effectively proceed. This is one of preferred embodiments of the present invention. By the rearrangement reaction step, a salt of the compound of the formula (I) is produced, and a method for producing such a salt is also one of embodiments of the present invention. Further, a compound of the above-mentioned formula (I-2) can be produced by reacting a salt of the compound of the above formula (I) or a reaction mixture containing such a salt, obtained by this rearrangement reaction step, with a compound of the above formula (VII), under the reaction conditions for the reaction (D) which will be described hereinafter. This is also one of embodiments of the present invention.

The reaction temperature in the rearrangement reaction step is usually from 50 to 250° C., preferably from 50 to 150° C., and the reaction time is usually from 0.1 to 48 hours, preferably from 0.5 to 24 hours.

The pH adjusting reaction step of the rearrangement reaction in the reaction (A) is a reaction to adjust the pH value to at most 7, which is carried out usually in the presence of an acidic substance and water. As such an acidic substance, one or more members may suitably be selected for use from inorganic acids such as hydrochloric acid and sulfuric acid; and organic acids such as acetic acid.

The pH adjusting reaction step of the rearrangement reaction in the reaction (A) can be carried out, if necessary, in the presence of a solvent. As such a solvent, any solvent may be used so long as it is a solvent inert to the reaction. For example, one or more members may be suitably selected for use from those mentioned in the description of the rearrangement reaction step as the preceding step.

The pH adjusting reaction step of the rearrangement reaction in the reaction (A) may be carried out after isolating the reaction product obtained by the rearrangement reaction step as the preceding step, in accordance with a conventional method, or may be carried out in one pot by using the reaction mixture obtained by the rearrangement reaction step, as it is. When it is carried out in one pot, it is carried out by adding and reacting an acidic substance and water to the reaction mixture obtained by the rearrangement reaction step as the preceding step.

The reaction temperature for the pH adjusting reaction step is usually from 0 to 100° C., preferably from 0 to 60° C.

Now, the above-mentioned reaction (B) will be described. In the reaction (B), $R_1$, Z, l, n and (II) are as defined above, and X' is a hydrogen atom, a halogen atom, an alkyl group, a haloalkyl group, an alkoxy group, an alkylthio group, an alkylsulfinyl group or an alkylsulfonyl group, provided that when n is at least 2, a plurality of X' may be the same or different.

The condensation reaction in the reaction (B) is carried out usually in the presence of a Lewis acid. As such a Lewis acid, one or more members may suitably be selected for use from e.g. dry aluminum chloride and dry aluminum bromide.

Further, the condensation reaction in the reaction (B) can be carried out, if necessary, in the presence of a solvent. As such a solvent, any solvent may be used so long as it is a solvent inert to the reaction, and one or more members may suitably be selected for use from halogenated aliphatic hydrocarbons such as carbon tetrachloride, methylene chloride, chloroform, dichloromethane, and dichloroethane.

The reaction temperature for the condensation reaction in the reaction (B) is usually from 0 to 80° C., and the reaction time is usually from 0.1 to 24 hours, preferably from 0.1 to 10 hours.

The hydrolytic reaction in the reaction (B) is carried out usually in the presence of an acidic substance. As such an acidic substance, one or more members may suitably be selected for use from e.g. inorganic acids such as hydrochloric acid and sulfuric acid.

The hydrolytic reaction in the reaction (B) can be carried out, if necessary, in the presence of a solvent. As such a solvent, any solvent may be used so long as it is a solvent inert to the reaction, and one or more members may suitably be selected for use among those exemplified in the description of the condensation reaction as the preceding reaction.

The hydrolytic reacction in the reaction (B) may be carried out after isolating the reaction product obtained by the condensation reaction as the preceding reaction, in accordance with a conventional method, or may be carried out in one pot using the reaction mixture obtained by the condensation reaction as it is. In the case where it is carried out in one pot, post treatment such as removal of the Lewis acid may be applied, if necessary, to the reaction mixture obtained by the condensation reaction as the preceding reaction, and the acidic substance and water are added thereto to carry out the reaction.

The reaction temperature for the hydrolytic reaction in the reaction (B) is usually from 20 to 100° C., and the reaction time is usually from 0.1 to 24 hours, preferably from 0.1 to 10 hours.

Now, the above-mentioned reaction (C) will be described. In the reaction (C), X, n, (II) and (I-1) are as defined above.

The condensation reaction in the reaction (C) is carried out usually in the presence of a condensing agent and a solvent. As such a condensing agent, N,N'-dicyclohexylcarbodiimide may, for example, be mentioned, and as such a solvent, any solvent may be used so long as it is a solvent inert to the reaction, and one or more members may suitably be selected for use among alcohols such as tert-butyl alcohol and tert-amyl alcohol.

The condensation reaction in the reaction (C) can be carried out, if necessary, in the presence of a base. As such a base, one or more members may suitably be selected for use from e.g. carbonates such as potassium carbonate and sodium carbonate.

The reaction temperature for the condensation reaction in the reaction (C) is usually from 50 to 100° C., and the reaction time is usually from 0.1 to 24 hours, preferably from 0.5 to 20 hours.

Now, the above-mentioned reaction (D) will be described. In the reaction (D), X, n, (II) and (I-1) are as defined above, and T is a chlorine atom, a bromine atom or an iodine atom.

The reaction (D) is carried out usually in the presence of a base and a metal catalyst. As a base, one or more members may suitably be selected for use from e.g. alkali metals such as sodium and potassium; alkali metal alkolates such as sodium methylate, sodium ethylate and potassium tert-butylate; carbonates such as potassium carbonate and sodium carbonate; hydrogencarbonates such as potassium hydrogencarbonate and sodium hydrogencarbonate; metal hydroxides such as potassium hydroxide and sodium hydroxide; metal hydrides such as potassium hydride and sodium hydride; amines such as monomethylamine, dimethylamine and triethylamine; pyridines such as pyridine and 4-dimethylaminopyridine; and N,N-dimethylaniline. As the metal catalyst, a transition metal such as palladium, rhodium, ruthenium or platinum, may be mentioned. The ligand used against the metal of the metal catalyst is not particularly limited, but an organophosphine compound such as triphenylphosphine or tri-n-butylphosphine is preferred.

The reaction (D) may be carried out, if necessary, in the presence of a solvent. As such a solvent, any solvent may be used so long as it is a solvent inert to the reaction. For example, one or more members may suitably be selected for use among aromatic hydrocarbons such as benzene, toluene, xylene and chlorobenzene; cyclic or noncyclic aliphatic hydrocarbons such as carbon tetrachloride, methylene chloride, chloroform, dichloromethane, dichloroethane, trichloroethane, hexane and cyclohexane; ethers such as dioxane, tetrahydrofuran and diethyl ether; esters such as methyl acetate and ethyl acetate; polar aprotic solvents such as dimethylsulfoxide, sulfolane, dimethylacetamide, dimethylformamide, N-methylpyrrolidone and pyridine; nitriles such as acetonitrile, propionitrile and acrylonitrile; ketones such as acetone and methyl ethyl ketone; amines such as monomethylamine, dimethylamine and triethylamine; alcohols such as methanol, ethanol, propanol, and tert-butanol; organic acids such as acetic acid and propionic acid; aqueous ammonia; and water.

The reaction temperature for the reaction (D) is usually from 30 to 300° C., preferably from 50 to 200° C., and the reaction time is usually from 0.1 to 48 hours, preferably from 1 to 24 hours.

Now, the above-mentioned reaction (E) will be described. In the reaction (E), $R_1$, X, Y, Z, l, n and (I-1) are as defined above, and $R_2'$ is a methyl group, —A—$R_3$, a phenyl group which may be substituted, a pyridyl group which may be substituted or an allyl group which is substituted by a phenyl group (where A and $R_3$ are as defined above).

The condensation reaction in the reaction (E) may be carried out, if necessary, in the presence of a base. As such a base, one or more members may suitably be selected for use from carbonates such as potassium carbonate and sodium carbonate; hydrogencarbonates such as potassium hydrogencarbonate and sodium hydrogencarbonate; metal hydroxides such as potassium hydroxide and sodium hydroxide; metal hydrides such as potassium hydride and sodium hydride; amines such a monomethylamine, dimethylamine and triethylamine; and pyridines such as pyridine and 4-dimethylaminopyridine.

The condensation reaction in the reaction (E) may be carried out, if necessary, in the presence of a solvent. As such a solvent, any solvent may be used so long as it is inert to the reaction. For example, one or more members may suitably be selected for use from aromatic hydrocarbons such as benzene, toluene, xylene and chlorobenzene; cyclic or noncyclic aliphatic hydrocarbons such as carbon tetrachloride, methylene chloride, chloroform, dichloromethane, dichloroethane, trichloroethane, hexane and cyclohexane; ethers such as dioxane, tetrahydrofuran and diethyl ether; esters such as methyl acetate and ethyl acetate; polar aprotic solvents such as dimethylsulfoxide, sulfolane, dimethylacetamide, dimethylformamide, N-methylpyrrolidone, pyridine and hexamethylphosphoric triamide; nitriles such as acetonitrile, propionitrile and acrylonitrile; ketones such as acetone and methyl ethyl ketone; and water.

The condensation reaction in the reaction (E) may be carried out, if necessary, in the presence of a phase transfer catalyst and/or potassium iodide. As such a phase transfer catalyst, one or more members may suitably be selected for use among those mentioned for the condensation reaction in the above-mentioned reaction (A).

The reaction temperature for the condensation reaction in the reaction (E) is usually from 0 to 200° C., preferably from 15 to 150° C., and the reaction time is usually from 0.1 to 48 hours, preferably from 0.1 to 24 hours.

Now, the above-mentioned reaction (F) will be described. In the reaction (F), $R_1$, X, Z, l and n are as defined above, $R_5$ is an alkyl group, preferably a $C_{1-4}$ alkyl group, X" is a hydrogen atom, a halogen atom, an alkyl group, a haloalkyl group, an alkoxy group, an alkylsulfinyl group, an alkylsulfonyl group, a nitro group, an alkoxycarbonyl group, —$SO_2N(R_8)R_9$, —$N(R_{10})SO_2R_{11}$, —$CH_2S(O)_{q'}R_{12}$ or —$OSO_2R_{13}$, wherein $R_8$, $R_9$, $R_{10}$, $R_{11}$, $R_{12}$ and $R_{13}$ are as defined above, m is 1 or 2, and q' is 1 or 2. In the reaction (F), the oxidation reaction for producing (IV-2) from (IV-1) and the oxidation reaction for producing (I-4) from (I-5) (hereinafter referred to simply as the oxidation reaction) are carried out usually in the presence of an oxidizing agent and a solvent. As such an oxidizing agent, one or more members may suitably be selected for use from e.g. m-chloroperbenzoic acid and hydrogen peroxide. As the solvent, any solvent may be used so long as it is a solvent inert to the reaction. For example, one or more members may suitably be selected for use among those mentioned for the condensation reaction in the above-mentioned reaction (B).

The reaction temperature for the oxidation reaction in the reaction (F) is usually from 0 to 80° C., and the reaction time is usually from 0.1 to 48 hours, preferably from 0.1 to 24 hours.

The rearrangement reaction in the reaction (F) can be carried out in accordance with the rearrangement reaction in the above-mentioned reaction (A).

Now, the above-mentioned reaction (G) will be described. In the reaction (G), $R_1$, $R_2'$, $R_5$, X, X", Z, l, m and n are as defined above.

The oxidation reaction in the reaction (G) can be carried out in accordance with the oxidation reaction in the above-mentioned reaction (F).

The compound of the formula (II) in the above reactions (A), (B), (C) and (D) is a novel intermediate compound which is useful for producing the compounds of the present invention and may be produced, for example, by a method such as the reaction (H).

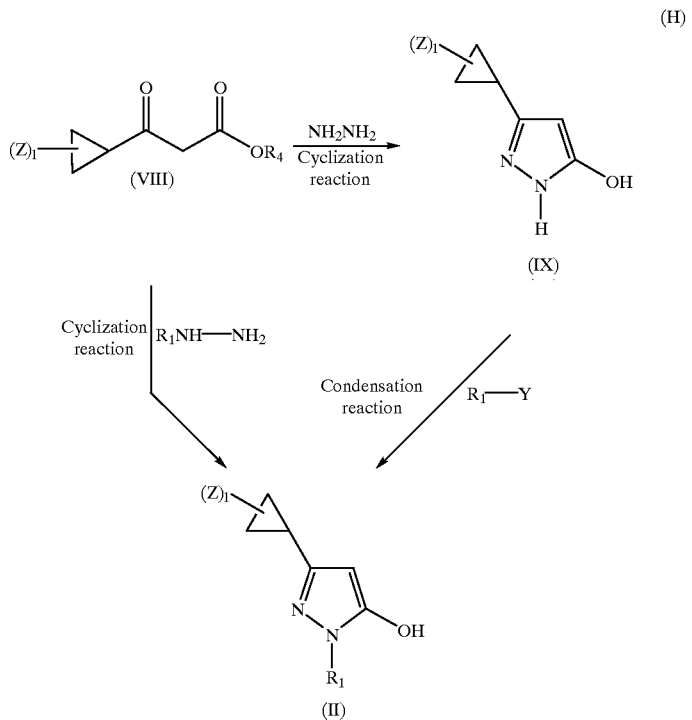

Now, the reaction (H) will be described. In the reaction (H), $R_1$, Y, Z and l are as defined above, and $R_4$ is a $C_{1-6}$ alkyl group.

In the reaction (H), the cyclization reaction for producing (II) from (VIII) and the cyclization reaction for producing (IX) from (VIII) (hereinafter referred to simply as the cyclization reaction) may be carried out, if necessary, in the presence of a solvent. As such a solvent, any solvent may be used so lone as it is a solvent inert to the reaction. For example, one or more members may suitably be selected for use from aromatic hydrocarbons such as benzene, toluene, xylene and chlorobenzene; cyclic or noncyclic aliphatic hydrocarbons such as carbon tetrachloride, methylene chloride, chloroform, dichloromethane, dichloroethane, trichloroethane, hexane and cyclohexane; ethers such as dioxane, tetrahydrofuran and diethyl ether; polar aprotic solvents such as dimethylsulfoxide, sulfolane, dimethylacetamide, dimethylformamide, N-methylpyrrolidone pyridine and hexamethylphosphoric triamide; nitriles such as acetonitrile, propionitrile and acrylonitrile; and water.

The cyclization reaction in the reaction (H) may be carried out, if necessary, under an azeotropic dehydration condition.

The reaction temperature for the cyclization reaction in the reaction (H) is usually from 0 to 200° C., preferably from 20 to 150° C., and the reaction time is usually from 0.1 to 48 hours, preferably from 0.1 to 24 hours.

The condensation reaction in the reaction (H) is carried out usually in the presence of a base and a solvent. As the base, one or more members may suitably be selected for use from carbonates such as potassium carbonate and sodium carbonate; and metal hydrides such as potassium hydride and sodium hydride. Particularly preferred is potassium carbonate.

As the solvent, any solvent may be used so long as it is a solvent inert to the reaction. For example, one or more members may suitably be selected for use from ethers such as dioxane, tetrahydrofuran and diethyl ether; and polar aprotic solvents such as dimethylsulfoxide, sulfolane, dimethylacetamide, dimethylformamide, N-methylpyrrolidone, pyridine and hexamethylphosphoric triamide. Particularly preferred is hexamethylphosphoric triamide.

The reaction temperature for the condensation reaction in the reaction (H) is usually from −20 to +150° C., preferably from −15 to +60° C., and the reaction time is usually from 0.1 to 24 hours, preferably from 0.1 to 10 hours.

The compound of the formula (IX) which can be prepared by the cyclization reaction in this reaction (H), is a novel intermediate compound which is useful for producing the compounds of the present invention.

The compounds of the present invention and the intermediate compounds useful for the production thereof, have the following isomers. Such various isomers (the respective isomers and mixtures of such isomers) are within the scope of the present invention.

(1) Among the compounds of the present invention represented by the above formula (I), compounds wherein $R_2$ is a hydrogen atom, and intermediate compounds represented by the above formulas (II) and (IX), have the following tautomers, respectively.

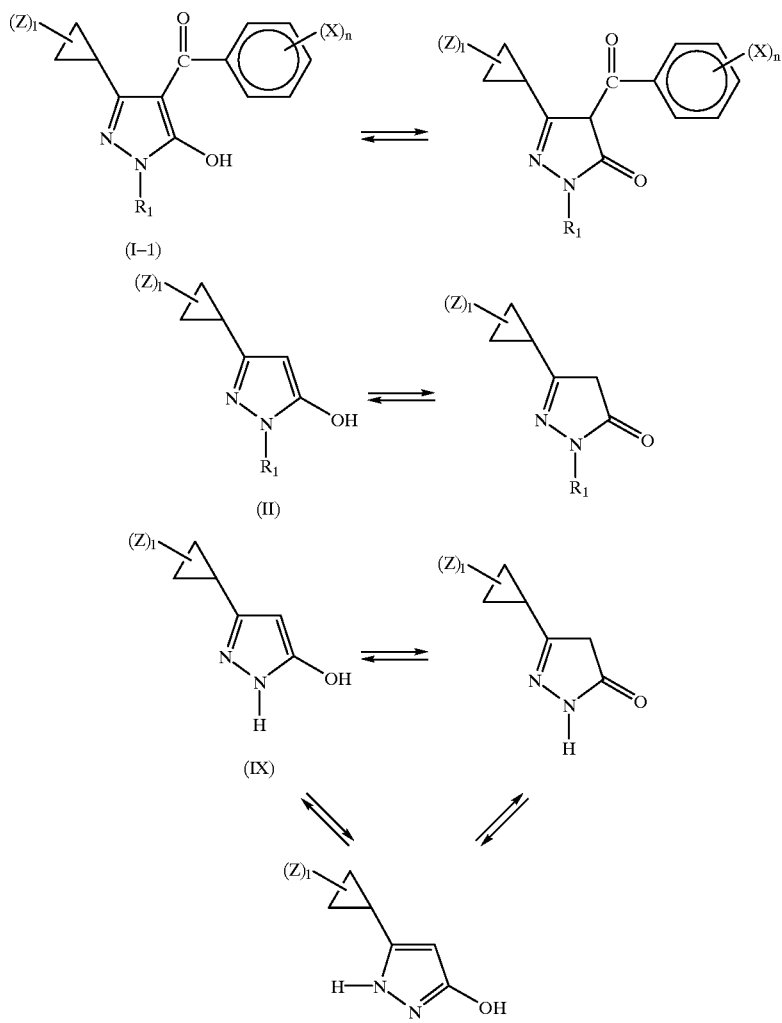

wherein $R_1$, X, Z, l and n are as defined above.

(2) Among the compounds of the present invention represented by the above formula (I) and the intermediate compounds represented by the above formulas (II), (IV), (VIII) and (IX), compounds wherein l is at least 1, have optical isomers. Some examples will be given below, but it should be understood that the optical isomers in the present invention are not limited to such specific examples.

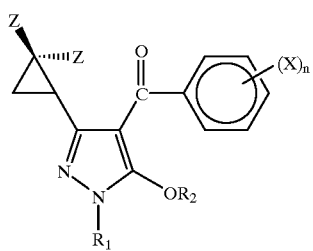

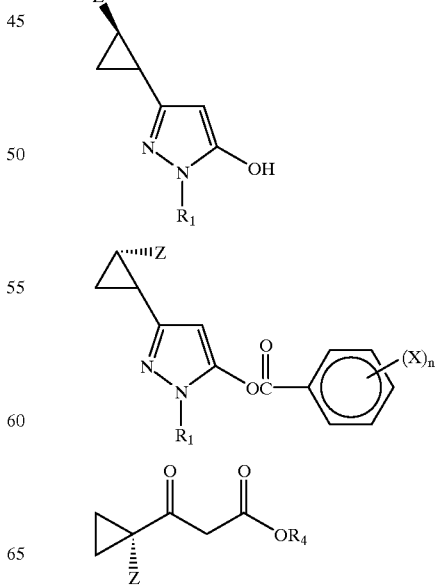

-continued

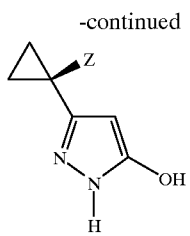

wherein R₁, R₂, R₄, X, Z and n are as defined above.

In the specification of this application, such optical isomers are meant for a mixture of isomers (racemic modification) unless otherwise specified.

(3) Among compounds of the present invention represented by the above formula (I), compounds wherein $R_2$ is —A—$R_3$, and $R_3$ is an alkenyl group which may be substituted, have geometrical isomers (E-isomer and Z-isomer).

The compound of the present invention exhibits excellent herbicidal effects when used as an active ingredient of a herbicide. It finds a wide range of application to crop lands such as paddy fields, upland farms, orchards and mulberry fields, and non-crop lands such as forests, farm roads, playgrounds, and factory sites. The application method may suitably be selected from soil treatment application and foliar application.

The herbicidal composition containing the compound of the present invention is capable of controlling noxious weeds including grasses (or gramineae) such as barnyardgrass (*Echinochloa crus-galli* L.), crabgrass (*Digitaria sanguinalis* L.), greenfoxtail (*Setaria viridis* L.), goosegrass (*Eleusine indica* L.), wild oat (*Avena fatua* L.), johnsongrass (*Sorghum halepense* L.), quackgrass (*Agropyron repens* L.), alexandergrass (*Brachiaria plantaginea*), paragrass (*Panicum purpurascens*), sprangletop (*Leptochloa chinensis*) and red sprangletop (*Leptochloa panicea*); edges (or Cyperaceae) such as rice flatsedge (*Cyperus iria* L.), purple nutsedge (*Cyperus rotundus* L.), japanese bulrush (*Scirpus juncoides*), flatsedge (*Cyperus serotinus*), smallflower umbrellaplant (*Cyperus difformis*), slender spikerush (*Eleocharis acicularis*), and water chestnut (*Eleocharis kuroguwai*); alismataceae such as japanese ribbon wapato (*Sagittaria pygmaea*), arrow-head (*Sagittaria trifolia*) and narrowleaf waterplantain (*Alisma canaliculatum*); pontederiaceae such as monochoria (*Monochoria vaginalis*) and monochoria species (*Monochoria korsakowii*); scrophulariaceae such as false pimpernel (*Lindernia pyxidaria*) and abunome (*Dopatrium junceum*); lythraceae such as toothcup (*Rotala indica*) and red stem (*Ammannia multiflora*); and broadleaves such as velvetleaf (*Abutilon theophrasti* MEDIC.), tall morningglory (*Ipomoea purpurea* L.), common lambsquarters (*Chenopodium album* L.), prickly sida (*Sida spinosa* L.), common purslane (*Portulaca oleracea* L.), slender amaranth (*Amaranthus viridis* L.), redroot pigweed (*Amaranthus retroflexus* L.), sicklepod (*Cassia obtusifolia* L.), black nightshade (*Solanum nigrum* L.), pale smartweed (*Polygonum lapathifolium* L.), common chickweed (*Stellaria media* L.), common cocklebur (*Xanthium strumarium* L.), flexuous bittercress (*Cardamine flexuosa* WITH.), henbit (*Lamium amplexicaule* L.) and threeseeded copperleaf (*Acalypha australis* L.).

Accordingly, it is useful for controlling noxious weeds non-selectively or selectively in the cultivation of a crop plant such as corn (*Zea mays* L.), soybean (*Glycine max* Merr.), cotton (Gossypium spp.), wheat (Triticum spp.), rice (*Oryza sativa* L.), barley (*Hordeum vulgare* L.), oat (*Avena sativa* L.), sorgo (*Sorghum bicolor* Moench), rape (*Brassica napus* L.), sunflower (*Helianthus annuus* L.), sugar beet (*Beta vulgaris* L.), sugar cane (*Saccharum officinarum* L.), japanese lawngrass (*Zoysia japonica stend*), peanut (*Arachis hypogaea* L.) or flax (*Linum usitatissimum* L.) The compound of the present invention is particularly effective for selectively controlling noxious weeds in the cultivation of corn, wheat or rice, especially in the cultivation of corn.

The herbicidal composition containing the compound of the present invention is usually formulated by mixing the compound with various agricultural adjuvants and used in the form of a formulation such as a dust, granules, water-dispersible granules, a wettable powder, an emulsifiable concentrate, a water-based suspension concentrate, an oil-based suspension concentrate, water soluble granules (or powder), tablets or capsules. However, so long as it is suitable for the purpose of the present invention, it may be formulated into any type of formulation which is commonly used in this field.

Such agricultural adjuvants include solid carriers such as diatomaceous earth, slaked lime, calcium carbonate, talc, white carbon, kaoline, bentonite, a mixture of kaolinite and sericite, clay, sodium carbonate, sodium bicarbonate, mirabilite, zeolite and starch; solvents such as water, toluene, xylene, solvent naphtha, dioxane, acetone, isophorone, methyl isobutyl ketone, chlorobenzene, cyclohexane, dimethylsulfoxide, dimethylformamide, N-methyl-2-pyrrolidone, and alcohol; anionic surfactants and spreaders such as a salt of fatty acid, a benzoate, an alkylsulfosuccinate, a dialkylsulfosuccinate, a polycarboxylate, a salt of alkylsulfuric acid ester, an alkyl sulfate, an alkylaryl sulfate, an alkyl diglycol ether sulfate, a salt of alcohol sulfuric acid ester, an alkyl sulfonate, an alkylaryl sulfonate, an aryl sulfonate, a lignin sulfonate, an alkyldiphenyl ether disulfonate, a polystyrene sulfonate, a salt of alkylphosphoric acid ester, an alkylaryl phosphate, a styrylaryl phosphate, a salt of polyoxyethylene alkyl ether sulfuric acid ester, a polyoxyethylene alkylaryl ether sulfate, a salt of polyoxyethylene alkyl ether sulfuric acid ester, a polyoxyethylene alkylaryl ether sulfuric acid ester, a polyoxyethylene alkyl ether phosphate, a salt of polyoxyethylene alkyl aryl phosphoric acid ester, and a salt of a condensate of naphthalene sulfonate with formalin; nonionic surfactants and spreaders such as a sorbitan fatty acid ester, a glycerin fatty acid ester, a fatty acid polyglyceride, a fatty acid alcohol polyglycol ether, acetylene glycol, acetylene alcohol, an oxyalkylene block polymer, a polyoxyethylene alkyl ether, a polyoxyethylene alkylaryl ether, a polyoxyethylene styrylaryl ether, a polyoxyethylene glycol alkyl ether, a polyoxyethylene fatty acid ester, a polyoxyethylene sorbitan fatty acid ester, a polyoxyethylene glycerin fatty acid ester, a polyoxyethylene hydrogenated castor oil, and a polyoxypropylene fatty acid ester; and vegetable and mineral oils such as olive oil, kapok oil, castor oil, palm oil, camellia oil, coconut oil, sesame oil, corn oil, rice bran oil, peanut oil, cottonseed oil, soybean oil, rapeseed oil, linseed oil, tung oil, and liquid paraffins. Such adjuvants may be selected for use among those known in this field, so long as the purpose of the present invention can thereby be accomplished. Further , various additives which are commonly used, such as a filler, a thickener, an anti-settling agent, an anti-freezing agent, a dispersion stabilizer, a phytotoxicity reducing agent, and an anti-mold agent, may also be employed.

The weight ratio of the compound of the present invention to the various agricultural adjuvants is usually from 0.1:99.9 to 95:5. preferably from 0.2:99.8 to 85:15.

The dose of the herbicidal composition of the present invention can not generally be defined, since it may vary depending upon the weather condition, the soil condition, the type of formulation, the types of the weeds to be controlled, the season for the application, etc. However, it is usually applied so that the compound of the present invention would be applied in an amount of from 0.5 to 5000 g/ha, preferably from 1 to 1000 g/ha, more preferably from 5 to 500 g/ha. The present invention covers such a method for controlling noxious weeds by application of such a herbicidal composition.

The herbicidal compositions of the present invention may be used in admixture with or in combination with other agricultural chemicals, fertilizers or phytotoxicity-reducing agents. In such a case, they may exhibit even better effects or activities. As other agricultural chemicals, herbicides, fungicides, antibiotics, plant hormones or insecticides may, for example, be mentioned. Especially with a mixed herbicidal composition having the compound of the present invention used in admixture with or in combination with one or more active ingredients of other herbicides, it is possible to improve the herbicidal activities, the season for the application and the range of applicable weed types. Further, the compound of the present invention and an active ingredient of other herbicide may be separately formulated, so that they may be mixed for use at the time of application, or both may be formulated together. The present invention covers such mixed herbicidal compositions.

The blend ratio of the compounds of the present invention with the active ingredients of other herbicides can not generally be defined, since it varies depending upon the weather condition, the soil condition, the type of the formulation, the season for the application, the manner of the application, etc. However, one active ingredient of other herbicide may be incorporated usually in an amount of from 0.001 to 10000 parts by weight, preferably from 0.01 to 1000 parts by weight, per part by weight of the compound of the present invention. Further, the total dose of all of the active ingredients is usually from 0.1 to 10000 g/ha, preferably from 0.2 to 5000 g/ha. The present invention covers a method for controlling noxious weeds by application of such herbicidal compositions.

As the active ingredients of other herbicides, the following (common names) may be mentioned.

(1) Those which are believed to exhibit herbicidal effects by disturbing auxin activities of plants, including a phenoxy acetic acid type such as 2,4-D, MCPA, MCPB or naproanilide, an aromatic carboxylic acid type such as 2,3,6-TBA, dicamba, picloram or clopyralid, and others such as benazolin, quinclorac, quinmerac or diflufenzopyr.

(2) Those which are believed to exhibit herbicidal effects by inhibiting photosynthesis of plants, including a urea type such as diuron, linuron, isoproturon or metobenzuron, triazine type such as simazine, atrazine, atratone, simetryn, prometryn, dimethametryn, metribuzin, terbuthylazine, cyanazine or ametryn, an uracil type such as bromacil or lenacil, an anilide type such as propanil or cypromid, a carbamate type such as swep or phenmedipham, a hydroxybenzonitrile type such as bromoxynil, bromoxynil-octanoate or ioxynil, and others such as pyridate or bentazon.

(3) A quaternary ammonium salt type such as paraquat or diquat, which is believed to be converted to free radicals by itself to form active oxygen in the plant body and thus to exhibit quick herbicidal effects.

(4) Those which are believed to exhibit herbicidal effects by inhibiting chlorophyllbiosynthesis of plants and abnormally accumulating a photosensitizing peroxide substance in the plant body, including a diphenyl ether type such as nitrofen, chlomethoxyfen, bifenox, acifluorfen-sodium, fomesafen or oxyfluorfen, a cyclic imide type such as chlorphthalim, flumioxadine, flumiclorac-pentyl, methyl [2-chloro-4-fluoro-5-(5,6,7,8-tetrahydro-3-oxo-1H,3H-[1,3,4] thiadiazolo[3,4-a]pyridazin-1-ylideneamino)phenylthio] acetate (compound disclosed at page 60 of proceedings of 19th Meeting of Pesticide Science Society of Japan), and others such as oxadiation, sulfentrazone, carfentrazone-ethyl, thidiazimin, ethyl 2 -chloro-5-(4-chloro-5-difluoromethoxyl-1-methylpyrazol-3-yl)-4-fluorophenoxyacetate (compound disclosed at pages 70–71 of proceedings of 21th Meeting of Pesticide Science Society of Japan).

(5) Those which are believed to exhibit herbicidal effects characterized by whitening activities by inhibiting chromogenesis of plants such as carotenoids, including a pyridazinone type such as norflurazon or metflurazon, a pyrazole type such as pyrazolate, pyrazoxyfen or benzofenap, and others such as fluridone, flurtamone, diflufenican, methoxyphenone, clomazone, sulcotrione, 2-(2'-nitro-4'-methylsulfonyl-benzoyl)-1,3-cyclohexanedione (compound disclosed in U.S. Pat. No. 5,506,195), isoxaflutole or difenzoquat.

(6) Those which exhibit herbicidal effects specifically to gramineous plants, including an aryloxyphenoxypropionic acid type such as diclofop-methyl, pyriphenop-sodium, fluazifop-butyl, haloxyfop-methyl, quizalofop-ethyl or cyhalofop-butyl, and a cyclohexanedione type such as alloxydim-sodium, clethodim, sethoxydim or tralkoxydim.

(7) Those which are believed to exhibit herbicidal effects by inhibiting an amino acid biosynthesis of plants, including a sulfonylurea type such as chlorimuron-ethyl, sulfometuron-methyl, primisulfuron-methyl, bensulfuron-methyl, chlorsulfuron, metsulfuron-methyl, cinosulfuron, pyrazosulfuron-ethyl, azimsulfuron, flazasulfuron, rimusulfuron, nicosulfuron, imazosulfuron, cyclosulfamuron, prosulfuron, flupyrsulfuron, trisulfuron-methyl, halosulfuron-methyl or thifensulfuron-methyl, a triazolopyrimidinesulfoneamide type such as flumetsulam or metosulam, an imidazolinone type such as imazapyr, imazethapyr, imazaquin, imazamox or imazameth or imazamethabenz, a pyrimidinylsalicylic acid type such as pyrithiobac-sodium, bispyribac-sodium or pyriminobac-methyl, and others such as glyphosate-ammonium, glyphosate-isopropylamine, glufosinate-ammonium or bialaphos.

(8) Those which are believed to exhibit herbicidal effects by inhibiting cell mitoses of plants, including a dinitroaniline type such as trifluralin, oryzalin, nitralin or pendimethalin, an organic phosphorus type such as amiprofos-methyl, butamifos, anilofos or piperophos, a phenylcarbamate type such as chlorpropham or barban, a cumylamine type such as daimuron, cumyluron or bromobutide, and others such as asulam or dithiopyr.

(9) Those which are believed to exhibit herbicidal effects by inhibiting protein biosynthesis or lipid biosynthesis of plants, including a thiocarbamate type such as EPTC, butylate, molinate, dimepiperate, esprocarb, thiobencarb or pyributicarb, or chloroacetamide type such as alachlor, butachlor, pretilachlor, metolachlor, thenylchlor, dimethenamid, acetochlor or propachlor, and other compounds such as a ethobenzanide, mefenacet, thiafluamide, tridiphane, cafenstrole, 4-(2-chlorophenyl)-N-cyclohexyl-4, 5-dihydro-N-ethyl-5-oxo-1H-tetrazol-1-carboxyamide (compound disclosed in JP-A-6-306061), oxaziclomefon, or 2-ethyl-2-[2-(3-chlorophenyl)-2,3-epoxypropyl]-indan-1,3-dione (compound disclosed in JP-A-2-304043).

As is evident from Test Examples 1 and 2 given hereinafter, the compound of the present invention include those which show selectivity for effectively controlling weeds, while showing safety to crop plants such as rice, wheat and corn. When the compound of the present invention is to be used in the cultivation of such crop plants, synergistic effects may be obtained by using it in admixture with or in combination with one or more of the following compounds among the above-mentioned active compounds of other herbicides.

In the cultivation of rice:

2,4-D, MCPA, MCPB, naproanilide, quinclorac, simetryn, prometryn, dimethametryn, propanil, swep, bentazon, nitrofene, chlomethoxyfen, bifenox, oxadiazon, pyrazolate, pyrazoxyfen, benzofenap, methoxyphenone, cyhalofop-butyl, bensulfuron-methyl, cinosulfuron, pyrazosulfuron-ethyl, azimsulfuron, imazosulfuron, cyclosulfamuron, bispyribac-sodium salt, pyriminobac-methyl, anilofos, piperophos, daimuron, cumyluron, bromobutide, dithiopyr, molinate, dimepiperate, esprocarb, thiobencarb, pyributicarb, thenylchlor, pretilachlor, butachlor, ethobenzanide, mefenacet, cafenstrole, 4-(2-chlorophenyl)-N-cyclohexyl-4,5-dihydro-N-ethyl-5-oxo-1H-tetrazole-1-carboxyamide, oxaziclomefon, and 2-ethyl-2-[2-(3-chlorophenyl)-2,3-epoxypropyl]-indane-1,3-dione.

In the cultivation of corn:

2,4-D, MCPA, dicamba, clopyralid, benazolin, diflufenzopyr, diuron, linuron, metobenzuron, simazine, atrazine, atratone, metribuzin, terbuthylazine, cyanazine, ametryn, cypromid, bromoxynil, bromoxynil-octanoate, pyridate, bentazon, paraquat, oxyfluorfen, flumiclorac-pentyl, methyl [2-chloro-4-fluoro-5-(5,6,7,8-tetrahydro-3-oxo-1H,3H-[1,3,4]thiadiazolo[3,4-a]pyridazin-1-ylideneamino)phenylthio] acetate, fluridone, sulcotrione, 2-(2'-nitro-4'-methylsulfonylbenzoyl)-1,3-cyclohexanedione, isoxaflutole, carfentrazone ethyl, primisulfuron methyl, rimusulfuron, nicosulfuron, prosulfuron, halosulfuron-methyl, thifensulfuron-methyl, flumetsulam, metosulam, imazethapyr, glyphosate-ammonium salt, glyphosate-isopropyl amine salt, glufosinate-ammonium salt, trifluralin, pendimethalin, EPTC, butylate, alachlor, metolachlor, acetochlor, propachlor, dimethenamid and tridiphane.

In the cultivation on wheat:

MCPB, quinmerac, linuron, isoproturon, prometryn, bromoxynil, bromoxynil-octanoate, pyridate, bifenox, carfentrazone-ethyl, thidiazimin, ethyl 2-chloro-5-(4-chloro-5-difluoromethoxyl-1-methylpyrazol-3-yl)-4-fluorophenoxy acetate, flurtamone, diflufenican, sulcotrione, diclofop-methyl, tralkoxydim, chlorsulfuron, metsulfuron-methyl, prosulfuron, halosulfuron-methyl, flumetsulam, metosulam, pendimethalin, barban and imazamethabenz.

Now, preferred embodiments of the present invention will be described.

(1) The pyrazole compound of the above formula (I) or its salts.

(2) The pyrazole compound or its salt according to Item 1, wherein the formula (I) is represented by the formula (I'):

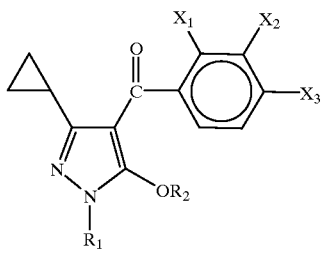

where $R_1$ is an alkyl group, $R_2$ is a hydrogen atom or —A—$R_3$, A is —$SO_2$—, —CO—, —$CH_2$— or —$CH_2CO$—, $R_3$ is an alkyl group which may be substituted, an alkenyl group which may be substituted, an alkynyl group which may be substituted, a cyano group or a phenyl group which may be substituted, each of $X^1$, $X^2$ and $X^3$ is a hydrogen atom, a halogen atom, an alkyl group, a haloalkyl group, an alkoxy group, an alkylthio group, an alkylsulfinyl group, an alkylsulfonyl group, a nitro group, —$SO_2N(R_8)R_9$, —$N(R_{10})SO_2R_{11}$, —$CH_2S(O)qR_{12}$ or —$OSO_2R_{13}$, each of $R_8$, $R_9$, $R_{10}$, $R_{11}$, $R_{12}$ and $R_{13}$ is an alkyl group, and q is an integer of from 0 to 2.

(3) The pyrazole compound or its salt according to Item 2, wherein A is —$SO_2$—, —$CH_2$— or —$CH_2CO$—, each of $X^1$, $X^2$ and $X^3$ is a hydrogen atom, a halogen atom, an alkyl group, a haloalkyl group, an alkoxy group, an alkylthio group, an alkylsulfinyl group, an alkylsulfonyl group or a nitro group.

(4) The pyrazole compound or its salt according to Item 3, where $X^1$ is an alkylthio group, an alkylsulfinyl group or an alkylsulfonyl group, and each of $X^2$ and $X^3$ is a hydrogen atom, a halogen atom, an alkyl group, a haloalkyl group or a nitro group.

(5) A herbicide containing the pyrazole compound or its salt as defined in Item 1, 2, 3 or 4, as an active ingredient.

(6) A method for controlling noxious weeds, which comprises applying an effective amount of the pyrazole compound or its salt as defined in Item 1, 2, 3, or 4.

(7) A method for controlling noxious weeds, which comprises applying an effective amount of the pyrazole compound or its salt as defined in Item 1, 2, 3, or 4 to an upland field.

(8) A method for controlling noxious weeds, which comprises applying an effective amount of the pyrazole compound or its salt as defined in Item 1, 2, 3, or 4 to a corn field.

(9) A method for controlling noxious weeds, which comprises applying an effective amount of the pyrazole compound or its salt as defined in Item 1, 2, 3, or 4 to a wheat field.

(10) A method for controlling noxious weeds, which comprises applying an effective amount of the pyrazole compound or its salt as defined in Item 1, 2, 3, or 4 to a paddy field.

(11) A mixed herbicidal composition comprising at least one member selected from the pyrazole compound or its salt as defined in Item 1, 2, 3, or 4 and at least one member selected from active ingredient compounds of other herbicides.

(12) The compound of the above formula (II).
(13) The compound according to Item 12, where l is 0.
(14) The compound of the above formula (IV).
(15) The compound according to Item 14, wherein l is 0.
(16) The compound according to Item 14, wherein the formula (IV) is represented by the formula (IV):

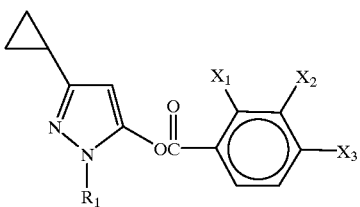

(IV')

wherein $R_1$ is an alkyl group, each of $X^1$, $X^2$ and $X^3$ is a hydrogen atom, a halogen atom, an alkyl group, a haloalkyl group, an alkoxy group, an alkylthio group, an alkylsulfinyl group, an alkylsulfonyl group, a nitro group, $-SO_2N(R_8)R_9$, $-N(R_{10})SO_2R_{11}$, $-CH_2S(O)qR_{12}$ or $-OSO_2R_{13}$, each of $R_8$, $R_9$, $R_{10}$, $R_{11}$, $R_{12}$ and $R_{13}$ is an alkyl group, and 1 is an integer of from 0 to 2.

(17) The pyrazole compound or its salt according to Item 16, wherein each of $X^1$, $X^2$ and $X^3$ is a hydrogen atom, a halogen atom, an alkyl group, a haloalkyl group, an alkoxy group, an alkylthio group, an alkylsulfinyl group, an alkylsulfonyl group or a nitro group.

(18) The pyrazole compound or its salt according to Item 17, wherein $X^1$ is an alkylthio group, an alkylsulfinyl group or an alkylsulfonyl group, and each of $X^2$ and $X^3$ is a hydrogen atom, a halogen atom, an alkyl group, a haloalkyl group or a nitro group.

BEST MODE FOR CARRYING OF THE INVENTION

Now, the present invention will be described in further detail with reference to Examples. However, it should be understood that the present invention is by no means restricted to such specific Examples. Firstly, Preparation Examples for the compounds of the present invention will be described.

PREPARATION EXAMPLE 1

Preparation of 3-cyclopropyl-4-(4-trifluoromethyl-2-methylsulfonylbenzoyl)-5-hydroxy-1-methylpyrazole (after-mentioned Compound No. a-11) and 3-cyclopropyl-4-(4-trifluoromethyl-2-methylsulfonylbenzoyl)-1-methyl-5-pyrazolyl p-toluene sulfonate (after-mentioned Compound No. a-12) (First method)

1) 1.4 g of methylhydrazine was added at room temperature to a solution having 5.53 g of tert-butyl 3-cylocopropyl-3-oxopropionate dissolved in 30 ml of tetrahydrofuran, and the mixture was reacted for about 2 hours under reflux.

After completion of the reaction, tetrahydrofuran was distilled off under reduced pressure to obtain 4.14 g of crude 3-cyclopropyl-5-hydroxy-1-methylpyrazole (after-mentioned Intermediate No. 1a-1).

The melting point of this product was from 95 to 121° C., and the NMR spectrum data are as follows.

$^1$H-NMR δppm [Solvent: CDCl$_3$] 0.76–0.8 (m,2H), 0.9–0.99 (m,2H), 1.74–1.81 (m,1H), 3.06 (s), 3.26 (s,3H), 4.6 (bs)

2) A solution having 0.41 g of sodium carbonate dissolved in 30 ml of water, was added to a solution having 1 g of 3-cyclopropyl-5-hydroxy-1-methylpyrazole obtained in the preceding step dissolved in 30 ml of toluene, followed by stirring for 5 minutes. Then, 4-trifluoromethyl-2-methylthiobenzoyl chloride preliminarily prepared by mixing and reacting under reflux for one hour, 1.52 g of 4-trifluoromethyl-2-methylthiobenzoic acid, 5 ml of thionyl chloride and a catalytic amount of N,N-dimethylformamide, followed by removal of excess thionyl chloride, was added thereto, and the mixture was reacted at 50° C. for one hour.

After completion of the reaction, the reaction mixture was cooled and put into water, and extracted with ethyl acetate. The obtained ethyl acetate layer was washed with a saturated sodium chloride aqueous solution and then dried over anhydrous sodium sulfate, and the solvent was distilled off under reduced pressure. The obtained residue was purified by silica gel column chromatography to obtain 0.8 g of oily 3-cyclopropyl-1-methyl-5-pyrazolyl 4-trifluoromethyl-2-methylthiobenzoate (after-mentioned Intermediate No. 2a-16). The NMR spectrum data of the product are as follows.

$^1$H-NMR δppm [Solvent: CDCl$_3$] 0.69–0.73 (m,2H), 0.86–0.91 (m,2H), 1.85–1.92 (m,1H), 2.53 (s,3H), 3.70 (s,3H), 5.94 (s,1H), 7.46 (d,1H), 7.53 (s,1H), 8.24 (d,1H)

3) 0.91 g of methachloroperbenzoic acid was dividedly added at room temperature to a solution having 0.75 g of 3-cyclopropyl-1-methyl-5-pyrazolyl 4-trifluoromethyl-2-methylthiobenzoate obtained in the preceding step dissolved in 30 ml of methylene chloride, and the mixture was reacted for one hour within a range of from room temperature to 40° C.

After completion of the reaction, the reaction mixture was put into water and extracted with methylene chloride.

The obtained methylene chloride layer was washed with dilute alkali and then with water, and thereafter dried over anhydrous sodium sulfate, and methylene chloride was distilled off. The obtained residue was purified by silica gel column chromatography to obtain 0.75 g of 3-cyclopropyl-1-methyl-5-pyrazolyl 4-trifluoromethyl-2-methylsulfonylbenzoate (after-mentioned Intermediate No. 2a-5) having a melting point of from 99 to 102° C. The NMR spectrum data of the product are as follows.

$^1$H-NMR δppm [Solvent: CDCl$_3$] 0.73–0.77 (m,2H), 0.86–0.94 (m,2H), 1.87–1.93 (m,1H), 2.05 (s,3H), 3.74 (s,3H), 5.95 (s,1H), 8.0 (d,1H), 8.06 (d,1H), 8.47 (s,1H)

4) A mixture comprising 0.7 g of 3-cyclopropyl-1-methyl-5-pyrazolyl-4-trifluoromethyl-2-methylsulfonylbenzoate obtained in the preceding step, 0.3 g of dry potassium carbonate, 25 ml of toluene and 5 ml of N,N-dimethylformamide, was reacted for one hour under an azeotropic dehydration condition using a Dean-Stark azeotropic dehydration apparatus.

After completion of the reaction, the reaction mixture was cooled and put into water, and the aqueous layer was washed with ethyl acetate. The aqueous layer was acidified with concentrated hydrochloric acid and extracted with ethyl acetate. The obtained ethyl acetate layer was washed with a saturated sodium chloride aqueous solution and dried over anhydrous sodium sulfate. Then, ethyl acetate was distilled off under reduced pressure to obtain the desired product 3-cyclopropyl-4-(4-trifluoromethyl-2-methylsulfonylbenzoyl)-5-hydroxy-1-methylpyrazole (after-mentioned Compound No. a-11) as a viscous crude product. The NMR spectrum data of this product are as follows.

$^1$H-NMR δppm [Solvent: CDCl$_3$] 0.42–0.45 (m,2H), 0.72–0.81 (m,2H), 0.95–1.05 (m,1H), 3.34 (s, 3H), 3.67 (s,3H), 7.73 (d,1H), 8.0 (d,1H), 8.4 (s,1H)

The melting point of 3-cyclopropyl-4-(4-trifluoromethyl-2-methylsulfonylbenzoyl)-5-hydroxy-1-methylpyrazole as the above-mentioned viscous crude product, was from 83 to 93° C.

5) 0.155 g of p-toluene sulfonyl chloride was added to a mixture comprising 0.3 g of 3-cyclopropyl-4-(4- trifluoromethyl-2-methylsulfonylbenzoyl)-5-hydroxy-1-methylpyrazole obtained in the preceding step, 0.118 g of dry potassium carbonate, 0.002 g of tetraethyl ammonium bromide, 20 ml of toluene and 5 ml of N,N-dimethylformamide, and the mixture was reacted for about one hour within a range of from 40 to 50° C. with stirring.

After completion of the reaction, the reaction mixture was put into water and extracted with ethyl acetate. The obtained ethyl acetate layer was washed with water and further with a saturated sodium chloride aqueous solution and then dried over anhydrous sodium sulfate, and ethyl acetate was distilled off under reduced pressure. The obtained residue was purified by silica gel column chromatography to obtain 0.3 g of 3-cyclopropyl-4-(4-trifluoromethyl-2-methylsulfonylbenzoyl)-1-methyl-5-pyrazolyl p-toluene sulfonate (after-mentioned Compound No. a-12) as a viscous desired product. The NMR spectrum data of this product are as follows.

$^1$H-NMR δppm [Solvent: CDCl$_3$] 0.52–0.56 (m,2H), 0.8–0.84 (m,2H), 1.48–1.55 (m,1H), 2.47 (s,3H), 3.32 (s,3H), 3.65 (s,3H), 7.37 (d,2H), 7.58 (d,1H), 7.82 (d,2H), 7.89 (d,1H), 8.28 (s,1H)

The melting point of the above viscous 3-cyclopropyl-4-(4-trifluoromethyl-2-methylsulfonylbenzoyl)-1-methyl-5-pyrazolyl p-toluene sulfonate was from 67 to 70° C.

PREPARATION EXAMPLE 2

Preparation of 3-cyclopropyl-4-(4-trifluoromethyl-2-methylsulfonylbenzoyl)-5-hydroxy-1-methylpyrazole (after-mentioned Compound No. a-11) and 3-cyclopropyl-4-(4-trifluoromethyl-2-methylsulfonylbenzoyl)-1-methyl-5-pyrazolyl p-toluene sulfonate (after-mentioned compound No. a-12) (Second method)

1) A mixture comprising 3.88 g of 3-cyclopropyl-1-methyl-5-pyrazolyl 4-trifluoromethyl-2-methylsulfonylbenzoate (after-mentioned Intermediate No. 2a-5), 1.52 g of dry potassium carbonate, 100 ml of toluene and 20 ml of N,N-dimethylformamide, was reacted for one hour under an azeotropic dehydration condition using a Dean-Stark azeotropic dehydration apparatus.

After completion of the reaction, the reaction mixture was cooled and put into water, followed by liquid separation. The obtained aqueous layer was acidified with concentrated hydrochloric acid and extracted with ethyl acetate. The obtained ethyl acetate layer was washed with water and then with a saturated sodium sulfate. Then, ethyl acetate was distilled off under chloride aqueous solution and dried over anhydrous sodium sulfate. Then, ethyl acetate was distilled off under reduced pressure to obtain 3.88 g of viscous 3-cyclopropyl-4-(4-trifluoromethyl-2-methylsulfonylbenzoyl)-5-hydroxy-1-methylpyrazole as a crude product. This product was left to stand to sufficiently remove the solvent to obtain crystals of 3-cyclopropyl-4-(4-trifluoromethyl-2-methylsulfonylbenzoyl)-5-hydroxy-1-methylpyrazole (after-mentioned Compound No. a-11) as the desired product, having a melting point of from 153 to 157° C.

2) 0.36 g of p-toluene sulfonyl chloride was added to a mixture comprising 0.7 g of crystals of 3-cyclopropyl-4-(4-trifluoromethyl-2-methylsulfonylbenzoyl)-5-hydroxy-1-methylpyrazole obtained in the preceding step, 0.27 g of dry potassium carbonate, 0.005 g of tetraethylammonium bromide, 20 ml of toluene and 4 ml of N,N-dimethylformamide, and the mixture was reacted for about 1.5 hours within a range of from 40 to 50° C. with stirring.

After completion of the reaction, the reaction mixture was put into water and extracted with ethyl acetate. The obtained ethyl acetate layer was washed with a saturated sodium chloride aqueous solution and dried over anhydrous sodium sulfate. Then, ethyl acetate was distilled off under reduced pressure. The obtained residue was purified by silica gel column chromatography to obtain 0.7 g of crystals of 3-cyclopropyl-4-(4-trifluoromethyl-2-methylsulfonylbenzoyl)-1-methyl-5-pyrazolyl p-toluene sulfonate (after-mentioned Compound No. a-12) as the desired product, having a melting point of from 135 to 138° C.

PREPARATION EXAMPLE 3

Preparation of 3-cyclopropyl-4-(2,4-dichloro-3-methylbenzoyl)-5-hydroxy-1-methylpyrazole (after-mentioned Compound No. a-8)

1) 2.76 g of 3-cyclopropyl-5-hydroxy-1-methylpyrazole (after-mentioned Intermediate No. 1a-1) and 3.9 g of 2,6-dichlorotoluene were charged into 30 ml of 1,2-dichloroethane, and 6.7 g of dry aluminum chloride was dividedly added thereto at a temperature of not higher than 50° C. with stirring. After the addition, stirring was continued for from 10 to 15 minutes within a range of from 35 to 40° C. Then, a solution having 4.0 g of carbon tetrachloride dissolved in 4 ml of 1,2-dichloroethane, was dropwise added thereto at the same temperature. After completion of the dropwise addition, the mixture was reacted for 1.5 hours at a temperature of from 40 to 45° C.

After completion of the reaction, the reaction mixture was put into 150 ml of ice water to separate a 1,2-dichloroethane layer.

2) 0.5 ml of water was added thereto, and the mixture was heated to 50° C., whereupon 3.5 ml of concentrated sulfuric acid was gradually dropwise added thereto. After completion of the dropwise addition, the mixture was reacted for 1.5 hours under reflux.

After completion of the reaction, the reaction mixture was left to cool, and 150 ml of water was added thereto, followed liquid separation. The obtained 1,2-dichloroethane layer was washed with water and then extracted with an alkaline solution having 3.5 g of sodium hydroxide dissolved in 100 ml of water. Then, 50% sulfuric acid was added thereto to make the liquid weakly acidic and extracted with methylene chloride. The obtained methylene chloride layer was dried over anhydrous sodium sulfate, and methylene chloride was distilled off under reduced pressure to obtain 3.5 g of the desired product having a melting point of from 112 to 115° C. The NMR spectrum data of this product are as follows.

$^1$H-NMR δppm [Solvent: CDCl$_3$] 0.66–0.71 (m,2H), 0.93–0.99 (m,2H), 1.15–1.22 (m,1H), 2.72 (s,3H), 3.89 (s,3H), 7.34 (d,1H), 7.57 (d,1H)

PREPARATION EXAMPLE 4

Preparation of 4-(2,4-dichlorobenzoyl)-3-cyclopropyl-1-ethyl-5-hydroxypyrazole (after-mentioned Compound No. a-18)

1) A solution having 0.87 g of dry hydrazine dissolved in 5 ml of dry tetrahydrofuran, was added to a solution having 5 g of tert-butyl 3-cyclopropyl-3-oxopropionate dissolved in 30 ml of dry tetrahydrofuran, and the mixture was reacted for one hour under reflux.

After completion of the reaction, tetrahydrofuran, etc. were distilled off under reduced pressure to obtain 3.3 g of 3-cyclopropyl-5-hydroxypyrazole (after-mentioned Intermediate No. 3-1) having a melting point of from 213 to 217° C. The NMR spectrum data of this product are as follows.

$^1$H-NMR δppm [Solvent: heavy MDSO] 0.57–0.61 (m,2H), 0.81–0.86 (m,2H), 1.70–1.77 (m,1H), 5.1 (s,1H), 10.16 (bs,1H)

2) 1.61 g of 3-cyclopropyl-5-hydroxypyrazole obtained in the preceding step was mixed with a solution having 1.89 g of dry potassium carbonate dissolved in 20 ml of hexamethylphosphoric triamide, and the mixture was cooled within a range of from 0 to 2° C. Then, iodoethane was dropwise added thereto within a range of from 0 to 5° C. over a period of about 15 minutes. Then, the mixture was reacted for one hour at the same temperature and then further reacted for one hour within a range of from room temperature to 40° C.

3) 2.72 g of 2,4-dichlorobenzoyl chloride was added thereto at room temperature, and the mixture was reacted for 0.5 hour at the same temperature and further reacted for 0.5 hour at 40° C.

After completion of the reaction, the reaction mixture was put into water and extracted with toluene. The obtained toluene layer was thoroughly washed with water and then with a saturated sodium chloride aqueous solution and then dried over anhydrous sodium sulfate. Then, toluene was distilled off under reduced pressure, and the obtained residue was purified by silica gel column chromatography to obtain 1.2 g of 3-cyclopropyl-1-ethyl-5-pyrazolyl 2,4-dichlorobenzoate (after-mentioned Intermediate No. 2a-7) having a melting point of from 61 to 63° C. The NMR spectrum data of this product are as follows.

$^1$H-NMR δppm [Solvent: CDCl$_3$] 0.69–0.73 (m,2H), 0.87–0.9 (m,2H), 1.4 (t,3H), 1.85–1.92 (m,1H), 4.02–4.08 (q,2H), 5.92 (s,1H), 7.39 (d,1H), 7.55 (s,1H), 7.94 (d,1H)

4) Using 1.1 g of 3-cyclopropyl-1-ethyl-5-pyrazolyl 2,4-dichlorobenzoate obtained in the preceding step, 0.843 g of the desired product having a melting point of from 74 to 77° C. was obtained in the same manner as Step 4) in Preparation Example 1.

PREPARATION EXAMPLE 4

Preparation of 3-cyclopropyl-4-(4-trifluoromethyl-2-methylsulfonylbenzoyl)-1-methyl-5-pyrazolyl benzene sulfonate (after-mentioned Compound No. a-27)

1) 0.57 g of 3-cyclopropyl-1-methyl-5-pyrazolyl 4-trifluoromethyl-2-methylsulfonyl benzoate (after-mentioned Intermediate No. 2a-5), 20 ml of toluene and 1 ml of N,N-dimethylformamide were charged into an Erlenmeyer flask, and 0.11 g of potassium carbonate was added thereto. The mixture was reacted for 15 hours under an azeotropic dehydration condition to obtain a reaction mixture containing a potassium salt of 3-cyclopropyl-4-(4-trifluoromethyl-2-methylsulfonylbenzoyl)-5-hydroxy-1-methylpyrazole.

2) The reaction mixture obtained in the preceding step was left to cool, and 0.1 g of tetraethylammonium chloride and 0.1 g of potassium iodide were added thereto. Then, 0.27 g of benzene sulfonyl chloride was added thereto. The mixture was reacted for 5.5 hours at 55° C. with stirring.

After completion of the reaction, the reaction mixture was put into water and extracted with ethyl acetate. Then, the extract was washed with water. The obtained organic layer was dried over anhydrous sodium sulfate, then concentrated and thereafter purified by silica gel column chromatography to obtain 0.49 g of the desired product having a melting point of from 175 to 178° C. The NMR spectrum data of this product are as follows.

$^1$H-NMR δppm [Solvent: CDCl$_3$] 0.46–0.05 (m,2H), 0.73–0.81 (m,2H), 1.33–1.41 (m,1H), 3.27 (s,3H), 3.63 (s,3H), 7.53–7.58 (m,3H), 7.7 (t,1H), 7.85 (d,1H), 7.96 (d,2H), 8.27 (s,1H)

PREPARATION EXAMPLE 5

Preparation of 3-cyclopropyl-4-(4-trifluoromethyl-2-methylsulfonylbenzoyl)-1-methyl-5-pyrazolyl n-propanesulfonate (after-mentioned Compound No. a-89)

A mixture comprising 0.4 g of 3-cyclopropyl-4-4-trifluoromethyl-2-methylsulfonylbenzoyl)-5-hydroxy-1-methylpyrazole (after-mentioned Compound No. a-11), 20 ml of toluene, 5 ml of N,N-dimethylformamide, 5 mg of tetraethylammonium bromide and 0.16 g of n-propanesulfonyl chloride, was reacted for about 12 hours at 40° C. with stirring.

After completion of the reaction, the reaction mixture was put into water and extracted with ethyl acetate. The obtained ethyl acetate layer was washed with a saturated sodium chloride aqueous solution and then dried over anhydrous sodium sulfate. Then, ethyl acetate was distilled off under reduced pressure. The obtained residue was purified by silica gel column chromatography to obtain 0.34 g of the desired product having a melting point of from 128 to 131° C. The NMR spectrum data of this product are as follows.

$^1$H-NMR δppm [Solvent: CDCl$_3$] 0.43–0.51 (m,2H), 0.78–0.82 (m,2H), 1.12 (t,3H), 1.1–1.2 (m,1H), 2.0–2.1 (m,2H), 3.33 (s,3H), 3.53 (t,2H), 3.82 (s,3H), 7.70 (d,1H), 7.96 (d,1H), 8.38 (s,1H)

PREPARATION EXAMPLE 7

Preparation of 5-benzyloxy-3-cyclopropyl-4-(4-trifluoromethyl-2-methylsulfonylbenzoyl)-1-methylpyrazole (after-mentioned Compound No. a-94)

0.14 g of benzyl chloride was added to a mixture comprising 0.4 g of 3-cyclopropyl-4-(4-trifluoromethyl-2-methylsulfonylbenzoyl)-5-hydroxy-1-methylpyrazole (after-mentioned Compound No. a-11), 0.16 g of dry potassium carbonate, 5 mg of benzyltriethylammonium chloride, 5 mg of potassium iodide, 20 ml of toluene and 5 ml of N,N-dimethylformamide, and the mixture was reacted for 24 hours within a range of from 50 to 70° C. with stirring.

After completion of the reaction, the reaction mixture was put into water and extracted with ethyl acetate. The obtained ethyl acetate layer was washed with a saturated sodium chloride aqueous solution and then dried over anhydrous sodium sulfate. Then, ethyl acetate was distilled off under reduced pressure. The obtained residue was purified by silica gel column chromatography to obtain 0.25 g of the desired product having a melting point of from 154 to 157° C. The NMR spectrum data of this product are as follows.

$^1$H-NMR δppm [Solvent: CDCl$_3$] 0.68–0.71 (m,2H), 0.85–0.88 (m,2H), 1.8–2.0 (m,1H), 3.35 (s,3H), 3.42 (s,3H), 5.00 (s,2H), 7.11–7.12 (m,2H), 7.26–7.30 (m,3H), 7.58–7.60 (d,1H), 7.58–7.88 (d,1H), 8.34 (s,1H)

PREPARATION EXAMPLE 8

Preparation of 5-(2-chloro-2-propenyloxy)-3-cyclopropyl-4-(4-trifluoromethyl-2-methylsulfonylbenzoyl)-1-methylpyrazole (after-mentioned Compound No. a-213)

A mixture comprising 0.776 g of 3-cyclopropyl-4-(4-trifluoromethyl-2-methylsulfonylbenzoyl)-5-hydroxy-1- methylpyrazole (after-mentioned Compound No. a-11), 30 ml of toluene, 4 ml of N,N-dimethylformamide, 5 mg of tetraethylammonium bromide and 0.245 g of 2,3-dichloropropene, was reacted for 1 hour at room temperature, then reacted for 4 hours at a temperature of from 60 to 80° C. with stirring.

After completion of the reaction, the reaction mixture was put into water and extracted with ethyl acetate. The obtained ethyl acetate layer was washed with a saturated sodium chloride aqueous solution and then dried over anhydrous sodium sulfate. Then, ethyl acetate was distilled off. The obtained residue was purified by silica gel column chromatography to obtain 0.65 g of the desired product having a melting point of from 180 to 111° C. The NMR spectrum data of this product are as follows.

$^1$H-NMR δppm [Solvent: $CDCl_3$] 0.59–0.61 (m,2H), 0.84–0.86 (m,2H), 1.6–1.7 (m,1H), 3.38 (s,3H), 3.67 (s,3H), 4.68 (s,2H), 5.37–5.4 (d,2H), 7.62 (d,1H), 7.93 (d,1H), 8.38 (s,1H)

PREPARATION EXAMPLE 9

Preparation of 3-cyclopropyl-1-methyl-4-(2-methylthio-4-trifluoromethylbenzoyl)-5-hydroxypyrazole (after-mentioned Compound No. a-82), 3-cyclopropyl-1-methyl-4-(2-methylthio-4-trifluoromethylbenzoyl)-5-pyrazolyl p-toluene sulfonate (after-mentioned Compound No. a-72) and 3-cyclopropyl-4-(4-trifluoromethyl-2-methylsulfonylbenzoyl)1-methyl-5-pyrazolyl p-toluene sulfonate (after-mentioned Compound No. a-12)

1) Into a 200 ml autoclave, 1.59 g of 4-iodo-3-methylthiobenzotrifluoride prepared in accordance with the following Preparation Example 10, 1.38 g of 3-cyclopropyl-5-hydroxy-1-methylpyrazole (after-mentioned Intermediate No. 1a-1), 0.5 g of triethylamine, 3.1 g of potassium carbonate, 0.22 g of palladium (II) bis-triphenylphosphine) dichloride and 40 ml of dioxane were put and sealed, and the interior of the autoclave was flushed with carbon monoxide (pressure: 65 kg/cm$^2$), followed by a reaction at 140° C. for 8 hours. After completion of the reaction, the solvent was distilled off, and the residue was dissolved in water, and then insoluble matters were filtered off. The filtrate was washed with dichloromethane. The washed product was acidified (pH=1) with concentrated hydrochloric acid and extracted with dichloromethane. The obtained extract solution was dried over anhydrous sodium sulfate, and the solvent was distilled off to obtain 1.59 g of 3-cyclopropyl-1-methyl-4-(2-methylthio-4-trifluoromethylbenzoyl)-5-hydroxypyrazole (after-mentioned Compound No. a-82) as a reddish brown solid.

2) 1.59 g of 3-cyclopropyl-1-methyl-4-(2-methylthio-4-trifluoromethylbenzoyl)-5-hydroxypyrazole obtained in the preceding step was mixed, without purification, with 20 ml of toluene, 4 ml of N,N-dimethylformamide, 0.94 g of p-toluene sulfonyl chloride and 0.34 g of potassium carbonate, and the mixture was reacted at 60° C. for 3 hours. After completion of the reaction, water was added to the reaction mixture, and the mixture was extracted with ethyl acetate. The extract solution was dried over anhydrous sodium sulfate, and the solvent was distilled off. The obtained residue was purified by silica gel column chromatography (developing solvent: ethyl acetate/hexane=¼) to obtain 0.53 g of 3-cyclopropyl-1-methyl-4-(2-methylthio-4-trifluoromethylbenzoyl)-5-pyrazolyl p-toluene sulfonate (after-mentioned Compound No. a-72). The NMR spectrum data of this product are as follows.

$^1$H-NMR δppm [Solvent: $CDCl_3$] 0.79 (m,2H), 0.90 (m,2H), 1.97 (m,1H), 2.39 (s,3H), 2.47 (s,3H), 7.23 (d,2H), 7.32 (d,1H), 7.48 (s,1H), 7.49 (d,1H), 7.53 (d,2H)

3). 0.46 g of 3-cyclopropyl-1-methyl-4-(2-methylthio-4-trifluoromethylbenzoyl)-5-pyrazolyl p-toluene sulfonate obtained in the preceding step was dissolved in 10 ml of dichloromethane, and 0.47 g of 85% methachloroperbenzoic acid was added thereto under cooling with ice. Then, the mixture was returned to room temperature and reacted over night with stirring. After completion of the reaction, an aqueous sodium hydrogen carbonate solution was added to the reaction mixture, and the mixture was extracted with dichloromethane. The extract layer was dried over anhydrous sodium sulfate, and the solvent was distilled off. The obtained residue was purified by silica gel column chromatography (developing solvent: ethyl acetate/hexane=3/7) to obtain 0.49 g of 3-cyclopropyl-4-(4-trifluoromethyl-2-methylsulfonylbenzoyl)-1-methyl-5-pyrazolyl p-toluene sulfonate (after-mentioned Compound No. a-12).

PREPARATION EXAMPLE 10

Preparation of 4-iodo-3-methylthiobenzotrifluoride 1) 123.85 g of sodium iodide was added to a solution having 42.23 g of 4-chloro-3-nitrobenzotrifluoride dissolved in 200 ml of N,N-dimethylformamide, and the mixture was reacted at 140° C. for 17 hours.

After completion of the reaction, the reaction mixture was put into water and extracted with ethyl ether. The ethyl ether layer was washed with water and then dried over anhydrous sodium sulfate. Then, ethyl ether was distilled off. The obtained residue was purified by silica gel column chromatography to obtain 44.15 g of 4-iodo-3-nitrobenzotrifluoride. The NMR spectrum data of this product are as follows.

$^1$H-NMR δppm [Solvent: $CDCl_3$] 7.52 (dd,1H), 8.11 (s,1H), 8.22 (d,1H)

2) A solution having 30 g of 4-iodo-3-nitrobenzotrifluoride obtained in the preceding step dissolved in 300 ml of acetic acid, was heated, and 26.43 g of reduced iron was added thereto over a period of 15 minutes at a temperature of from 85 to 95° C. Then, the mixture was reacted for further 5 minutes at the same temperature.

After completion of the reaction, the reaction mixture was cooled with ice, and insoluble matters were filtered off using celite. The filtration cake was thoroughly washed with ethyl acetate, and the washing liquid and the filtrate were mixed, followed by washing with water for 5 times. The obtained ethyl acetate layer was dried over anhydrous sodium sulfate, and ethyl acetate was distilled off under reduced pressure. The obtained residue was purified by silica gel column chromatography to obtain 25.52 g of oily 3-amino-4-iodobenzotrifluoride. The NMR spectrum data of this product are as follows.

hu 1H-NMR δppm [Solvent: $CDCl_3$] 6.70 (dd,1H), 6.93 (d,1H), 7.73 (d,1H)

3) To a solution containing a part (5.1 g) of 3-amino-4-iodebenzotrifluoride obtained in the preceding step, 16.75 g of dimethyldisulfide and 80 ml of chloroform, a solution having the rest (20.42 g) of 3-amino-4-iodebenzotrifluoride obtained in the preceding step dissolved in 20 ml of chloroform and 11.92 g of tert-butylnitrite, were simultaneously dropwise added at a temperature of from 25 to 30° C. After completion of the dropwise addition, the mixture was reacted at room temperature for 16 hours.

After completion of the reaction, 200 ml of methylene chloride was added to the reaction mixture, and the mixture was washed with an aqueous hydrochloric acid solution with pH 1 to 2. Then, the methylene chloride layer was washed with water and dried over anhydrous sodium sulfate. Then, methylene chloride and chloroform were distilled off under reduced pressure. The obtained residue was purified by silica gel column chromatography to obtain 19.89 g of the desired product as an oily substance. The NMR spectrum data of this product are as follows.

$^1$H-NMR δppm [Solvent: CDCl$_3$] 2.51 (s,3H), 7.08 (dd, 1H), 7.26 (d,1H), 7.90 (dd,1H)

Other compounds of the present invention can be prepared in accordance with the above described Preparation Examples or the above described various processes for producing the compounds of the present invention. Typical examples of the intermediate compound represented by the above formula (II) will be shown in Table 1, typical examples of the intermediate compound represented by the above formula (IV) will be presented in Tables 2a and 2b, typical examples of the intermediate compound represented by the above formula (IX) will be presented in Table 3, and typical examples of the compound of the present invention represented by the above formula (I) will be presented in Tables 4a and 4b.

TABLE 1

(11)

| Intermediate No. | R$_1$ | (Z)$_l$ group | Physical properties |
|---|---|---|---|
| 1a-1 | CH$_3$ | cyclopropyl | m.p. 95–121° C. |
| 1a-2 | CH$_2$CH$_3$ | cyclopropyl | |
| 1a-3 | n-C$_3$H$_7$ | cyclopropyl | |
| 1a-4 | n-C$_4$H$_9$ | cyclopropyl | |
| 1a-5 | CH(CH$_3$)$_2$ | cyclopropyl | |

TABLE 1-continued (11)

| Intermediate No. | R$_1$ | (Z)$_l$ group | Physical properties |
|---|---|---|---|
| 1b-1 | CH$_3$ | 2-methylcyclopropyl | |
| 1b-2 | CH$_2$CH$_3$ | 2-methylcyclopropyl | |
| 1b-3 | n-C$_3$H$_7$ | 2-methylcyclopropyl | |
| 1b-4 | n-C$_4$H$_9$ | 2-methylcyclopropyl | |
| 1b-5 | CH(CH$_3$)$_2$ | 2-methylcyclopropyl | |

TABLE 2a (IVa)

| Intermediate No. | R$_1$ | aryl group | Physical properties |
|---|---|---|---|
| 2a-1 | CH$_3$ | 2,4-dichlorophenyl | |

TABLE 2a-continued (IVa)

| Intermediate No. | R$_1$ | Aryl (X)n | Physical properties |
|---|---|---|---|
| 2a-2 | CH$_3$ | 2-NO$_2$, 4-Cl phenyl | m.p. 84–87° C. |
| 2a-3 | CH$_3$ | 2-Cl, 4-SO$_2$CH$_3$ phenyl | m.p. 148–150° C. |
| 2a-4 | CH$_3$ | 2-Cl, 3-CH$_3$, 4-Cl phenyl | |
| 2a-5 | CH$_3$ | 2-SO$_2$CH$_3$, 4-CF$_3$ phenyl | m.p. 99–102° C. |
| 2a-6 | CH$_3$ | 2-NO$_2$, 4-SCH$_3$ phenyl | |
| 2a-7 | CH$_2$CH$_3$ | 2,4-di-Cl phenyl | m.p. 61–63° C. |
| 2a-8 | CH$_3$ | 2-NO$_2$, 4-SO$_2$CH$_3$ phenyl | |
| 2a-9 | CH$_2$CH$_3$ | 2-Cl, 4-SO$_2$CH$_3$ phenyl | m.p. 96–99° C. |
| 2a-10 | CH$_3$ | 2-Cl, 4-SCH$_3$ phenyl | Viscous |
| 2a-11 | CH$_3$ | 2,4-di-Cl phenyl | |
| 2a-12 | CH$_2$CH$_3$ | 2-Cl, 3-CH$_3$, 4-SO$_2$CH$_3$ phenyl | |
| 2a-13 | n-C$_3$H$_7$ | 2-Cl, 4-SO$_2$CH$_3$ phenyl | |
| 2a-14 | CH$_2$CH$_3$ | 2-SO$_2$CH$_3$, 4-CF$_3$ phenyl | m.p. 94–97° C. |
| 2a-15 | CH(CH$_3$)$_2$ | 2-SO$_2$CH$_3$, 4-CF$_3$ phenyl | |

TABLE 2a-continued (IVa)

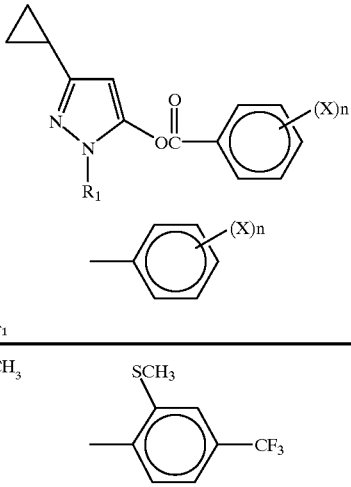

| Intermediate No. | R₁ | (Ar) | Physical properties |
|---|---|---|---|
| 2a-16 | CH₃ | 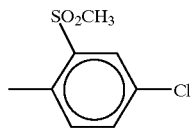 2-CH₃, 3-SCH₃, 5-CF₃ | Oily |
| 2a-17 | CH₃ | 2-CH₃, 3-SO₂CH₃, 5-Cl | m.p. 136–140° C. |
| 2a-18 | CH₃ | 2-CH₃, 3-Cl, 5-NO₂ | |
| 2a-19 | CH₃ | 2-CH₃, 3-SCH₃, 5-Cl | m.p. 90–93° C. |
| 2a-20 | CH₂CH₃ | 2-CH₃, 3-NO₂, 5-Cl | |
| 2a-21 | CH₃ | 2-CH₃, 3-SO₂CH₂CH₃, 5-CF₃ | Viscous |
| 2a-22 | CH₃ | 2-CH₃, 3-SCH₂CH₃, 5-CF₃ | Viscous |
| 2a-23 | CH₃ | 2-CH₃, 3-CF₃, 4-SCH₃ | Viscous |
| 2a-24 | CH₃ | 2-CH₃, 3-CF₃, 5-SO₂CH₃ | m.p. 146–149° C. |
| 2a-25 | CH₃ | 2-CH₃, 3-Cl (and CH₃), 5-SO₂CH₃ | m.p. 125–130° C. |
| 2a-26 | CH₃ | 2-CH₃, 3-SCH₃, 4-Cl, 5-Cl | |
| 2a-27 | CH₃ | 2-CH₃, 3-SOCH₃, 4-Cl, 5-Cl | |
| 2a-28 | CH₃ | 2-CH₃, 3-SO₂CH₃, 4-Cl, 5-Cl | m.p. 134–136° C. |
| 2a-29 | CH₃ | 2-CH₃, 3-SCH₃, 4-F, 5-F | |

TABLE 2a-continued (IVa)

| Intermediate No. | R₁ | (aryl substituents) | Physical properties |
|---|---|---|---|
| 2a-30 | CH₃ | 2-SOCH₃, 3-F, 4-F | |
| 2a-31 | CH₃ | 2-SO₂CH₃, 3-F, 4-F | |
| 2a-32 | CH₃ | 2-SCH₃ | |
| 2a-33 | CH₃ | 2-SO₂CH₃ | |
| 2a-34 | CH₃ | 2-SCH₂CH₃, 3-Cl, 4-Cl | |
| 2a-35 | CH₃ | 2-SOCH₂CH₃, 3-Cl, 4-Cl | |
| 2a-36 | CH₃ | 2-SO₂CH₂CH₃, 3-Cl, 4-Cl | |
| 2a-37 | CH₃ | 2-Cl, 3-CO₂CH₃, 6-SO₂CH₃ | |
| 2a-38 | CH₃ | 2-NO₂, 4-CF₃ | |
| 2a-39 | CH₃ | 2-OSO₂CH₃, 4-Cl | |
| 2a-40 | CH₃ | 2-CH₂SCH₃, 4-Cl | |
| 2a-41 | CH₃ | 2-CH₂SOCH₃, 4-Cl | |
| 2a-42 | CH₃ | 2-CH₂SO₂CH₃, 4-Cl | |
| 2a-43 | CH₃ | 2-SCH₃, 4-NO₂ | m.p. 118–122° C. |

TABLE 2a-continued

Structure (IVa): 3-cyclopropyl-1-R₁-pyrazol-5-yl ester of substituted benzoic acid, with aryl group bearing (X)n substituents.

| Intermediate No. | R₁ | Aryl (X)n substituents | Physical properties |
|---|---|---|---|
| 2a-44 | CH₃ | 2-SO₂CH₃, 4-NO₂ | |
| 2a-45 | CH₃ | 2-SCH₃, 3-Cl, 4-CF₃ | Viscous |
| 2a-46 | CH₃ | 2-SO₂CH₃, 3-Cl, 4-CF₃ | |
| 2a-47 | CH₃ | 2-SCH₃, 3-Cl, 5-Cl | |
| 2a-48 | CH₃ | 2-SOCH₃, 3-Cl, 5-Cl | |
| 2a-49 | CH₃ | 2-SO₂CH₃, 3-Cl, 5-Cl | |
| 2a-50 | CH₃ | 2-N(CH₃)SO₂CH₃, 4-Cl | |
| 2a-51 | CH₃ | 2-SCH₃, 4-CF₃, 5-Cl | |
| 2a-52 | CH₃ | 2-SOCH₃, 4-CF₃, 5-Cl | |
| 2a-53 | CH₃ | 2-SO₂CH₃, 4-CF₃, 5-Cl | |
| 2a-54 | CH₃ | 2-SCH₃, 4-CH₃ | |
| 2a-55 | CH₃ | 2-SOCH₃, 4-CH₃ | |

TABLE 2a-continued (IVa)

| Intermediate No. | R₁ | (substituent aryl) | Physical properties |
|---|---|---|---|
| 2a-56 | CH₃ | 2-SO₂CH₃, 4-CH₃ phenyl | |
| 2a-57 | CH₃ | 2-Cl, 4-SO₂N(CH₃)₂ phenyl | |
| 2a-58 | CH₃ | 2-SOCH₂CH₃, 4-CF₃ phenyl | |
| 2a-59 | CH₃ | 2-SOCH₃, 4-CF₃ phenyl | |
| 2a-60 | CH₃ | 2-CH₂SO₂CH₃, 3-Cl, 4-Cl phenyl | |
| 2a-61 | CH₃ | 2-SC₃H₇(iso), 4-CF₃ phenyl | |
| 2a-62 | CH₃ | 2-SOC₃H₇(iso), 4-CF₃ phenyl | |
| 2a-63 | CH₃ | 2-SO₂C₃H₇(iso), 4-CF₃ phenyl | |
| 2a-64 | CH₃ | 2,3,4-trichlorophenyl | |
| 2a-65 | CH₃ | 2,3,4,5-tetrachlorophenyl | |

TABLE 2b
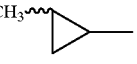
(IV)
| Intermediate No. | R₁ | 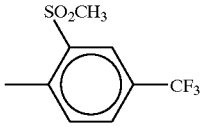 (Z)ₗ |  (X)ₙ | Physical properties |
|---|---|---|---|---|
| 2b-1 | CH₃ | 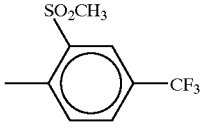 | $SO_2CH_3$, $CF_3$ | Viscous |
| 2b-2 | CH₂CH₃ |  | $SO_2CH_3$, $CF_3$ | |
| 2b-3 | CH₃ | 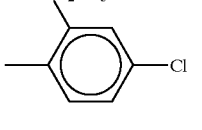 | $SO_2CH_3$, Cl | |
| 2b-4 | CH₃ |  | $CF_3$, $SO_2CH_3$ | |
| 2b-5 | CH₃ | 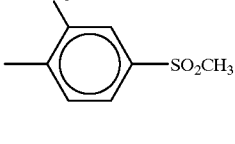 | $SCH_3$, $CF_3$ | |
| 2b-6 | CH₃ |  | Cl, CH₃, $SO_2CH_3$ | |

TABLE 3

(IX)

| Intermediate No. | (Z)₁ group | Physical properties |
|---|---|---|
| 3-1 | cyclopropyl (dashed bond) | m.p. 213–217° C. |
| 3-2 | CH₃-cyclopropyl (wavy bond) | |

TABLE 4a (Ia)

| Compound No. | $R_1$ | $R_2$ | (X)n aryl | Physical properties |
|---|---|---|---|---|
| a-1 | CH₃ | H | 2,4-di-Cl-phenyl | m.p. 131–133° C. |
| a-2 | CH₃ | —SO₂—C₆H₄—CH₃ | 2,4-di-Cl-phenyl | Refractive index $n_D^{43.4}$ 1.5779 |
| a-3 | CH₃ | H | 2-NO₂-4-Cl-phenyl | m.p. 65–70° C. |

TABLE 4a-continued
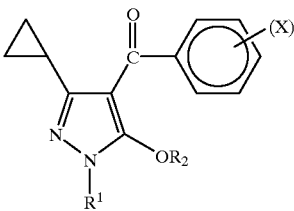
(Ia)
| Compound No. | R₁ | R₂ | | Physical properties |
|---|---|---|---|---|
| a-4 | CH₃ | 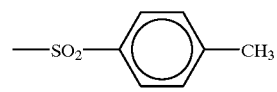 | 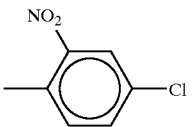 | m.p. 130–133° C. |
| a-5 | CH₃ | H | 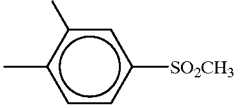 | m.p. 163–166° C. |
| a-6 | CH₃ | 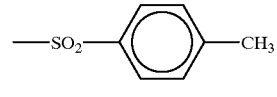 | 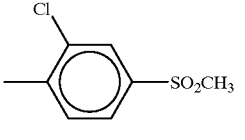 | m.p. 172–174° C. |
| a-7 | CH₃ | 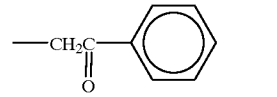 | 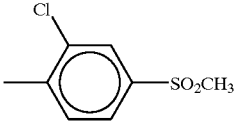 | m.p. 145–147° C. |
| a-8 | CH₃ | H | 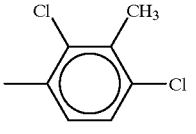 | m.p. 112–115° C. |
| a-9 | CH₃ | 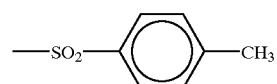 | 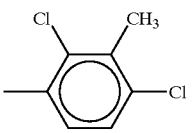 | m.p. 115–118° C. |
| a-10 | CH₃ | 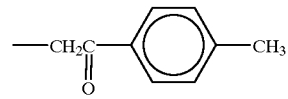 | 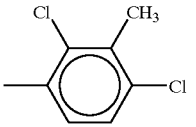 | m.p. 126–129° C. |

TABLE 4a-continued
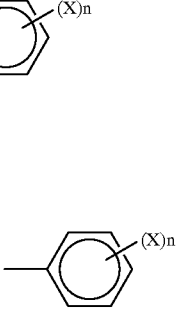
(Ia)
| Compound No. | R₁ | R₂ | | Physical properties |
|---|---|---|---|---|
| a-11 | CH₃ | H | (2-methyl-5-CF₃-4-SO₂CH₃-phenyl) | m.p. 153–157° C. |
| a-12 | CH₃ | —SO₂—C₆H₄—CH₃ | (2-methyl-5-CF₃-4-SO₂CH₃-phenyl) | m.p. 135–138° C. |
| a-13 | CH₃ | —CH₂C(O)—C₆H₅ | (2-methyl-5-CF₃-4-SO₂CH₃-phenyl) | m.p. 124–127° C. |
| a-14 | CH₃ | —C(O)CH₃ | (2,4-dichloro-3-methyl-phenyl) | m.p. 112–115° C. |
| a-15 | CH₃ | H | (2-methyl-3-NO₂-4-SCH₃-phenyl) | m.p. 115–122° C. |
| a-16 | CH₃ | —SO₂—C₆H₄—CH₃ | (2-methyl-3-NO₂-4-SCH₃-phenyl) | m.p. 146–148° C. |
| a-17 | CH₃ | —CH₂C(O)—C₆H₅ | (2-methyl-3-NO₂-4-SCH₃-phenyl) | Viscous |

TABLE 4a-continued
(Ia)
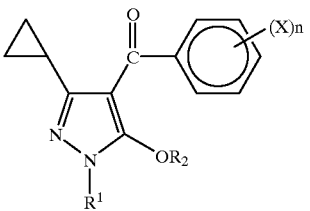
| Compound No. | R₁ | R₂ | | Physical properties |
|---|---|---|---|---|
| a-18 | $CH_2CH_3$ | H | 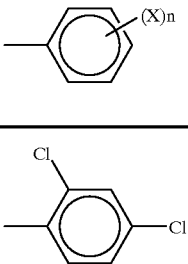 | m.p. 74–77° C. |
| a-19 | $CH_2CH_3$ | 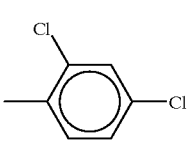 | 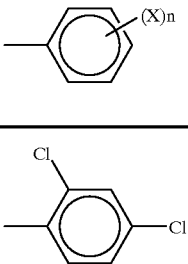 | Viscous |
| a-20 | $CH_3$ | 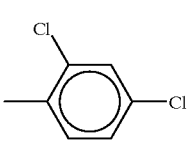 | 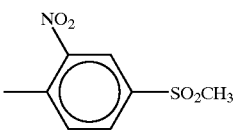 | m.p. 181–183° C. |
| a-21 | $CH_2CH_3$ | H | 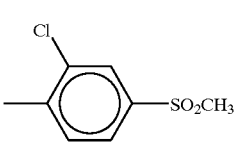 | m.p. 158–161° C. |
| a-22 | $CH_2CH_3$ | 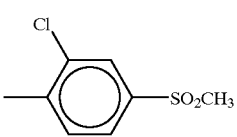 | 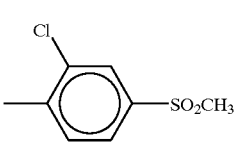 | m.p. 116–118° C. |
| a-23 | $CH_2CH_3$ | 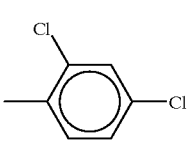 | 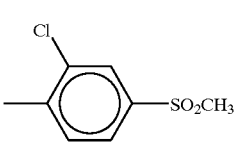 | m.p. 146–148° C. |
| a-24 | $CH_3$ | H | 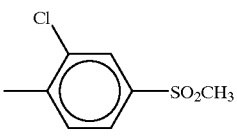 | m.p. 111–114° C. |

TABLE 4a-continued
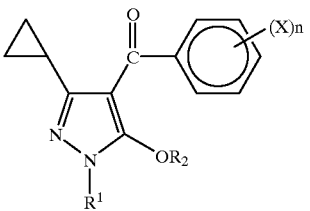
(Ia)
| Compound No. | R₁ | R₂ | (X)n aryl | Physical properties |
|---|---|---|---|---|
| a-25 | CH₃ | —CH₂C(=O)—C₆H₅ | 2-Cl, 4-SCH₃ phenyl | Refractive index $n_D^{46.6}$ 1.6001 |
| a-26 | CH₃ | H | 2-NO₂, 4-SO₂CH₃ phenyl | m.p. 140–145° C. |
| a-27 | CH₃ | —SO₂—C₆H₅ | 2-SO₂CH₃, 4-CF₃ phenyl | m.p. 175–178° C. |
| a-28 | CH₃ | —SO₂—C₆H₄—CH₃ | 2-Cl, 4-Cl phenyl | |
| a-29 | CH₃ | —CH₂C(=O)—C₆H₅ | 2-Cl, 4-Cl phenyl | |
| a-30 | CH₃ | —CH₂C(=O)—C₆H₅ | 2-NO₂, 4-Cl phenyl | |
| a-31 | CH₂CH₃ | —SO₂—C₆H₅ | 2-NO₂, 4-Cl phenyl | |

TABLE 4a-continued
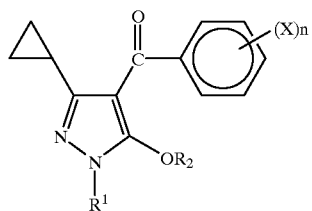
(Ia)
| Compound No. | R₁ | R₂ | | Physical properties |
|---|---|---|---|---|
| a-32 | CH₂CH₃ | —SO₂—C₆H₅ | 2-Cl, 4-SO₂CH₃ phenyl | |
| a-33 | CH₃ | —SO₂—C₆H₄—Cl (4-Cl) | 2-Cl, 4-SO₂CH₃ phenyl | |
| a-34 | CH₃ | —SO₂—C₆H₄—Cl (3-Cl) | 2-Cl, 4-SO₂CH₃ phenyl | |
| a-35 | CH₃ | —SO₂—C₆H₄—Cl (2-Cl) | 2-Cl, 4-SO₂CH₃ phenyl | |
| a-36 | CH₃ | —SO₂—C₆H₄—OCH₃ (4-OCH₃) | 2-Cl, 4-SO₂CH₃ phenyl | |
| a-37 | CH₃ | —SO₂—C₆H₄—OCH₃ (2-OCH₃) | 2-Cl, 4-SO₂CH₃ phenyl | |
| a-38 | CH₃ | —SO₂—C₆H₄—CF₃ (3-CF₃) | 2-Cl, 4-SO₂CH₃ phenyl | |

TABLE 4a-continued
(Ia)
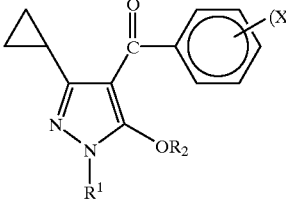
| Compound No. | R₁ | R₂ | | Physical properties |
|---|---|---|---|---|
| a-39 | CH₃ | —SO₂CH₃ |  | m.p. 143–146° C. |
| a-40 | CH₃ | —SO₂CH₂CH₃ | 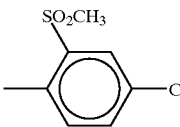 | m.p. 127–130.5° C. |
| a-41 | CH₃ | 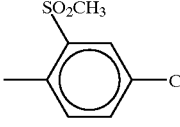 | 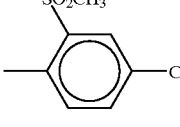 | m.p. 117–120° C. |
| a-42 | CH₃ | 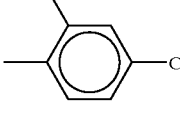 | 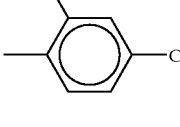 | m.p. 196–199° C. |
| a-43 | CH₃ | 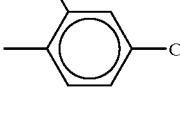 | 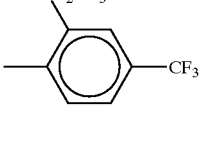 | m.p. 157–160° C. |
| a-44 | CH₃ | (—SO₂-phenyl with Cl at 2-position) | (SO₂CH₃, CF₃ phenyl) | m.p. 168–171° C. |
| a-45 | CH₃ | (—SO₂-phenyl with OCH₃ at 4-position) | (SO₂CH₃, CF₃ phenyl) | m.p. 157–160° C. |

TABLE 4a-continued
(Ia)
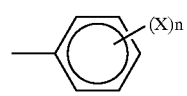
| Compound No. | R₁ | R₂ | | Physical properties |
|---|---|---|---|---|
| a-46 | CH₃ | 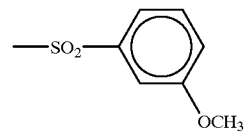 | 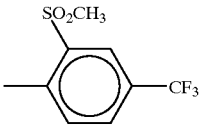 | |
| a-47 | CH₃ | 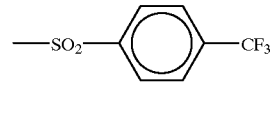 | 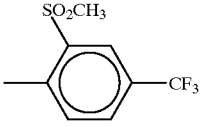 | m.p. 185–188° C. |
| a-48 | CH₃ | 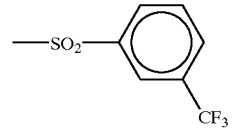 | 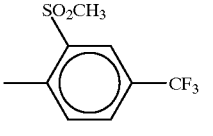 | m.p. 124–127° C. |
| a-49 | CH₃ | 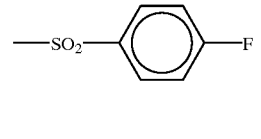 | 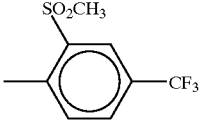 | m.p. 152–155° C. |
| a-50 | CH₃ | 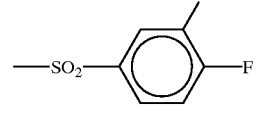 | 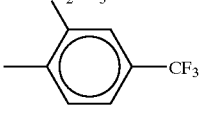 | |
| a-51 | CH₃ | 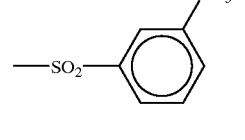 | 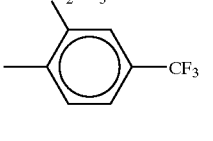 | m.p. 166–169° C. |
| a-52 | CH₃ | 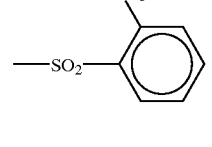 | 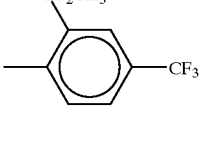 | m.p. 145–149° C. |

TABLE 4a-continued
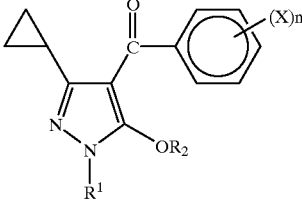
(Ia)
| Compound No. | R₁ | R₂ | | Physical properties |
|---|---|---|---|---|
| a-53 | CH₃ | —SO₂C₄H₉(n) |  | m.p. 142–145° C. |
| a-54 | CH₂CH₃ | 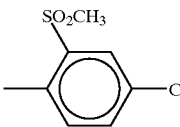 | 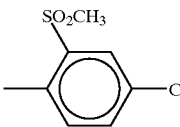 | |
| a-55 | CH₂CH₃ | 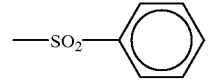 | 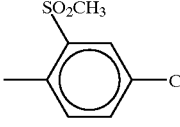 | m.p. 156–159° C. |
| a-56 | CH₂CH₃ | 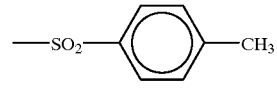 | 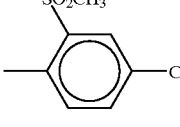 | |
| a-57 | CH₂CH₃ | 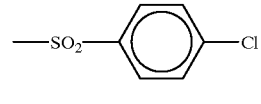 | 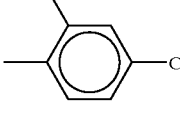 | |
| a-58 | CH₂CH₃ | 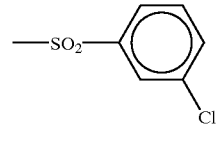 | 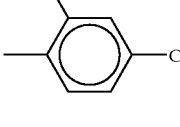 | m.p. 136–138° C. |
| a-59 | CH₃ | 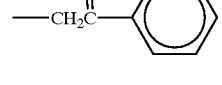 | 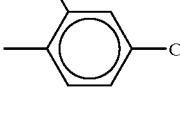 | Viscous |

TABLE 4a-continued
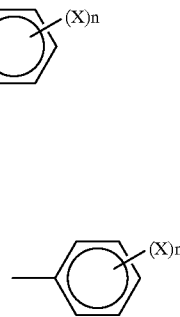
(Ia)
| Compound No. | R₁ | R₂ | | Physical properties |
|---|---|---|---|---|
| a-60 | CH₃ | —CH₂C(O)—C₆H₄—Cl (4-Cl) | 2-SO₂CH₃, 4-CF₃ phenyl | Viscous |
| a-61 | CH(CH₃)₂ | —SO₂—C₆H₅ | 2-SO₂CH₃, 4-CF₃ phenyl | |
| a-62 | CH(CH₃)₂ | —SO₂—C₆H₄—CH₃ | 2-SO₂CH₃, 4-CF₃ phenyl | |
| a-63 | n-C₃H₇ | —SO₂—C₆H₄—CH₃ | 2-SO₂CH₃, 4-CF₃ phenyl | |
| a-64 | CH₃ | —SO₂CH₃ | 2-NO₂, 4-SO₂CH₃ phenyl | |
| a-65 | CH₃ | —SO₂—C₆H₅ | 2-NO₂, 4-SO₂CH₃ phenyl | |
| a-66 | CH₃ | —SO₂—C₆H₄—CH₃ | 2-NO₂, 4-SO₂CH₃ phenyl | |

TABLE 4a-continued (Ia)

| Compound No. | R₁ | R₂ | | Physical properties |
|---|---|---|---|---|
| a-67 | CH₃ | —SO₂—C₆H₄—Cl (4-Cl) | 2-CH₃, 3-NO₂, 5-SO₂CH₃ phenyl | |
| a-68 | CH₃ | —SO₂—C₆H₄—NO₂ (4-NO₂) | 2-CH₃, 3-NO₂, 5-SO₂CH₃ phenyl | |
| a-69 | CH₃ | —SO₂—C₆H₄—NO₂ (4-NO₂) | 2-CH₃, 3-SO₂CH₃, 5-CF₃ phenyl | m.p. 208–211° C. |
| a-70 | CH₃ | —SO₂—C₆H₄—NO₂ (4-NO₂) | 2-CH₃, 3-Cl, 5-SO₂CH₃ phenyl | |
| a-71 | n-C₃H₇ | —SO₂—C₆H₄—CH₃ (4-CH₃) | 2-CH₃, 3-Cl, 5-SO₂CH₃ phenyl | |
| a-72 | CH₃ | —SO₂—C₆H₄—CH₃ (4-CH₃) | 2-CH₃, 3-SCH₃, 5-CF₃ phenyl | m.p. 107–109° C. |
| a-73 | CH₃ | —SO₂—C₆H₄—CH₃ (4-CH₃) | 2-CH₃, 3-SO₂CH₃, 5-Cl phenyl | m.p. 158–164° C. |

TABLE 4a-continued
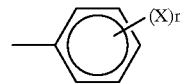
(Ia)
| Compound No. | R₁ | R₂ | | Physical properties |
|---|---|---|---|---|
| a-74 | CH₃ | —SO₂—C₆H₄—CH₃ | 2-Cl, 4-NO₂ phenyl | |
| a-75 | CH₃ | —SO₂—C₆H₄—CH₃ | 2-SCH₃, 4-Cl phenyl | |
| a-76 | CH₃ | —SO₂—C₆H₄—CH₂CH₃ | 2-SO₂CH₃, 4-CF₃ phenyl | Viscous |
| a-77 | CH₃ | H | 2-SO₂CH₃, 4-Cl phenyl | m.p. 190–204° C. |
| a-78 | CH₃ | —SO₃CH₃ | 2-SO₂CH₃, 4-Cl phenyl | m.p. 134–138° C. |
| a-79 | CH₃ | —CH₂C(O)C₆H₅ | 2-SO₂CH₃, 4-Cl phenyl | m.p. 137–139° C. |
| a-80 | CH₃ | H | 2-CH₃, 3-Cl, 4-SO₂CH₃ phenyl | m.p. 177–180° C. |

TABLE 4a-continued (Ia)

| Compound No. | R₁ | R₂ | | Physical properties |
|---|---|---|---|---|
| a-81 | CH₃ | H | 2-methyl-3-CF₃-5-SO₂CH₃-phenyl | m.p. 141–143° C. |
| a-82 | CH₃ | H | 2-methyl-3-SCH₃-5-CF₃-phenyl | m.p. 107–110° C. |
| a-83 | CH₃ | —CH₂C(O)CH₃ | 2-methyl-3-SO₂CH₃-5-CF₃-phenyl | Viscous |
| a-84 | CH₃ | —SO₂-(2,4-difluorophenyl) | 2-methyl-3-SO₂CH₃-5-CF₃-phenyl | m.p. 189–193° C. |
| a-85 | CH₃ | —CH₂C(O)-phenyl | 2-methyl-3-CF₃-5-SO₂CH₃-phenyl | m.p. 113–115° C. |
| a-86 | CH₃ | —CH₂C(O)-phenyl | 2-methyl-3-SCH₃-5-CF₃-phenyl | m.p. 146–148° C. |
| a-87 | CH₃ | —CH₂C(O)-phenyl | 2-methyl-3-SOCH₃-5-CF₃-phenyl | m.p. 148–151° C. |

TABLE 4a-continued
(Ia)
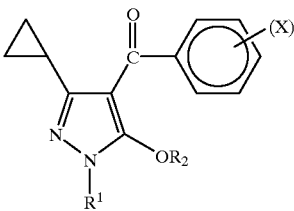
| Compound No. | R₁ | R₂ | | Physical properties |
|---|---|---|---|---|
| a-88 | CH₃ |  | 2-SO₂CH₃, 4-CF₃ (phenyl) | m.p. 137–141° C. |
| a-89 | CH₃ | —SO₂C₃H₇(n) | 2-SO₂CH₃, 4-CF₃ (phenyl) | m.p. 128–131° C. |
| a-90 | CH₃ | —SO₂-C₆H₅ | 2-Cl, 3-CH₃, 4-SO₂CH₃ (phenyl) | Viscous |
| a-91 | CH₃ | —SO₂-C₆H₄-CH₃ | 2-Cl, 3-CH₃, 4-SO₂CH₃ (phenyl) | m.p. 188–192° C. |
| a-92 | CH₃ | —SO₂-C₆H₄-CH₃ | 2-CF₃, 4-SO₂CH₃ (phenyl) | Viscous |
| a-93 | CH₃ | —SO₂-C₆H₄-CH₃ | 2-SOCH₃, 4-CF₃ (phenyl) | m.p. 128–131° C. |
| a-94 | CH₃ | —CH₂-C₆H₅ | 2-SO₂CH₃, 4-CF₃ (phenyl) | m.p. 154–157° C. |

TABLE 4a-continued
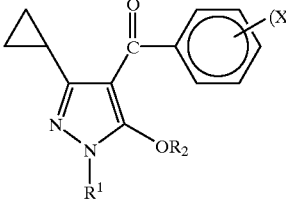
(Ia)
| Compound No. | R₁ | R₂ | | Physical properties |
|---|---|---|---|---|
| a-95 | $CH_3$ | —$CH_2CN$ |  | m.p. 135–140° C. |
| a-96 | $CH_3$ | —$CH_2CH=CH_2$ | 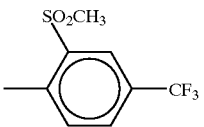 | Refractive index $n_D^{44.5}$ 1.5133 |
| a-97 | $CH_3$ | 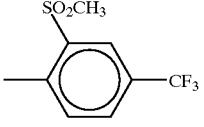 | 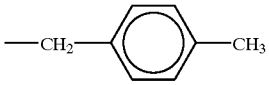 | m.p. 161–163° C. |
| a-98 | $CH_3$ | 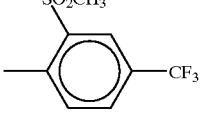 | 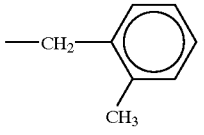 | m.p. 163–166° C. |
| a-99 | $CH_3$ | —$CH_2C≡CH$ | 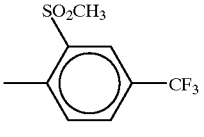 | m.p. 123–127° C. |
| a-100 | $CH_3$ | —$CH_2CH_3$ | 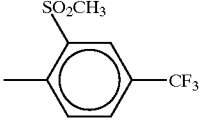 | m.p. 125–128° C. |
| a-101 | $CH_3$ | 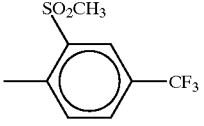 | 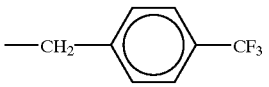 | m.p. 159–161° C. |

TABLE 4a-continued
(Ia)
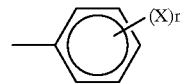
| Compound No. | R₁ | R₂ | | Physical properties |
|---|---|---|---|---|
| a-102 | CH₃ | —SO₂—⬡—CH₃ | 2-CH₃, 3-SO₂CH₂CH₃, 5-CF₃ phenyl | m.p. 63–70° C. |
| a-103 | CH₃ | —SO₂C₃H₇(n) | 2-CH₃, 3-SO₂CH₂CH₃, 5-CF₃ phenyl | m.p. 130–133° C. |
| a-104 | CH₃ | —CH₂—⬡—Cl | 2-CH₃, 3-SO₂CH₃, 5-CF₃ phenyl | m.p. 151–154° C. |
| a-105 | CH₃ | —CH₂—⬡—Br | 2-CH₃, 3-SO₂CH₃, 5-CF₃ phenyl | m.p. 160–163° C. |
| a-106 | CH₃ | H | 2-CH₃, 3-SO₂CH₂CH₃, 5-CF₃ phenyl | m.p. 140–143° C. |
| a-107 | CH₂CH₃ | H | 2-CH₃, 3-SO₂CH₃, 5-CF₃ phenyl | m.p. 109–114° C. |
| a-108 | CH₃ | —CH₂—⬡—F | 2-CH₃, 3-SO₂CH₃, 5-CF₃ phenyl | |

TABLE 4a-continued (Ia)

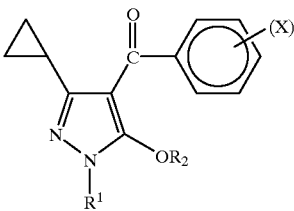

| Compound No. | R₁ | R₂ | | Physical properties |
|---|---|---|---|---|
| a-109 | $CH_3$ | 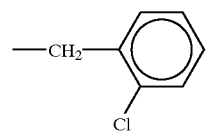 —CH₂—(2-Cl-C₆H₄) | 2-$SO_2CH_3$, 4-$CF_3$, 6-methyl phenyl | |
| a-110 | $CH_3$ | 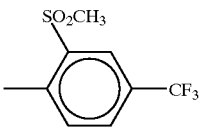 —CH₂—(3-Cl-C₆H₄) | 2-$SO_2CH_3$, 4-$CF_3$, 6-methyl phenyl | |
| a-111 | $CH_3$ | —CH₂OCH₃ | 2-$SO_2CH_3$, 4-$CF_3$, 6-methyl phenyl | |
| a-112 | $CH_3$ | —CH₂OCH₂CH₃ | 2-$SO_2CH_3$, 4-$CF_3$, 6-methyl phenyl | |
| a-113 | $CH_3$ | —CH₂COCH₃ | 2-$SO_2CH_3$, 4-$CF_3$, 6-methyl phenyl | Viscous |
| a-114 | $CH_3$ | —CH₂COCH₂CH₃ | 2-$SO_2CH_3$, 4-$CF_3$, 6-methyl phenyl | |
| a-115 | $CH_3$ | —CH₃ | 2-$SO_2CH_3$, 4-$CF_3$, 6-methyl phenyl | |

TABLE 4a-continued
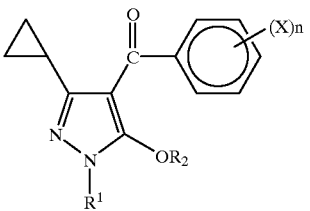
(Ia)
| Compound No. | R₁ | R₂ | | Physical properties |
|---|---|---|---|---|
| a-116 | CH₃ | —C₃H₇(n) | 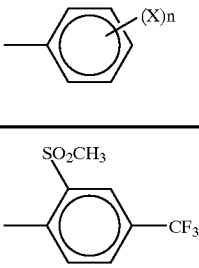 | Viscous |
| a-117 | CH₃ | —C₄H₉(n) | 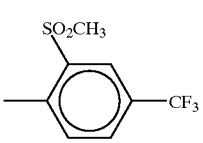 | |
| a-118 | CH₃ |  | 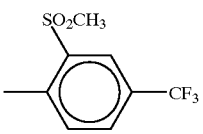 | m.p. 156–158° C. |
| a-119 | CH₃ | 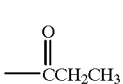 | 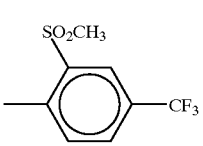 | |
| a-120 | CH₃ | 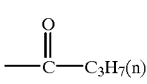 | 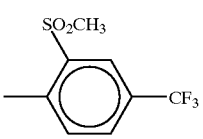 | m.p. 143–145° C. |
| a-121 | CH₃ | 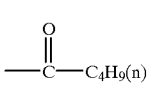 | 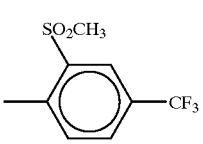 | |
| a-122 | CH₃ | 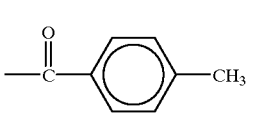 | 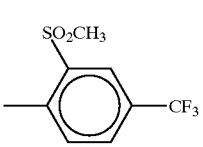 | m.p. 179–182° C. |

TABLE 4a-continued
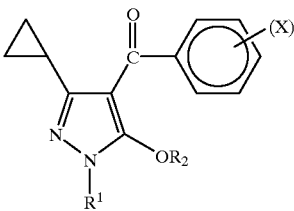
(Ia)
| Compound No. | R₁ | R₂ | | Physical properties |
|---|---|---|---|---|
| a-123 | CH₃ | —C(O)—C₆H₄—Cl (4-Cl) | 2-CH₃-3-SO₂CH₃-5-CF₃ phenyl | |
| a-124 | CH₃ | —SO₂—C₆H₄—CH₃ (4-CH₃) | 2-CH₃-3-SCH₂CH₃-5-CF₃ phenyl | |
| a-125 | CH₃ | —SO₂N(CH₃)₂ | 2-CH₃-3-Cl-4-SCH₃ phenyl | m.p. 116–118° C. |
| a-126 | CH₃ | —SO₂N(CH₃)₂ | 2-CH₃-3-SO₂CH₃-5-CF₃ phenyl | m.p. 154–158° C. |
| a-127 | CH₃ | —CON(CH₃)₂ | 2-CH₃-3-Cl-4-SCH₃ phenyl | m.p. 136–138° C. |
| a-128 | CH₃ | —CON(CH₃)₂ | 2-CH₃-3-SO₂CH₃-5-CF₃ phenyl | |
| a-129 | CH₃ | —SO₂N(CH₃)₂ | 2-CH₃-3-Cl-4-SO₂CH₃ phenyl | m.p. 50–60° C. |

TABLE 4a-continued
(Ia)
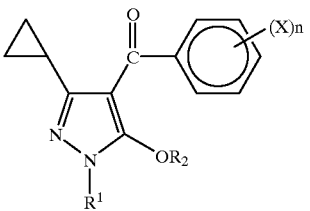
| Compound No. | R₁ | R₂ | | Physical properties |
|---|---|---|---|---|
| a-130 | CH₃ | —CON(CH₃)₂ |  | m.p. 200–203° C. |
| a-131 | CH₃ | 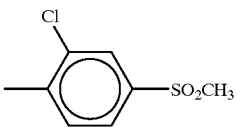 | 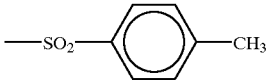 | m.p. 57–60° C. |
| a-132 | CH₃ | 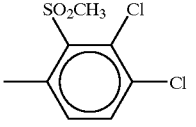 | 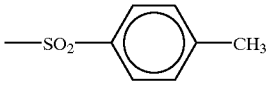 | Viscous |
| a-133 | CH₃ | 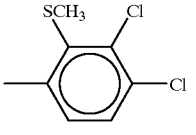 | 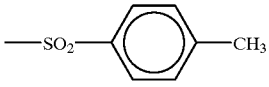 | m.p. 105–107° C. |
| a-134 | CH₃ | 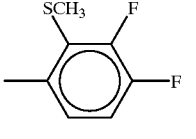 |  | m.p. 131–133° C. |
| a-135 | CH₃ | 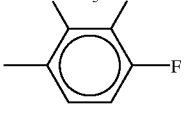 |  | m.p. 169–172° C. |
| a-136 | CH₃ | 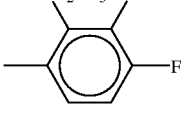 | 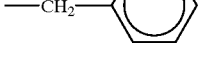 | Oily |

TABLE 4a-continued
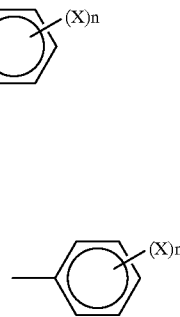
(Ia)
| Compound No. | R₁ | R₂ | | Physical properties |
|---|---|---|---|---|
| a-137 | CH₃ | —CH₂—Ph | 2-SOCH₃-3,4-F₂-C₆H₂— | Viscous |
| a-138 | CH₃ | —CH₂—Ph | 2-SO₂CH₃-3,4-F₂-C₆H₂— | m.p. 125–128° C. |
| a-139 | CH₃ | H | 2-SCH₃-3,4-F₂-C₆H₂— | Oily |
| a-140 | CH₃ | —CH(CH₃)—Ph | 2-SO₂CH₃-4-CF₃-C₆H₃— | m.p. 139–142° C. |
| a-141 | CH₃ | 2,4-(NO₂)₂-C₆H₃— | 2-SO₂CH₃-4-CF₃-C₆H₃— | m.p. 150–151° C. |
| a-142 | CH₃ | H | 2-SCH₃-C₆H₄— | m.p. 95–103° C. |
| a-143 | CH₃ | —SO₂-C₆H₄-4-CH₃ | 2-SCH₃-C₆H₄— | m.p. 92–96° C. |

TABLE 4a-continued
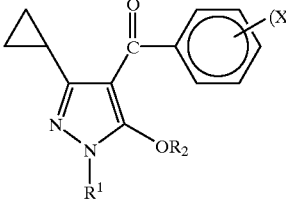
(Ia)
| Compound No. | R₁ | R₂ | | Physical properties |
|---|---|---|---|---|
| a-144 | CH₃ | H | (2-SO₂CH₃-phenyl) | m.p. 60–70° C. |
| a-145 | CH₃ | —SO₂—C₆H₄—CH₃ (p) | (2-SO₂CH₃-phenyl) | m.p. 75–80° C. |
| a-146 | CH₃ | H | (2-CF₃, 4-SCH₃-phenyl) | m.p. 70–85° C. |
| a-147 | CH₃ | —SO₂—C₆H₄—CH₃ (p) | (2-SO₂CH₃, 3-CH₃, 4-Cl-phenyl) | |
| a-148 | CH₃ | —CH(CH₃)—O—C₆H₅ | (2-SO₂CH₃, 4-CF₃-phenyl) | m.p. 152–153° C. |
| a-149 | CH₃ | —CH₂CH=CH—C₆H₅ | (2-SO₂CH₃, 4-CF₃-phenyl) | Viscous |
| a-150 | CH₃ | —CH₂—C₆H₅ | (2-SCH₃, 3-Cl, 4-Cl-phenyl) | Viscous |

TABLE 4a-continued
(Ia)
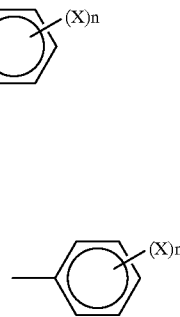
| Compound No. | R₁ | R₂ | | Physical properties |
|---|---|---|---|---|
| a-151 | CH₃ | —CH₂—C₆H₅ | 2,3-Cl₂-6-SOCH₃-C₆H₂ | Viscous |
| a-152 | CH₃ | —CH₂—C₆H₅ | 2,3-Cl₂-6-SO₂CH₃-C₆H₂ | m.p. 157–160° C. |
| a-153 | CH₃ | —SO₂C₃H₇(n) | 2,3-Cl₂-6-SCH₃-C₆H₂ | m.p. 82–85° C. |
| a-154 | CH₃ | —SO₂C₃H₇(n) | 2,3-Cl₂-6-SOCH₃-C₆H₂ | Viscous |
| a-155 | CH₃ | —SO₂C₃H₇(n) | 2,3-Cl₂-6-SO₂CH₃-C₆H₂ | m.p. 165–169° C. |
| a-156 | CH₃ | H | 2,3-Cl₂-6-SCH₃-C₆H₂ | Viscous |
| a-157 | CH₃ | 2,4-(NO₂)₂-C₆H₃ | 2,3-Cl₂-6-SCH₃-C₆H₂ | Viscous |

TABLE 4a-continued
(Ia)
| Compound No. | R₁ | R₂ | | Physical properties |
|---|---|---|---|---|
| a-158 | CH₃ | 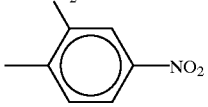 | 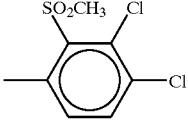 | m.p. 120–130° C. |
| a-159 | CH₃ | 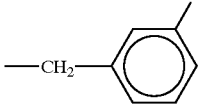 | 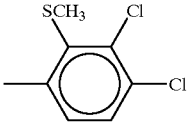 | Viscous |
| a-160 | CH₃ | 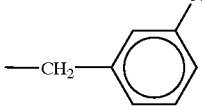 | 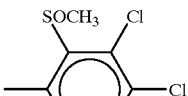 | m.p. 177–178° C. |
| a-161 | CH₃ | 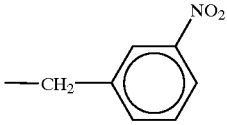 | 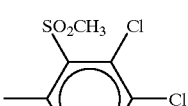 | m.p. 173–175° C. |
| a-162 | CH₃ | 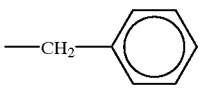 | 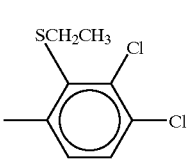 | Viscous |
| a-163 | CH₃ | 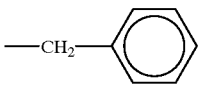 | 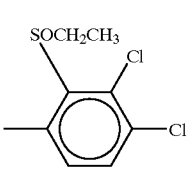 | Viscous |
| a-164 | CH₃ | 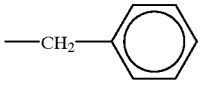 | 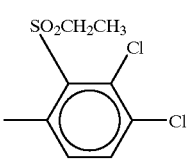 | m.p. 65–75° C. |

TABLE 4a-continued
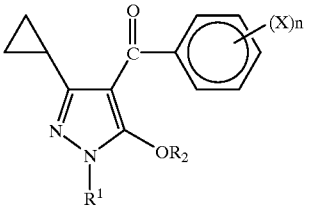
(Ia)
| Compound No. | R₁ | R₂ | | Physical properties |
|---|---|---|---|---|
| a-165 | CH₃ | H | 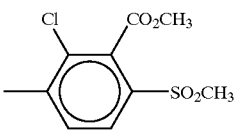 | m.p. 208° C. (decomposition) |
| a-166 | CH₃ | 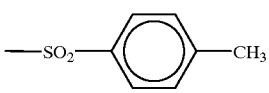 | 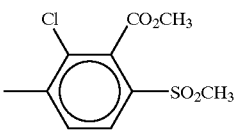 | m.p. 144–147° C. |
| a-167 | CH₃ | 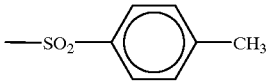 | 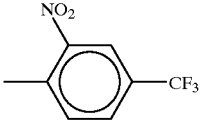 | m.p. 120–141° C. |
| a-168 | CH₃ | —CH₂CO—C(CH₃)₃ | 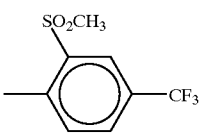 | m.p. 140–144° C. |
| a-169 | CH₃ | 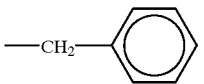 | 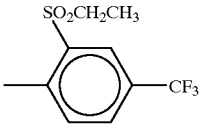 | m.p. 119–122° C. |
| a-170 | CH₃ | —CH₂C≡CH | 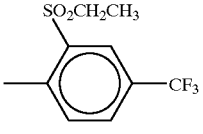 | Oily |
| a-171 | CH₃ | 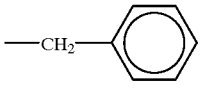 | 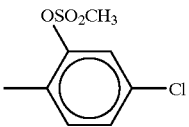 | Viscous |

TABLE 4a-continued
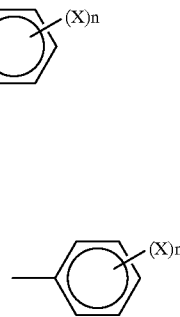
(Ia)
| Compound No. | R₁ | R₂ | | Physical properties |
|---|---|---|---|---|
| a-172 | CH₃ | H | 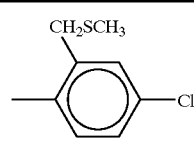 | Oily |
| a-173 | CH₃ | —CH₂CN | 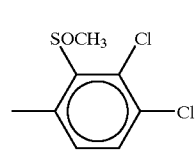 | Viscous |
| a-174 | CH₃ | —CH₂CN | 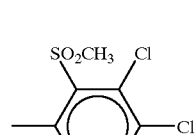 | Viscous |
| a-175 | CH₃ | 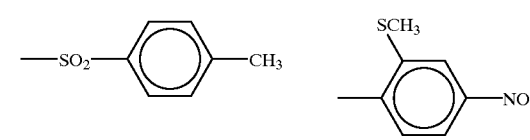 | 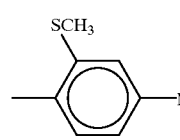 | m.p. 153–156° C. |
| a-176 | CH₃ | 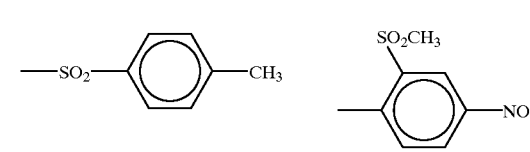 | 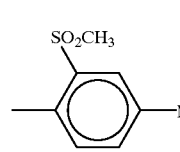 | Viscous |
| a-177 | CH₃ | 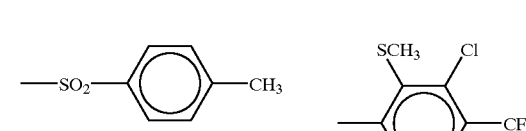 | 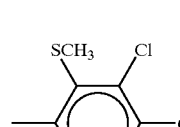 | Viscous |
| a-178 | CH₃ | 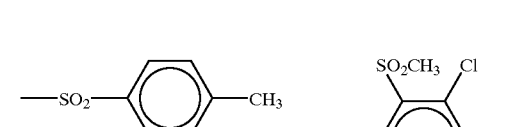 | 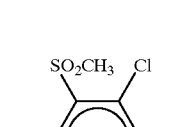 | Viscous |

TABLE 4a-continued (Ia)

| Compound No. | R₁ | R₂ | | Physical properties |
|---|---|---|---|---|
| a-179 | CH₃ | —SO₂C₃H₇(n) | (2-SO₂CH₃, 3-Cl, 6-CF₃ phenyl) | m.p. 140–144° C. |
| a-180 | CH₃ | —CH₂—Ph | (2-CH₂SCH₃, 4-Cl phenyl) | Viscous |
| a-181 | CH₃ | —CH₂—Ph | (2-CH₂SOCH₃, 4-Cl phenyl) | Viscous |
| a-182 | CH₃ | —CH₂—Ph | (2-CH₂SO₂CH₃, 4-Cl phenyl) | m.p. 55–62° C. |
| a-183 | CH₃ | H | (2-SCH₃, 3-Cl, 5-Cl phenyl) | Viscous |
| a-184 | CH₃ | —CH₂—Ph | (2-SCH₃, 3-Cl, 5-Cl phenyl) | Viscous |

TABLE 4a-continued
(Ia)
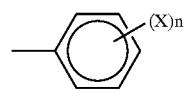
| Compound No. | R₁ | R₂ | | Physical properties |
|---|---|---|---|---|
| a-185 | CH₃ | —CH₂—⌬ | SOCH₃, Cl, Cl (substituted phenyl) | m.p. 154–155° C. |
| a-186 | CH₃ | —CH₂—⌬ | SO₂CH₃, Cl, Cl (substituted phenyl) | m.p. 165–167° C. |
| a-187 | CH₃ | H | N(CH₃)SO₂CH₃, Cl (substituted phenyl) | m.p. 50–58° C. |
| a-188 | CH₃ | —SO₂C₃H₇(n) | N(CH₃)SO₂CH₃, Cl (substituted phenyl) | m.p. 181–184° C. |
| a-189 | CH₃ | —SO₂—⌬—CH₃ | N(CH₃)SO₂CH₃, Cl (substituted phenyl) | m.p. 70–73° C. |
| a-190 | CH₃ | —CH₂C≡CH | SCH₃, Cl, Cl (substituted phenyl) | Viscous |

TABLE 4a-continued
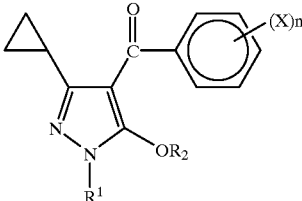
(Ia)
| Compound No. | R₁ | R₂ | | Physical properties |
|---|---|---|---|---|
| a-191 | $CH_3$ | —$CH_2C\equiv CH$ | 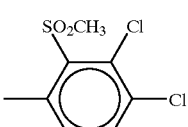 | m.p. 40–50° C. |
| a-192 | $CH_3$ | H | 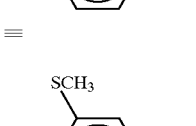 | Viscous |
| a-193 | $CH_3$ | —$CH_2$—Ph | 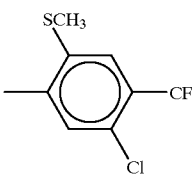 | m.p. 107–110° C. |
| a-194 | $CH_3$ | —$CH_2$—Ph | 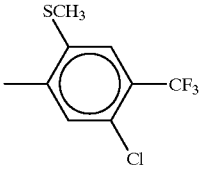 | m.p. 48–52° C. |
| a-195 | $CH_3$ | —$CH_2$—Ph | 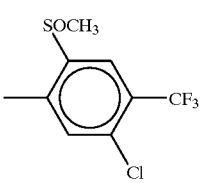 | m.p. 140–148° C. |
| a-196 | $CH_3$ | H | 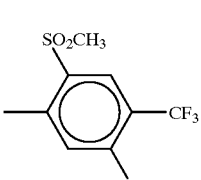 | m.p. 115–130° C. |

TABLE 4a-continued
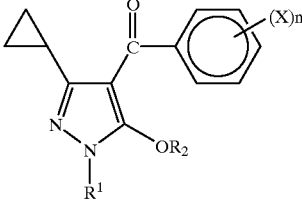
(Ia)
| Compound No. | R₁ | R₂ | | Physical properties |
|---|---|---|---|---|
| a-197 | CH₃ | 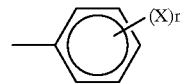 | 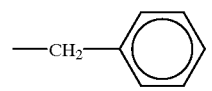 | m.p. 79–93° C. |
| a-198 | CH₃ | 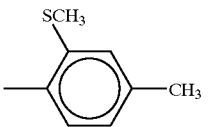 | 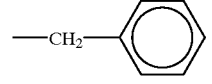 | m.p. 114–125° C. |
| a-199 | CH₃ | 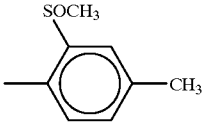 | 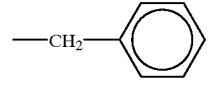 | m.p. 143–146° C. |
| a-200 | CH₃ | 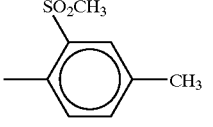 | 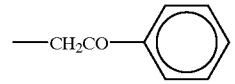 | m.p. 173–178° C. |
| a-201 | CH₃ | H | 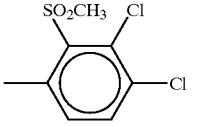 | m.p. 155–156° C. |
| a-202 | CH₃ | 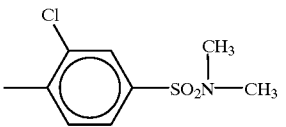 | 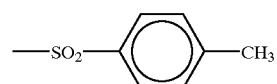 | m.p. 150–151° C. |
| a-203 | CH₃ | —SO₂CH₂CH(CH₃)₂ | 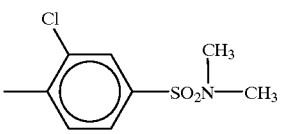 | m.p. 183–188° C. |

TABLE 4a-continued
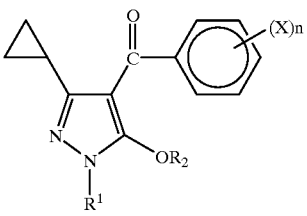
(Ia)
| Compound No. | R₁ | R₂ | | Physical properties |
|---|---|---|---|---|
| a-204 | CH₃ | —CH₂CO—⌬ | SOCH₃, Cl, Cl (phenyl) | Viscous |
| a-205 | CH₃ | (tetrafluoro-CF₃ pyridyl) | SCH₃, Cl, Cl (phenyl) | m.p. 111–126° C. |
| a-206 | CH₃ | —CH₂C≡CH | SOCH₂CH₃, CF₃ (phenyl) | Oily |
| a-207 | CH₃ | —SO₂C₃H₇(n) | SOCH₂CH₃, CF₃ (phenyl) | Viscous |
| a-208 | CH₃ | —SO₂C₃H₇(n) | SOCH₃, CF₃ (phenyl) | m.p. 134–135° C. |
| a-209 | CH₃ | —CH₂C≡CH | SOCH₃, CF₃ (phenyl) | Viscous |
| a-210 | CH₃ | —CH₂—⌬ | SOCH₃, CF₃ (phenyl) | Viscous |

TABLE 4a-continued
(Ia)
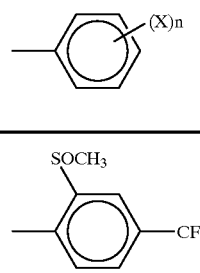
| Compound No. | R₁ | R₂ | | Physical properties |
|---|---|---|---|---|
| a-211 | CH₃ | H | 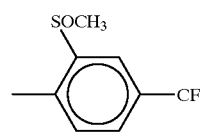 | m.p. 122–138° C. |
| a-212 | CH₃ | —CH₂CN | 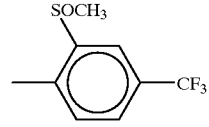 | Viscous |
| a-213 | CH₃ | —CH₂C(Cl)=CH₂ | 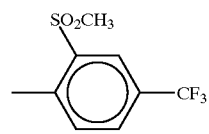 | m.p. 108–111° C. |
| a-214 | CH₃ | —SO₂(CH₂)₃Cl | 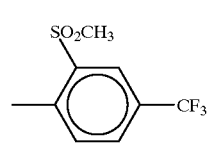 | m.p. 113–118° C. |
| a-215 | CH₃ | —CH₂-C₆H₅ | 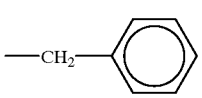 | m.p. 50–60° C. |
| a-216 | CH₃ | —CO(CH₂)₃Cl | 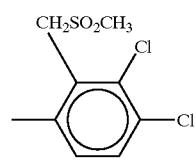 | m.p. 133–135° C. |
| a-217 | CH₃ | —CH₂CH=CH₂ | 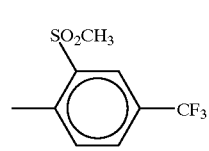 | Viscous |

TABLE 4a-continued
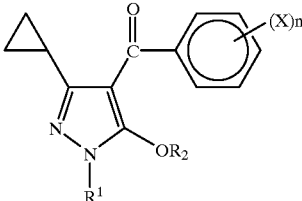
(Ia)
| Compound No. | R₁ | R₂ | | Physical properties |
|---|---|---|---|---|
| a-218 | CH₃ | —CH₂CN | 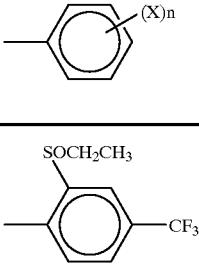 | Viscous |
| a-219 | CH₃ | —CH₂—C₆H₅ | 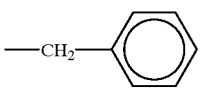 | Viscous |
| a-220 | CH₃ | —SO₃CH₃ | 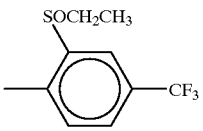 | m.p. 125–130° C. |
| a-221 | CH₃ | —CO₂CH₃ | 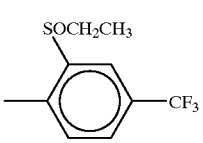 | Viscous |
| a-222 | CH₃ | H | 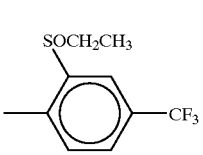 | m.p. 153–156° C. |
| a-223 | CH₃ | —CH₂CO₂CH₂CH₃ | 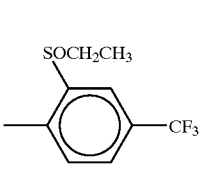 | Viscous |
| a-224 | CH₃ | H | 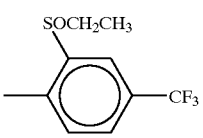 | |

TABLE 4a-continued
(Ia)
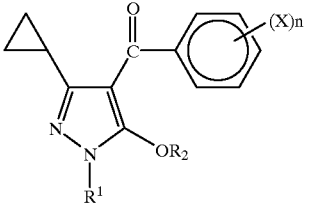
| Compound No. | R₁ | R₂ | | Physical properties |
|---|---|---|---|---|
| a-225 | CH₃ | H | 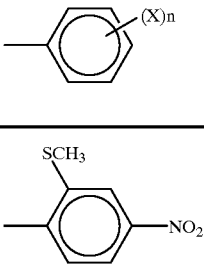 | Viscous |
| a-226 | CH₃ | —SO₂C₃H₇(n) | 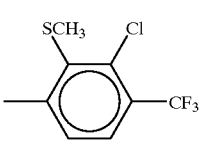 | Viscous |
| a-227 | CH₃ | H | 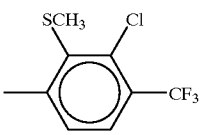 | Oily |
| a-228 | CH₃ | —CH₂CH=CHCl | 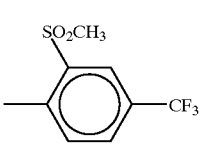 | m.p. 100–103° C. |
| a-229 | CH₃ | —CH₂C(CH₃)=CH₂ | 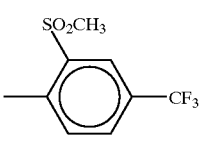 | m.p. 122–125° C. |
| a-230 | CH₃ | —CH₂C(Br)=CH₂ | 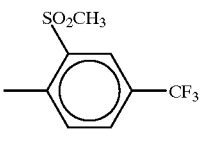 | Oily |
| a-231 | CH₃ | —CH₂CH=C(CH₃)₂ | 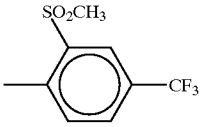 | |

TABLE 4a-continued
(Ia)
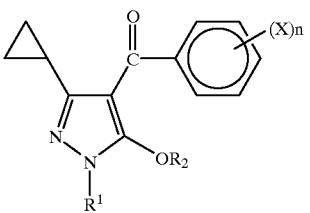
| Compound No. | R₁ | R₂ | | Physical properties |
|---|---|---|---|---|
| a-232 | $CH_3$ | —$CH_2CH$=$C(Cl)_2$ |  | m.p. 142–145° C. |
| a-233 | $CH_3$ | —$CH_2CH$=$CHCH_3$ | 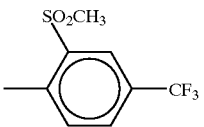 | m.p. 101–106° C. |
| a-234 | $CH_3$ | —CHCH=$CH_2$<br>    |<br>   $CH_3$ | 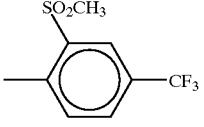 | Oily |
| a-235 | $CH_3$ | —$CH_2CON(CH_3)_2$ | 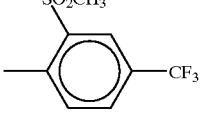 | |
| a-236 | $CH_2CH_3$ | —$CH_2C$=$CH_2$<br>    |<br>   Cl | 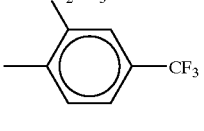 | |
| a-237 | $CH_2CH_3$ | —$CH_2C$=$CH_2$<br>    |<br>   $CH_3$ | 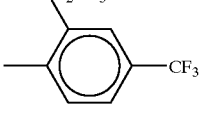 | |
| a-238 | $CH_3$ | —$CH_2C$=$CH_2$<br>    |<br>   $CH_3$ | 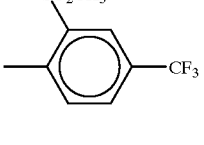 | |

TABLE 4a-continued (Ia)

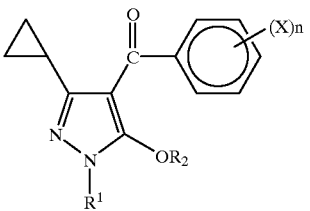

| Compound No. | R₁ | R₂ | | Physical properties |
|---|---|---|---|---|
| a-239 | $CH_3$ | $-CH_2\underset{Br}{C}=CH_2$ | $SO_2CH_2CH_3$ / $CF_3$ substituted phenyl | m.p. 124–126° C. |
| a-240 | $CH_3$ | $-CH_2CH=C(CH_3)_2$ | $SO_2CH_2CH_3$ / $CF_3$ substituted phenyl | |
| a-241 | $CH_3$ | $-\underset{CH_3}{CHCH}=CH_2$ | $SO_2CH_2CH_3$ / $CF_3$ substituted phenyl | Viscous |
| a-242 | $CH_3$ | $-SO_2CH_2CH_3$ | $SO_2CH_2CH_3$ / $CF_3$ substituted phenyl | |
| a-243 | $CH_3$ | $-SO_2C_4H_9(n)$ | $SO_2CH_2CH_3$ / $CF_3$ substituted phenyl | |
| a-244 | $CH_3$ | H | $N(CH_3)SO_2CH_3$ / $CF_3$ substituted phenyl | m.p. 60–65° C. |
| a-245 | $CH_3$ | $-SO_2C_3H_7(n)$ | $N(CH_3)SO_2CH_3$ / $CF_3$ substituted phenyl | |

TABLE 4a-continued (Ia)

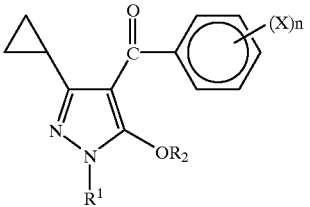

| Compound No. | R₁ | R₂ | | Physical properties |
|---|---|---|---|---|
| a-246 | CH₃ | —CH₂C(Cl)=CH₂ | 2-methyl-5-CF₃-phenyl with N(CH₃)SO₂CH₃ at position 2' | |
| a-247 | CH₃ | —CH₂C(Cl)=CH₂ | 2-methyl-5-CF₃-phenyl with SCH₃ | |
| a-248 | CH₃ | —CH₂C(CH₃)=C(CH₃)₂ | 2-methyl-5-CF₃-phenyl with SO₂CH₃ | |
| a-249 | CH₃ | —CH₂CH=CH₂ | 2-methyl-5-CF₃-phenyl with SO₂CH₂CH₃ | Viscous |
| a-250 | CH₃ | —CH₂CN | 2-methyl-5-CF₃-phenyl with SO₂CH₂CH₃ | Viscous |
| a-251 | CH₃ | —CH₂C(Cl)=CH₂ | 2-methyl-5-CF₃-phenyl with SOCH₂CH₃ | Viscous |
| a-252 | CH₃ | —CH₂CH=CHCl | 2-methyl-5-CF₃-phenyl with SOCH₂CH₃ | Viscous |

TABLE 4a-continued
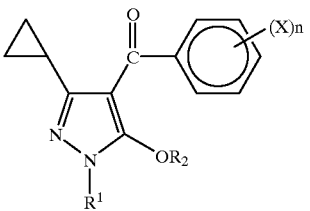
(Ia)
| Compound No. | R₁ | R₂ | | Physical properties |
|---|---|---|---|---|
| a-253 | CH₃ | —CH₂CH=CHCl | 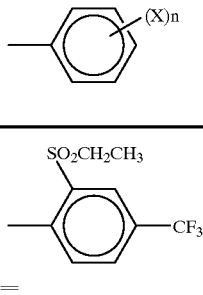 | Viscous |
| a-254 | CH₃ | —CH₂C(Cl)=CH₂ | 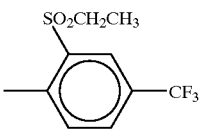 | m.p. 120–125° C. |
| a-255 | CH₃ | —CH₂CH=CHCH₃ | 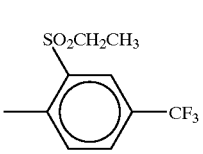 | m.p. 97–105° C. |
| a-256 | CH₃ | —CH₂CH=CHCH₃ | 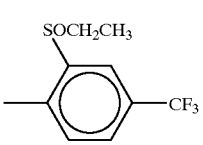 | m.p. 116–117° C. |
| a-257 | CH₃ | —SO₂CH₂CH₃ | 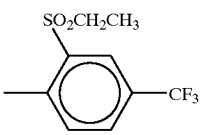 | Viscous |
| a-258 | CH₃ | —SO₃CH₃ | 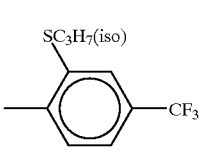 | m.p. 164–165° C. |
| a-259 | CH₃ | —CH₂CO₂CH₂CH₃ | 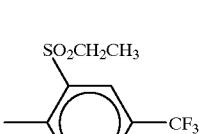 | Viscous |

TABLE 4a-continued
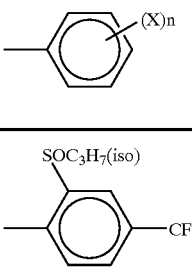
(Ia)
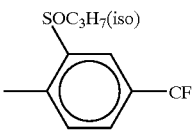
| Compound No. | $R_1$ | $R_2$ | | Physical properties |
|---|---|---|---|---|
| a-260 | $CH_3$ | $-SO_2CH_2CH_3$ | 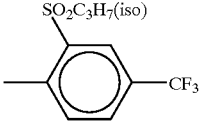 | m.p. 112–115° C. |
| a-261 | $CH_3$ | $-SO_2CH_2CH_3$ | 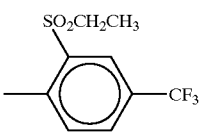 | Viscous |
| a-262 | $CH_3$ | $-CH_2CCH_2COCH_2CH_3$<br>$\phantom{-CH_2C}\|\phantom{CH_2C}\|$<br>$\phantom{-CH_2C}O\phantom{CH_2}O$ | 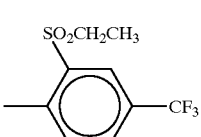 | Viscous |
| a-263 | $CH_3$ | $-CH_2CON(C_2H_5)_2$ | 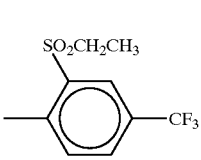 | Viscous |
| a-264 | $CH_3$ | $-CH_2CHCH_2Cl$<br>$\phantom{-CH_2}\|$<br>$\phantom{-CH_2}CH_3$ | 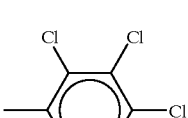 | m.p. 123–125° C. |
| a-265 | $CH_3$ | $-SO_2C_3H_7(n)$ | 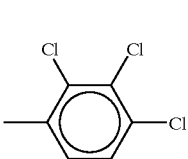 | |
| a-266 | $CH_3$ | $-SO_2C_3H_7(n)$ |  | |

TABLE 4a-continued
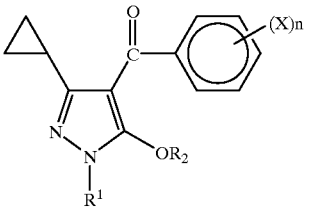
(Ia)
| Compound No. | R₁ | R₂ | | Physical properties |
|---|---|---|---|---|
| a-267 | $CH_3$ | —$CH_2CH_2Cl$ | 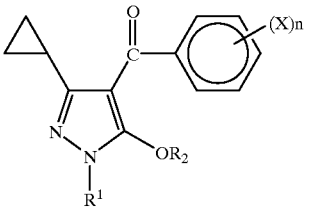 | |
| a-268 | $CH_3$ | —$CH_2CH_2Cl$ |  | |
| a-269 | $CH_3$ | 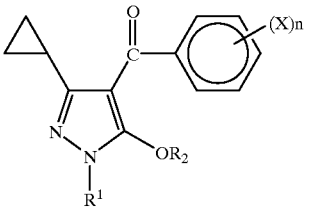 |  | |
| a-270 | $CH_3$ | 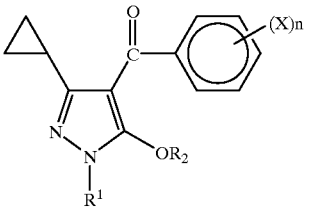 |  | m.p. 67~72° C. |
| a-271 | $CH_3$ | —$CH_2CH{=}C(Cl)_2$ | 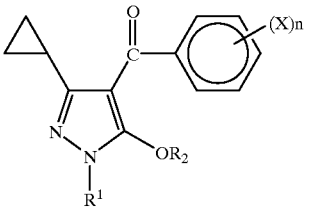 | Viscous |

TABLE 4b

(I)

| Comp. No. | R₁ | R₂ | (Z)₁ / cyclopropyl | (X)n / phenyl | Physical properties |
|---|---|---|---|---|---|
| b-1 | $CH_3$ |  | 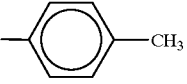 | 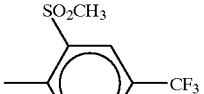 | m.p. 46–56° C. |
| b-2 | $CH_3$ |  |  |  | Viscous |
| b-3 | $CH_3$ | 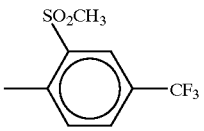 |  |  | |
| b-4 | $CH_3$ |  | $-SO_2C_3H_7(n)$ | 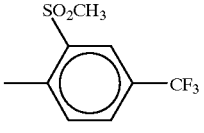 | |
| b-5 | $CH_3$ |  |  |  | |
| b-6 | $CH_3$ | 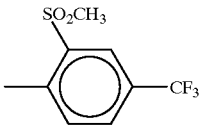 | H |  | |

Now, the Test Examples of the present invention will be described.

TEST EXAMPLE 1

Upland field soil was put into a 1/150,000 ha pot, and seeds of various plants were sown. Then, when the plants reached predetermined leaf stages (① barnyardgrass (*Echinochloa crus-galli* L.), EC: 1.3–2.6 leaf stage, ② crabgrass (*Digitaria sanquinalis* L.), DS: 1.0–2.5 leaf stage, ③ redroot pigweed (*Amaranthus retroflexus* L.), AR: 0.1–1.2 leaf stage, ④ prickly sida (*Sida spinosa* L.), SS: 0.1–1.2 leaf stage, ⑤ tall morningglory (*Pharbitis purpurea* L.), PP: 0.3–1.3 leaf stage, ⑥ common cocklebur (*Xanthium strumarium* L.), XS: 0.1–1.8 leaf stage, ⑦ rice (*Oryza sativa* L.), OS: 1.0–2.5 leaf stage, ⑧ wheat (Triticum spp.), TR: 2.2–2.9 leaf stage, ⑨ corn (*Zea mays* L.), ZM: 1.8–3.5 leaf stage, ⑩ soybean (*Glycine max* Merr.), GM: primary leaf—0.3 leaf stage), a wettable powder having the compound of the present invention formulated in accordance with a usual formulation method, was weighed so that the active ingredient would be a predetermined amount, and diluted with water in an amount of 500 l/ha. To the diluted solution, 0.1% (v/v) of an agricultural spreader was added. The herbicide thus adjusted was applied by a small size spray for foliage treatment. On the 18th to 30th days after the application of the herbicide, the growth of the respective plants was visually observed, and the herbicidal effects were evaluated by the growth-controlling degrees (%) ranging from 0 (equivalent to the non-treated area) to 100 (complete kill), whereby the results shown in Table 5, were obtained. Compound Nos. in Table 5 correspond to Compound Nos. in Table 4a and 4b given hereinbefore.

TABLE 5

| Comp. No. | Dose of active ingredient (g/ha) | Growth-controlling degree (%) | | | | | | | | | | Evaluation day |
|---|---|---|---|---|---|---|---|---|---|---|---|---|
| | | EC | DS | AR | SS | PP | XS | OS | TR | ZM | GM | |
| a-3 | 500 | 0 | 0 | 70 | 60 | 60 | 70 | 40 | 0 | 0 | 0 | 23 |
| a-5 | 500 | 30 | 40 | 70 | 0 | 60 | 60 | 50 | 10 | 0 | 10 | 18 |
| a-11 | 63 | 40 | 20 | 90 | 20 | 80 | 80 | 50 | 0 | 0 | 50 | |
| | 125 | 70 | 40 | 90 | 20 | 80 | 100 | 80 | 0 | 0 | 70 | 22 |
| | 500 | 90 | 50 | 100 | 50 | 100 | 100 | 100 | 0 | 0 | 50 | |
| a-12 | 63 | 80 | 40 | 90 | 30 | 80 | 95 | 80 | 0 | 20 | 70 | |
| | 125 | 80 | 70 | 80 | 20 | 90 | 80 | 90 | 0 | 0 | 70 | 18 |
| | 500 | 90 | 80 | 90 | 60 | 90 | 80 | 100 | 0 | 0 | 80 | |
| a-13 | 500 | 80 | 60 | 90 | 60 | 80 | 100 | 90 | 0 | 0 | 60 | 18 |
| a-24 | 500 | 40 | 50 | 80 | 10 | 60 | 80 | 50 | — | 10 | 30 | 18 |
| a-25 | 500 | 70 | 90 | 80 | 10 | 70 | 90 | 50 | — | 30 | 60 | 18 |
| a-27 | 500 | 60 | 20 | 100 | 20 | 80 | 80 | 50 | 0 | 0 | 40 | 20 |
| a-39 | 63 | 70 | 30 | 80 | 20 | 60 | 80 | 50 | 0 | 10 | 60 | |
| | 125 | 80 | 60 | 90 | 30 | 60 | 100 | 70 | 0 | 10 | 60 | 20 |
| | 500 | 90 | 80 | 90 | 30 | 70 | 100 | 70 | 10 | 20 | 80 | |
| a-40 | 63 | 90 | 30 | 90 | 10 | 90 | 80 | 90 | — | 30 | 50 | |
| | 125 | 90 | 40 | 90 | 30 | 90 | 90 | 100 | — | 50 | 70 | 18 |
| | 500 | 100 | 90 | 100 | 60 | 90 | 100 | 100 | — | 70 | 70 | |
| a-41 | 63 | 90 | 20 | 90 | 20 | 90 | 70 | 90 | — | 0 | 50 | |
| | 125 | 90 | 40 | 90 | 20 | 90 | 80 | 90 | — | 0 | 10 | 18 |
| | 500 | 100 | 90 | 100 | 40 | 100 | 100 | 100 | — | 20 | 90 | |
| a-42 | 500 | 60 | 40 | 100 | 30 | 70 | 80 | 50 | 10 | 20 | 50 | 20 |
| a-43 | 125 | 50 | 30 | 90 | 20 | 60 | 80 | 40 | 0 | 20 | 50 | 20 |
| | 500 | 70 | 80 | 100 | 30 | 80 | 100 | 70 | 20 | 20 | 70 | |
| a-44 | 63 | 80 | 50 | 80 | 20 | 60 | 80 | 60 | — | 0 | 60 | |
| | 125 | 90 | 70 | 80 | 20 | 70 | 90 | 80 | — | 20 | 70 | 18 |
| | 500 | 90 | 90 | 90 | 30 | 90 | 100 | 80 | — | 20 | 80 | |
| a-45 | 125 | 40 | 30 | 80 | 20 | 80 | 60 | 10 | 10 | 40 | 50 | 20 |
| | 500 | 70 | 50 | 90 | 20 | 80 | 100 | 20 | 20 | 20 | 50 | |
| a-47 | 125 | 40 | 40 | 90 | 30 | 60 | 80 | 20 | — | 0 | 0 | 18 |
| | 500 | 80 | 50 | 100 | 60 | 80 | 80 | 70 | — | 30 | 40 | |
| a-48 | 63 | 80 | 40 | 90 | 10 | 40 | 70 | 50 | — | 0 | 50 | |
| | 125 | 90 | 60 | 90 | 30 | 70 | 100 | 80 | — | 20 | 60 | 18 |
| | 500 | 100 | 80 | 100 | 60 | 90 | 100 | 80 | — | 40 | 70 | |
| a-49 | 125 | 80 | 40 | 100 | 30 | 70 | 90 | 60 | 10 | 20 | 60 | 20 |
| | 500 | 80 | 70 | 100 | 30 | 80 | 90 | 80 | 20 | 20 | 60 | |
| a-51 | 125 | 90 | 60 | 80 | 10 | 80 | 80 | 70 | — | 0 | 70 | 19 |
| | 500 | 90 | 90 | 100 | 30 | 90 | 90 | 80 | — | 10 | 70 | |
| a-52 | 63 | 90 | 60 | 80 | 20 | 70 | 80 | 60 | — | 20 | 80 | 18 |
| | 125 | 90 | 70 | 80 | 30 | 80 | 90 | 70 | — | 30 | 90 | |
| | 500 | 90 | 90 | 90 | 50 | 90 | 100 | 80 | — | 40 | 90 | |
| a-53 | 63 | 76 | 10 | 90 | 0 | 70 | 80 | 50 | — | 0 | 50 | |
| | 125 | 80 | 20 | 90 | 10 | 80 | 90 | 50 | — | 0 | 60 | 18 |
| | 500 | 90 | 90 | 90 | 20 | 90 | 100 | 90 | — | 10 | 70 | |
| a-59 | 500 | 70 | 40 | 80 | 0 | 80 | 90 | 30 | 0 | 10 | 60 | 20 |
| a-60 | 63 | 90 | 50 | 80 | 10 | 90 | 90 | 60 | — | 0 | 100 | |
| | 125 | 90 | 80 | 90 | 20 | 100 | 100 | 70 | — | 20 | 90 | 19 |
| | 500 | 90 | 90 | 100 | 30 | 100 | 100 | 90 | — | 60 | 90 | |
| a-69 | 500 | 40 | 40 | 90 | 50 | 10 | 100 | 60 | 0 | 10 | 40 | 20 |
| a-72 | 125 | 70 | 20 | 80 | 0 | 60 | 90 | 50 | — | 0 | 40 | 19 |
| | 500 | 100 | 30 | 90 | 0 | 70 | 100 | 80 | — | 0 | 60 | |
| a-73 | 500 | 60 | 30 | 90 | 40 | 70 | 80 | 10 | — | 30 | 50 | 18 |
| a-76 | 63 | 70 | 30 | 90 | 0 | 80 | 90 | 70 | 0 | 10 | 70 | |
| | 125 | 80 | 60 | 90 | 20 | 80 | 90 | 70 | 10 | 20 | 70 | 20 |
| | 500 | 90 | 90 | 100 | 40 | 100 | 100 | 70 | 20 | 40 | 80 | |
| a-77 | 125 | 90 | 30 | 80 | 10 | 70 | 70 | 50 | — | 10 | 60 | 18 |
| | 500 | 90 | 60 | 90 | 30 | 70 | 90 | 90 | — | 30 | 70 | |
| a-78 | 63 | 80 | 40 | 70 | 20 | 60 | 80 | 40 | — | 10 | 60 | |
| | 125 | 80 | 40 | 90 | 20 | 90 | 90 | 60 | — | 20 | 70 | 18 |
| | 500 | 100 | 50 | 100 | 40 | 90 | 100 | 60 | — | 50 | 70 | |

TABLE 5-continued

| Comp. No. | Dose of active ingre-dient (g/ha) | Growth-controlling degree (%) | | | | | | | | | Evalu-ation day |
|---|---|---|---|---|---|---|---|---|---|---|---|
| | | EC | DS | AR | SS | PP | XS | OS | TR | ZM | GM | |
| a-79 | 500 | 60 | 30 | 100 | 50 | 80 | 90 | 30 | — | 0 | 70 | 18 |
| a-80 | 500 | 80 | 90 | 80 | 20 | 60 | 80 | 80 | — | 60 | 10 | 19 |
| a-81 | 125 | 60 | 60 | 90 | 10 | 90 | 40 | 10 | — | 0 | 30 | 19 |
| | 500 | 90 | 90 | 90 | 30 | 90 | — | 40 | — | 10 | 50 | |
| a-82 | 125 | 40 | 30 | 80 | 20 | 60 | 100 | 60 | — | 0 | 60 | 19 |
| | 500 | 80 | 30 | 90 | 20 | 90 | 100 | 80 | — | 10 | 70 | |
| a-83 | 63 | 50 | 60 | 80 | 30 | 70 | 100 | 60 | — | 0 | 10 | |
| | 125 | 60 | 70 | 80 | 40 | 80 | 100 | 60 | — | 10 | 20 | 18 |
| | 500 | 90 | 90 | 90 | 40 | 90 | 90 | 80 | — | 30 | 70 | |
| a-84 | 63 | 70 | 30 | 70 | 30 | 40 | 100 | 30 | — | 0 | 50 | |
| | 125 | 80 | 50 | 80 | 20 | 60 | 100 | 60 | — | 0 | 60 | 18 |
| | 500 | 90 | 90 | 90 | 50 | 90 | 90 | 100 | — | 20 | 70 | |
| a-87 | 125 | 80 | 20 | 90 | 10 | 70 | 100 | 60 | — | 10 | 60 | 19 |
| | 500 | 100 | 70 | 95 | 10 | 100 | — | 80 | — | 0 | 95 | |
| a-88 | 63 | 90 | 60 | 80 | 30 | 80 | 90 | 70 | — | 10 | 70 | |
| | 125 | 90 | 80 | 90 | 60 | 80 | 90 | 70 | — | 20 | 80 | 18 |
| | 500 | 100 | 90 | 90 | 60 | 90 | 100 | 80 | — | 60 | 90 | |
| a-89 | 63 | 90 | 90 | 90 | 30 | 90 | 100 | 100 | — | 10 | 90 | |
| | 125 | 90 | 90 | 90 | 30 | 90 | 100 | 90 | — | 20 | 100 | 19 |
| | 500 | 100 | 100 | 100 | 60 | 100 | 100 | 100 | — | 80 | 100 | |
| a-90 | 125 | 80 | 90 | 70 | 0 | 60 | 80 | 60 | — | 40 | 10 | 19 |
| | 500 | 90 | 100 | 80 | 10 | 70 | 100 | 80 | — | 80 | 70 | |
| a-92 | 500 | 80 | 90 | 90 | 20 | 90 | — | 50 | — | 0 | 20 | 19 |
| a-93 | 125 | 60 | 40 | 95 | 0 | 60 | 100 | 10 | — | 0 | 70 | 19 |
| | 500 | 80 | 50 | 100 | 20 | 100 | — | 70 | — | 0 | 100 | |
| a-94 | 63 | 90 | 90 | 80 | 10 | 90 | 80 | 70 | — | 0 | 60 | |
| | 125 | 100 | 90 | 90 | — | 100 | 100 | 90 | — | 10 | 70 | 19 |
| | 500 | 90 | 90 | 90 | 20 | 100 | 100 | 90 | — | 20 | 70 | |
| a-95 | 63 | 100 | 70 | 100 | 10 | 80 | 90 | 90 | — | 20 | 95 | |
| | 125 | 100 | 90 | 100 | 10 | 95 | 100 | 100 | — | 35 | 95 | 19 |
| | 500 | 100 | 100 | 100 | 40 | 100 | — | 100 | — | 70 | 100 | |
| a-96 | 125 | 80 | 70 | 80 | 20 | 80 | 90 | 60 | 10 | 40 | 80 | 20 |
| | 500 | 100 | 100 | 100 | 30 | 100 | 100 | 70 | 20 | 60 | 90 | |
| a-97 | 63 | 90 | 30 | 90 | 0 | 40 | 50 | 10 | — | 0 | 20 | |
| | 125 | 80 | 40 | 80 | 10 | 50 | 70 | 30 | — | 0 | 30 | 18 |
| | 500 | 90 | 90 | 90 | 20 | 70 | 80 | 50 | — | 20 | 60 | |
| a-98 | 63 | 90 | 30 | 90 | 0 | 60 | 70 | 30 | — | 0 | 40 | |
| | 125 | 90 | 40 | 100 | 30 | 80 | 70 | 40 | — | 0 | 50 | 18 |
| | 500 | 90 | 90 | 90 | 30 | 90 | 100 | 100 | — | 20 | 60 | |
| a-99 | 63 | 90 | 40 | 100 | 40 | 80 | 80 | 70 | — | 40 | 70 | |
| | 125 | 100 | 60 | 100 | 40 | 90 | 100 | 90 | — | 50 | 70 | 18 |
| | 500 | 100 | 100 | 100 | 70 | 100 | 100 | 100 | — | 80 | 100 | |
| a-100 | 125 | 80 | 40 | 90 | 30 | 80 | 70 | 0 | — | 0 | 50 | 18 |
| | 500 | 90 | 90 | 100 | 40 | 90 | 100 | 50 | — | 10 | 60 | |
| a-101 | 125 | 90 | 30 | 90 | 0 | 30 | 20 | 0 | — | 0 | 50 | 18 |
| | 500 | 90 | 40 | 90 | 30 | 30 | 60 | 0 | — | 20 | 60 | |
| a-102 | 63 | 90 | 40 | 90 | 20 | 10 | 80 | 80 | — | 0 | 100 | |
| | 125 | 95 | 60 | 90 | 30 | 80 | 80 | 100 | — | 10 | 60 | 19 |
| | 500 | 100 | 90 | 100 | 70 | 90 | 80 | 90 | — | 20 | 100 | |
| a-103 | 63 | 90 | 30 | 90 | 40 | 60 | 70 | 50 | — | 0 | 50 | |
| | 125 | 100 | 50 | 60 | 40 | 80 | 100 | 50 | — | 0 | 50 | 19 |
| | 500 | 100 | 90 | 80 | 50 | 100 | 100 | 100 | — | 40 | 70 | |
| a-104 | 125 | 80 | 20 | 90 | 0 | 10 | 0 | 0 | — | 0 | 10 | 19 |
| | 500 | 90 | 20 | 100 | 10 | 10 | 0 | 0 | — | 0 | 20 | |
| a-105 | 63 | 90 | 30 | 100 | 30 | 40 | 20 | 10 | — | 10 | 40 | |
| | 125 | 90 | 40 | 100 | 0 | 60 | 80 | 30 | — | 0 | 50 | 19 |
| | 500 | 100 | 80 | 80 | 30 | 90 | — | 50 | — | 80 | 90 | |
| a-106 | 63 | 10 | 30 | 80 | 50 | 60 | — | 20 | — | 0 | 30 | |
| | 125 | 70 | 70 | 100 | 50 | 90 | 90 | 90 | — | 20 | 40 | 21 |
| | 500 | 90 | 70 | 70 | — | 100 | 50 | 100 | — | 50 | 80 | |
| a-116 | 125 | 50 | 10 | 100 | 30 | 70 | — | 30 | — | 10 | 30 | 24 |
| | 500 | 50 | 50 | 90 | 20 | 90 | — | 20 | — | 0 | 40 | |
| a-118 | 63 | 70 | 30 | 100 | 30 | 70 | 90 | 100 | — | 10 | 70 | |
| | 125 | 80 | 50 | 80 | 30 | 80 | — | 100 | — | 40 | 100 | 21 |
| | 500 | 90 | 80 | 100 | — | 100 | 100 | 100 | — | 60 | 100 | |
| a-120 | 63 | 90 | 50 | 100 | 20 | 50 | 80 | 90 | — | 0 | 70 | |
| | 125 | 100 | 50 | 100 | 50 | 80 | 100 | 100 | — | 0 | 80 | 21 |
| | 500 | 90 | 90 | — | 100 | 60 | 100 | 100 | — | 70 | 100 | |
| a-122 | 63 | 70 | 50 | 100 | 40 | 60 | 90 | 60 | — | 10 | 50 | |
| | 125 | 80 | 90 | 100 | 50 | 70 | 90 | 90 | — | 30 | 60 | 21 |
| | 500 | 90 | 90 | — | — | 50 | 100 | 100 | — | 40 | 70 | |

TABLE 5-continued

| Comp. No. | Dose of active ingredient (g/ha) | Growth-controlling degree (%) | | | | | | | | | Evaluation day |
|---|---|---|---|---|---|---|---|---|---|---|---|
| | | EC | DS | AR | SS | PP | XS | OS | TR | ZM | GM | |
| a-131 | 500 | 80 | 40 | 60 | 30 | 80 | 100 | 50 | — | 30 | 20 | 19 |
| a-132 | 125 | 80 | 70 | 60 | 20 | 90 | 50 | 10 | — | 30 | 0 | 19 |
| | 500 | 90 | 90 | 60 | 20 | 90 | 50 | 40 | — | 70 | 10 | |
| a-133 | 500 | 10 | 30 | 90 | 40 | 70 | 10 | 0 | — | 40 | 30 | 21 |
| a-136 | 125 | 20 | 30 | 90 | 50 | 70 | — | 0 | — | 40 | 40 | 21 |
| | 500 | 100 | 100 | 80 | 30 | 70 | 50 | 0 | — | 100 | 50 | |
| a-137 | 125 | 20 | 30 | 90 | 0 | 100 | — | 0 | — | 40 | 30 | 21 |
| | 500 | 90 | 60 | 100 | 10 | 100 | 80 | 40 | — | 80 | 50 | |
| a-138 | 500 | 100 | 80 | 90 | 70 | 100 | 20 | 0 | — | 90 | 50 | 21 |
| a-139 | 500 | 10 | 50 | 90 | 50 | 70 | 70 | 0 | — | 80 | 50 | 21 |
| a-140 | 63 | 90 | 10 | 100 | 10 | 40 | 70 | 0 | — | 0 | 30 | |
| | 125 | 90 | 30 | 100 | 20 | 80 | 80 | 20 | — | 10 | 40 | 21 |
| | 500 | 100 | 90 | — | 30 | 100 | 80 | 90 | — | 0 | 50 | |
| a-141 | 125 | 80 | 60 | 100 | 30 | 90 | 90 | 90 | — | 20 | 70 | 21 |
| | 500 | 90 | 90 | — | 60 | 100 | 100 | 90 | — | 30 | 80 | |
| a-143 | 500 | 90 | 30 | 50 | 20 | 80 | 100 | 20 | — | 20 | 60 | 18 |
| a-144 | 500 | 50 | 90 | 30 | 40 | 60 | 100 | 50 | — | 0 | 20 | 18 |
| a-146 | 125 | 20 | 30 | 80 | 40 | 80 | 50 | 40 | — | 20 | 40 | 19 |
| | 500 | 60 | 80 | 80 | 40 | 90 | 100 | 60 | — | 30 | 70 | |
| a-148 | 125 | 60 | 10 | 100 | 50 | 70 | 10 | 20 | — | 10 | 10 | 21 |
| | 500 | 90 | 80 | 100 | 50 | 80 | 20 | 20 | — | 40 | 40 | |
| a-149 | 63 | 60 | 20 | 90 | 40 | 80 | — | 0 | — | 10 | 60 | |
| | 125 | 90 | 30 | 80 | 50 | 80 | — | 40 | — | 20 | 70 | 21 |
| | 500 | 100 | 80 | 100 | 70 | 100 | 100 | 100 | — | 60 | 90 | |
| a-150 | 125 | 90 | 70 | 50 | 20 | 80 | — | 40 | — | 100 | 60 | 25 |
| | 500 | 100 | 90 | 70 | 20 | 100 | 70 | 70 | — | 100 | 70 | |
| a-151 | 125 | 100 | 90 | 40 | 30 | 80 | 30 | 20 | — | 50 | 30 | 25 |
| | 500 | 100 | 90 | 100 | 30 | 100 | 80 | 20 | — | 90 | 50 | |
| a-152 | 125 | 100 | 60 | 70 | 10 | 60 | 20 | 10 | — | 60 | 10 | 25 |
| | 500 | 100 | 90 | 90 | 50 | 100 | 100 | 20 | — | 50 | 40 | |
| a-153 | 125 | 60 | 20 | 50 | 10 | 40 | 80 | 10 | — | 0 | 0 | 24 |
| | 500 | 90 | 60 | 60 | 30 | 50 | — | 20 | — | 10 | 20 | |
| a-154 | 500 | 90 | 70 | 70 | 10 | 70 | 60 | 50 | — | 0 | 30 | 25 |
| a-155 | 500 | 60 | 70 | 100 | 10 | 70 | 100 | 20 | — | 0 | 40 | 25 |
| a-156 | 250 | 90 | 70 | 20 | 20 | 70 | — | 20 | — | 10 | 40 | 21 |
| a-158 | 125 | 60 | 40 | 90 | 20 | 70 | 70 | 50 | — | 40 | 50 | 21 |
| | 250 | 70 | 50 | 90 | 20 | 90 | — | 50 | — | 60 | 50 | |
| a-162 | 500 | 60 | 20 | 0 | 10 | 80 | — | 10 | 0 | 10 | 0 | 21 |
| a-164 | 500 | 70 | 70 | 20 | 10 | 90 | — | 10 | 0 | 40 | 50 | 21 |
| a-165 | 63 | 100 | 95 | 100 | 40 | 100 | 50 | 99 | 50 | 50 | 40 | |
| | 125 | 100 | 95 | 100 | 100 | 100 | — | 100 | 50 | 90 | 60 | 30 |
| | 500 | 100 | 100 | 100 | 100 | 100 | — | 100 | 80 | 95 | 100 | |
| a-166 | 63 | 95 | 80 | 100 | 40 | 90 | 20 | 70 | 10 | 40 | 40 | |
| | 125 | 100 | 95 | — | 50 | 100 | 20 | 100 | 50 | 40 | 40 | 30 |
| | 500 | 100 | 100 | 100 | 50 | 100 | — | 100 | 50 | 70 | 50 | |
| a-167 | 125 | 10 | 20 | 100 | 0 | 100 | 90 | 40 | — | 0 | 40 | 21 |
| | 500 | 40 | 30 | 100 | 90 | 100 | 100 | 70 | — | 30 | 100 | |
| a-168 | 63 | 90 | 60 | 100 | 50 | 90 | 90 | 100 | — | 40 | 50 | |
| | 125 | 100 | 70 | 100 | 60 | 100 | — | 100 | — | 70 | 70 | 21 |
| | 500 | 100 | 100 | 100 | 60 | 100 | — | 100 | — | 100 | 100 | |
| a-169 | 63 | 90 | 60 | 100 | 30 | 100 | 10 | 10 | — | 10 | 30 | 21 |
| | 125 | 90 | 70 | 90 | 40 | 100 | 10 | 20 | — | 10 | 60 | |
| a-170 | 63 | 90 | 60 | 80 | 20 | 100 | 70 | 90 | — | 10 | 90 | 21 |
| | 125 | 90 | 80 | 100 | 50 | 100 | 70 | 100 | — | 60 | 100 | |
| a-171 | 500 | 40 | 10 | 40 | 0 | 80 | — | 0 | 0 | 0 | 60 | 21 |
| a-172 | 125 | 60 | 20 | 80 | 30 | 80 | 80 | 80 | 0 | 0 | 50 | 21 |
| | 500 | 100 | 50 | 90 | 60 | 100 | 100 | 0 | 50 | 95 | | |
| a-173 | 125 | 70 | 30 | 30 | 10 | 80 | 30 | 100 | 0 | 0 | 50 | 21 |
| | 500 | 90 | 60 | 40 | 30 | 100 | — | 100 | 0 | 40 | 60 | |

TABLE 5-continued

| Comp. No. | Dose of active ingredient (g/ha) | Growth-controlling degree (%) | | | | | | | | | | Evaluation day |
|---|---|---|---|---|---|---|---|---|---|---|---|---|
| | | EC | DS | AR | SS | PP | XS | OS | TR | ZM | GM | |
| a-174 | 125 | 70 | 40 | 50 | 0 | 80 | 70 | 100 | 0 | 0 | 70 | 21 |
| | 500 | 100 | 60 | 90 | 30 | 100 | — | 80 | 0 | 50 | 80 | |
| a-177 | 500 | 80 | 50 | 30 | 0 | 90 | — | 10 | 0 | 20 | 40 | 21 |
| a-178 | 500 | 60 | 40 | 60 | 0 | 80 | — | 50 | 0 | 0 | 50 | 21 |
| a-179 | 500 | 70 | 70 | 90 | 90 | 70 | — | 50 | 0 | 0 | 80 | 21 |
| a-180 | 125 | 80 | 20 | 50 | 20 | 100 | 50 | 100 | 0 | 0 | 70 | 21 |
| | 500 | 100 | 50 | 90 | 30 | 100 | — | 50 | 0 | 60 | 80 | |
| a-181 | 125 | 70 | 20 | 70 | 10 | 100 | 70 | 50 | 0 | 0 | 70 | 21 |
| | 500 | 100 | 40 | 60 | 20 | 100 | — | 90 | 0 | 40 | 80 | |
| a-182 | 125 | 60 | 20 | 80 | 0 | 100 | 60 | 50 | 0 | 0 | 50 | 21 |
| | 500 | 60 | 60 | 80 | 10 | 100 | — | 50 | 0 | 20 | 90 | |
| a-183 | 500 | 0 | 40 | 10 | 10 | 100 | 100 | 0 | 0 | 10 | 40 | 21 |
| a-184 | 500 | 50 | 20 | 10 | 20 | 100 | — | 0 | 0 | 0 | 40 | 21 |
| a-187 | 500 | 70 | 20 | 100 | 40 | 95 | — | 50 | 0 | 0 | 60 | 21 |
| a-188 | 500 | 50 | 10 | 90 | 40 | 95 | — | 10 | 0 | 0 | 70 | 21 |
| a-189 | 500 | 90 | 10 | 100 | 40 | 95 | — | 90 | 0 | 0 | 70 | 21 |
| a-191 | 125 | 90 | 30 | 90 | 20 | 90 | — | 20 | 0 | 0 | 50 | 21 |
| | 500 | 100 | 50 | 90 | 40 | 90 | — | 40 | 0 | 0 | 50 | |
| a-192 | 500 | 30 | 0 | 30 | 0 | 80 | 90 | 30 | 0 | 10 | 60 | 20 |
| a-194 | 500 | 0 | 30 | 20 | 0 | 100 | 90 | 0 | 0 | 0 | 50 | 22 |
| a-200 | 500 | 70 | 50 | 95 | 20 | 100 | 90 | 20 | 0 | 0 | 40 | 26 |
| a-201 | 500 | 20 | 40 | 90 | 40 | 20 | 70 | 40 | 0 | 0 | 0 | 26 |
| a-203 | 125 | 20 | 60 | 90 | 10 | 80 | 50 | 20 | 0 | 0 | 60 | 22 |
| | 500 | 70 | 80 | 100 | 50 | 100 | 95 | 90 | 0 | 0 | 90 | |
| a-204 | 500 | 70 | 50 | 30 | 0 | 80 | 80 | 20 | 0 | 0 | 50 | 22 |
| a-206 | 125 | 80 | 30 | 30 | 20 | 100 | 100 | 90 | 0 | 0 | 90 | 22 |
| | 500 | 100 | 80 | 100 | 50 | 100 | 100 | 100 | 0 | 70 | 100 | |
| a-207 | 125 | 70 | 20 | 20 | 0 | 100 | 80 | 80 | 6 | 0 | 80 | 22 |
| | 500 | 90 | 60 | 90 | 40 | 100 | 100 | 100 | 0 | 20 | 100 | |
| a-208 | 125 | 30 | 40 | 90 | 10 | 80 | 100 | 50 | 0 | 0 | 50 | 22 |
| | 500 | 70 | 60 | 70 | 40 | 90 | 100 | 95 | 0 | 0 | 60 | |
| a-209 | 500 | 40 | 10 | 30 | 0 | 90 | 80 | 70 | 0 | 0 | 10 | 22 |
| a-210 | 125 | 90 | 60 | 70 | 10 | 90 | 90 | 90 | 0 | 0 | 80 | 27 |
| | 500 | 100 | 90 | 100 | 40 | 100 | 90 | 90 | 0 | 60 | 100 | |
| a-211 | 125 | 40 | 20 | 70 | 0 | 50 | 80 | 10 | 0 | 0 | 40 | 27 |
| | 500 | 80* | 50 | 90 | 20 | 70 | 90 | 70 | 0 | 0 | 50 | |
| a-212 | 125 | 70 | 0 | 40 | 0 | 0 | 70 | 60 | 0 | 0 | 50 | 27 |
| | 500 | 100 | 10 | 70 | 0 | 90 | 80 | 80 | 0 | 0 | 80 | |
| a-213 | 125 | 100 | 80 | 95 | 30 | 100 | 100 | 80 | 0 | 20 | 95 | 26 |
| | 500 | 100 | 100 | 100 | 70 | 100 | 100 | 100 | 0 | 70 | 100 | |
| a-214 | 125 | 60 | 60 | 100 | 20 | 90 | 70 | 100 | 0 | 0 | 50 | 27 |
| | 500 | 100 | 90 | 100 | 70 | 100 | 90 | 100 | 0 | 0 | 70 | |
| a-215 | 500 | 0 | 0 | 90 | 20 | 90 | 80 | 0 | 0 | 0 | 40 | 23 |
| a-216 | 125 | 50 | 70 | 90 | 10 | 70 | 70 | 50 | 0 | 0 | 40 | 23 |
| | 500 | 90 | 90 | 100 | 60 | 80 | 100 | 100 | 0 | 0 | 70 | |
| a-217 | 125 | 60 | 30 | 50 | 10 | 100 | 80 | 70 | 0 | 0 | 70 | 20 |
| | 500 | 30 | 60 | 80 | 20 | 100 | 100 | 100 | 0 | 70 | 100 | |
| a-218 | 125 | 10 | 20 | 10 | 10 | 90 | 70 | 70 | 0 | 0 | 80 | 20 |
| | 500 | 90 | 60 | 50 | 20 | 100 | 80 | 90 | 0 | 40 | 100 | |
| a-219 | 125 | 70 | 30 | 10 | 0 | 100 | 80 | 50 | 0 | 0 | 80 | 20 |
| | 500 | 100 | 70 | 60 | 30 | 100 | 100 | 80 | 0 | 70 | 100 | |
| a-220 | 125 | 10 | 10 | 10 | 0 | 70 | 80 | 10 | 0 | 0 | 40 | 20 |
| | 500 | 70 | 30 | 30 | 20 | 90 | 80 | 60 | 0 | 0 | 40 | |
| a-221 | 125 | 60 | 0 | 0 | 0 | 80 | 80 | 50 | 0 | 0 | 70 | 20 |
| | 500 | 80 | 60 | 40 | 30 | 100 | 100 | 50 | 0 | 0 | 90 | |
| a- | 125 | 30 | 10 | 30 | 10 | 80 | 70 | 20 | 0 | 0 | 40 | 20 |

TABLE 5-continued

| Comp. No. | Dose of active ingredient (g/ha) | Growth-controlling degree (%) | | | | | | | | | | Evaluation day |
|---|---|---|---|---|---|---|---|---|---|---|---|---|
| | | EC | DS | AR | SS | PP | XS | OS | TR | ZM | GM | |
| 222 | 500 | 80 | 50 | 80 | 50 | 90 | 90 | 70 | 0 | 10 | 60 | |
| a-257 | 125 | 70 | 10 | 10 | 0 | 90 | 70 | 20 | 0 | 0 | 50 | 28 |
| | 500 | 90 | 60 | 10 | 10 | 100 | 100 | 30 | 0 | 30 | 100 | |
| a-258 | 125 | 50 | 10 | 30 | 0 | 90 | 70 | 10 | 0 | 0 | 40 | 28 |
| | 500 | 90 | 70 | 80 | 30 | 100 | 100 | 50 | 0 | 0 | 70 | |
| a-259 | 125 | 70 | 70 | 0 | 0 | 80 | 90 | 10 | 0 | 0 | 60 | 28 |
| | 500 | 90 | 100 | 20 | 0 | 90 | 100 | 40 | 0 | 0 | 80 | |
| b-1 | 500 | 80 | 50 | 80 | 20 | 90 | — | 60 | — | 20 | 60 | 19 |
| b-2 | 500 | 90 | 20 | 70 | 20 | 90 | 60 | 60 | — | 0 | 60 | 18 |

TEST EXAMPLE 2

Paddy field soil was put into a 1/1,000,000 ha pot, and seeds of barnyardgrass (*Echinochloa crus-galli* L.) and japanese bulrush (*Scirpus juncoides*) were sown and slightly covered with soil. Then, the pot was left to stand still in a greenhouse in a state where the depth of flooding water was from 0.5 to 1 cm, and two days later, tubers of japanese ribbon wapato (*Sagittaria pygmaea*) were planted. Thereafter, the depth of flooding water was maintained at a level of from 3 to 4 cm, and when barnyargrass and japanese bulrush reached a 0.5 leaf stage and japanese ribbon wapato reached to a primary leaf stage, an aqueous diluted solution of a wettable powder having the compound of the present invention formulated in accordance with a usual formulation method, was uniformly applied under submerged condition by a pipette so that the dose of the active ingredient would be at a predetermined level.

On the other hand, paddy field soil was put into a 1/1,000,000 ha pot and puddled and leveled, and the depth of flooding water was from 3 to 4 cm. One day later, rice (*Oryza sativa* L. var. Nihonbare) of 2 leaf stage was transplanted in a depth of 3 cm. On the 4th day after the transplantation, the compound of the present invention was applied in the same manner as described above.

On the 14th days after the application of the herbicide, the growth of barnyard grass, japanese burlrush and japanese ribbon wapato was visually observed and on the 21st day after the application the herbicide, the growth of rice was visually observed, and the herbicidal effects were evaluated by the growth-controlling degrees (%) ranging from 0 (equivalent to the non-treated area) to 100 (complete kill), whereby the results shown in Table 6 were obtained. Compound Nos. in Table 6 correspond to Compound Nos. in Table 4a and 4b given hereinbefore. The growth controlling degrees against rice of compounds Nos. a-101 et seq (except for a-131, a-132, a-145, a-146 and b-1) are mean values of two test results.

TABLE 6

| Comp. No. | Dose of active ingredient (g/ha) | Growth-controlling degree (%) | | | |
|---|---|---|---|---|---|
| | | EC | SJ | SP | OS |
| a-1 | 1000 | 50 | 100 | 100 | — |
| | 500 | 40 | 100 | — | — |

TABLE 6-continued

| Comp. No. | Dose of active ingredient (g/ha) | Growth-controlling degree (%) | | | |
|---|---|---|---|---|---|
| | | EC | SJ | SP | OS |
| a-2 | 500 | 90 | 95 | 90 | 0 |
| | 250 | 85 | 85 | 85 | 0 |
| a-3 | 1000 | 95 | 100 | 95 | 10 |
| | 500 | 95 | 100 | 85 | 0 |
| a-4 | 500 | 100 | 85 | 85 | 0 |
| | 250 | 100 | 50 | 60 | 0 |
| a-5 | 1000 | 40 | 85 | 85 | 90 |
| | 500 | 0 | 85 | 70 | 30 |
| a-6 | 500 | 100 | 90 | 90 | 50 |
| | 250 | 100 | 85 | 85 | 30 |
| a-7 | 500 | 100 | 100 | 85 | 80 |
| | 250 | 99 | 95 | 85 | 70 |
| a-8 | 1000 | 0 | 85 | 85 | 0 |
| | 500 | 0 | 50 | 85 | 0 |
| a-9 | 500 | 10 | 50 | 70 | 30 |
| a-10 | 500 | 80 | 50 | 85 | 0 |
| | 250 | 60 | 50 | 85 | 0 |
| a-11 | 250 | 100 | 95 | 90 | 100 |
| | 125 | 100 | 90 | 85 | 100 |
| a-12 | 500 | 100 | 100 | 90 | 100 |
| | 250 | 100 | 100 | 90 | 100 |
| a-13 | 500 | 100 | 100 | 90 | 100 |
| | 250 | 100 | 100 | 90 | 100 |
| a-14 | 500 | 40 | 85 | 90 | 10 |
| | 250 | 10 | 85 | 85 | 0 |
| a-15 | 500 | 100 | 85 | 70 | 0 |
| | 250 | 50 | 70 | 70 | 0 |
| a-16 | 500 | 100 | 50 | 30 | 30 |
| | 250 | 99 | 0 | 30 | 0 |
| a-17 | 500 | 100 | 85 | 50 | 20 |
| | 250 | 99 | 50 | 50 | 0 |
| a-18 | 500 | 0 | 90 | 95 | 0 |
| | 250 | 0 | 85 | 95 | 0 |
| a-19 | 500 | 70 | 90 | 90 | 10 |
| | 250 | 40 | 90 | 85 | 0 |
| a-20 | 500 | 90 | 85 | 30 | 60 |
| | 250 | 85 | 50 | 0 | 35 |
| a-21 | 500 | 50 | 95 | 90 | 30 |
| | 250 | 30 | 90 | 50 | 30 |
| a-22 | 500 | 95 | 95 | 90 | 30 |
| | 250 | 100 | 95 | 50 | 20 |
| a-23 | 500 | 100 | 99 | 90 | 0 |
| | 250 | 50 | 99 | 50 | 0 |
| a-24 | 250 | 40 | 85 | 90 | 10 |
| | 125 | 20 | 80 | 85 | 0 |
| a-25 | 250 | 100 | 90 | 90 | 0 |
| | 125 | 85 | 85 | 85 | 0 |
| a-26 | 1000 | 90 | 90 | 10 | 10 |
| | 500 | 50 | 90 | 10 | 0 |

TABLE 6-continued

| Comp. No. | Dose of active ingredient (g/ha) | Growth-controlling degree (%) | | | |
|---|---|---|---|---|---|
| | | EC | SJ | SP | OS |
| a-27 | 250 | 100 | 95 | 90 | 100 |
| | 125 | 100 | 90 | 85 | 40 |
| a-39 | 125 | 100 | 90 | 85 | 35 |
| | 63 | 100 | 85 | 50 | 30 |
| a-40 | 125 | 100 | 100 | 90 | 80 |
| | 63 | 100 | 99 | 90 | 40 |
| a-41 | 125 | 100 | 95 | 85 | 100 |
| | 63 | 100 | 90 | 85 | 70 |
| a-42 | 250 | 100 | 90 | 90 | 90 |
| | 125 | 100 | 90 | 0 | 90 |
| a-43 | 250 | 100 | 90 | 90 | 90 |
| | 125 | 100 | 85 | 50 | 99 |
| a-44 | 250 | 100 | 95 | 90 | 95 |
| | 125 | 100 | 90 | 85 | 80 |
| a-45 | 250 | 100 | 99 | 85 | 100 |
| | 125 | 100 | 90 | 50 | 90 |
| a-47 | 250 | 100 | 100 | 95 | 99 |
| | 125 | 100 | 85 | 60 | 70 |
| a-48 | 250 | 100 | 95 | 90 | 95 |
| | 125 | 99 | 85 | 50 | 50 |
| a-49 | 250 | 100 | 90 | 85 | 100 |
| | 125 | 100 | 90 | 50 | 100 |
| a-51 | 250 | 100 | 99 | 85 | 90 |
| | 125 | 100 | 95 | 10 | 60 |
| a-52 | 250 | 100 | 99 | 30 | 100 |
| | 125 | 100 | 90 | 30 | 95 |
| a-53 | 125 | 100 | 95 | 90 | 80 |
| | 63 | 100 | 90 | 90 | 0 |
| a-55 | 250 | 100 | 95 | 20 | 30 |
| | 125 | 100 | 50 | 0 | 30 |
| a-58 | 250 | 100 | 85 | 50 | 40 |
| | 125 | 99 | 70 | 50 | 40 |
| a-59 | 63 | 100 | 90 | 10 | 30 |
| | 31 | 100 | 50 | — | 30 |
| a-60 | 250 | 100 | 100 | 70 | 95 |
| | 125 | 100 | 95 | 30 | 70 |
| a-69 | 250 | 100 | 99 | 50 | 100 |
| | 125 | 100 | 85 | 50 | 35 |
| a-72 | 125 | 90 | 85 | 20 | 40 |
| | 63 | 60 | 85 | 20 | 35 |
| a-73 | 125 | 100 | 90 | 50 | 80 |
| | 63 | 100 | 70 | 50 | 30 |
| a-76 | 125 | 100 | 90 | 30 | 0 |
| | 63 | 100 | 85 | 0 | 0 |
| a-77 | 125 | 90 | 85 | 50 | 70 |
| | 63 | 70 | 50 | 30 | 40 |
| a-78 | 250 | 100 | 85 | 85 | 80 |
| | 125 | 85 | 60 | 85 | 30 |
| a-79 | 250 | 100 | 95 | 90 | 90 |
| | 125 | 100 | 85 | 50 | 40 |
| a-80 | 500 | 100 | 100 | 95 | 90 |
| | 250 | 99 | 100 | 95 | 90 |
| a-81 | 500 | 95 | 99 | 90 | 30 |
| | 250 | 85 | 90 | 50 | 30 |
| a-82 | 125 | 40 | 85 | 50 | 35 |
| | 63 | 20 | 10 | 0 | 20 |
| a-83 | 250 | 99 | 99 | 90 | 60 |
| | 125 | 95 | 99 | 90 | 40 |
| a-84 | 250 | 100 | 99 | 50 | 90 |
| | 125 | 100 | 95 | 50 | 50 |
| a-85 | 250 | 100 | 85 | 50 | 20 |
| | 125 | 95 | 70 | 0 | 20 |
| a-86 | 125 | 10 | 70 | 10 | 0 |
| | 63 | 10 | 60 | 10 | 0 |
| a-87 | 250 | 100 | 90 | 30 | 40 |
| | 125 | 100 | 85 | 0 | 30 |
| a-88 | 250 | 100 | 90 | 50 | 100 |
| | 125 | 100 | 90 | 20 | 95 |
| a-89 | 250 | 100 | 99 | 90 | 99 |
| | 125 | 99 | 99 | 50 | 95 |
| a-90 | 250 | 99 | 95 | 90 | 80 |
| | 125 | 99 | 90 | 85 | 70 |
| a-91 | 500 | 99 | 99 | 90 | 35 |
| | 250 | 99 | 95 | 85 | 30 |
| a-92 | 250 | 99 | 90 | 10 | 35 |
| | 125 | 85 | 85 | 0 | 10 |
| a-93 | 250 | 100 | 100 | — | 40 |
| | 125 | 100 | 100 | 85 | 0 |
| a-94 | 250 | 100 | 99 | 90 | 99 |
| | 125 | 100 | 95 | 10 | 99 |
| a-95 | 250 | 100 | 100 | — | — |
| | 125 | 100 | 100 | 85 | — |
| a-96 | 250 | 100 | 95 | 85 | 100 |
| | 125 | 100 | 90 | 10 | 99 |
| a-97 | 63 | 95 | 30 | 50 | 50 |
| | 31 | 95 | 0 | 0 | 50 |
| a-98 | 63 | 100 | 80 | 70 | 60 |
| | 31 | 100 | 60 | 0 | 30 |
| a-99 | 125 | 100 | 95 | 50 | 100 |
| | 63 | 100 | — | 50 | 100 |
| a-100 | 125 | 50 | 70 | 10 | 30 |
| | 63 | 10 | 10 | 0 | 0 |
| a-101 | 63 | 100 | 10 | 0 | 40 |
| | 31 | 80 | 0 | 0 | 30 |
| a-102 | 63 | 95 | 85 | 50 | 40 |
| | 31 | 85 | 50 | 0 | 25 |
| a-103 | 63 | 95 | 90 | 50 | 65 |
| | 31 | 85 | 10 | 30 | 10 |
| a-104 | 63 | 99 | 0 | 0 | 30 |
| | 31 | 99 | 0 | 0 | 30 |
| a-105 | 63 | 95 | 0 | 0 | 40 |
| | 31 | 90 | 0 | 0 | 10 |
| a-106 | 250 | 100 | 70 | 70 | 50 |
| | 125 | 99 | 30 | 50 | 15 |
| a-118 | 250 | 100 | 90 | 60 | 95 |
| | 125 | 100 | 70 | 60 | 55 |
| a-120 | 250 | 100 | 99 | 50 | 98 |
| | 125 | 100 | 90 | 40 | 90 |
| a-122 | 250 | 100 | 100 | 70 | 95 |
| | 125 | 100 | 100 | 60 | 100 |
| a-127 | 1000 | 20 | 60 | 70 | — |
| a-131 | 250 | 100 | 90 | — | 80 |
| | 125 | 100 | 85 | 90 | 50 |
| a-132 | 250 | 100 | 85 | — | — |
| | 125 | 100 | 50 | 50 | 30 |
| a-135 | 250 | 100 | 20 | 0 | 10 |
| | 125 | 70 | 0 | 0 | 0 |
| a-138 | 125 | 100 | 20 | 0 | 5 |
| | 63 | 80 | — | 0 | 15 |
| a-139 | 500 | 70 | 60 | 50 | — |
| | 250 | 70 | 20 | 20 | — |
| a-140 | 250 | 100 | 90 | 30 | 98 |
| | 125 | 100 | 90 | — | 35 |
| a-141 | 250 | 100 | 100 | 30 | 100 |
| | 125 | 100 | 100 | 0 | 95 |
| a-143 | 500 | 100 | 10 | 30 | — |
| | 250 | 100 | 0 | 10 | — |
| a-144 | 500 | 99 | 20 | 90 | — |
| | 250 | 70 | 10 | 85 | — |
| a-145 | 250 | 100 | 60 | 50 | 0 |
| | 125 | 100 | 50 | 40 | 10 |
| a-146 | 500 | 90 | 90 | 90 | 30 |
| | 250 | 60 | 70 | 70 | 0 |
| a-148 | 125 | 100 | 70 | 0 | 0 |
| | 63 | 100 | 70 | 0 | 0 |
| a-149 | 125 | 90 | 30 | 0 | 0 |
| | 63 | 85 | 10 | 0 | 0 |
| a-150 | 250 | 100 | 50 | 60 | 0 |
| | 125 | 95 | 0 | 30 | 5 |
| a-151 | 250 | 100 | 0 | 0 | 30 |
| | 125 | 100 | 0 | — | 5 |
| a-152 | 250 | 100 | 60 | 0 | 100 |
| | 125 | 100 | 30 | 0 | 100 |
| a-153 | 250 | 99 | 90 | 70 | 10 |
| | 125 | 100 | 30 | 30 | 20 |
| a-154 | 250 | 100 | 20 | 40 | 60 |

TABLE 6-continued

| Comp. No. | Dose of active ingredient (g/ha) | Growth-controlling degree (%) EC | SJ | SP | OS |
|---|---|---|---|---|---|
| | 125 | 99 | 0 | 0 | 20 |
| a-155 | 250 | 100 | 70 | 0 | 85 |
| | 125 | 100 | 60 | 0 | 50 |
| a-157 | 250 | 90 | 95 | 70 | 0 |
| | 125 | 90 | 0 | 0 | 0 |
| a-158 | 250 | 100 | 80 | 30 | 90 |
| | 125 | 100 | 50 | 60 | 90 |
| a-160 | 250 | 80 | 50 | 0 | 0 |
| | 125 | 70 | — | 0 | 0 |
| a-161 | 250 | 70 | 0 | 0 | 5 |
| | 125 | 70 | 0 | 0 | 0 |
| a-162 | 250 | 100 | 0 | 0 | 10 |
| | 125 | 100 | 0 | 0 | 0 |
| a-164 | 250 | 100 | 0 | 0 | 60 |
| | 125 | 100 | 0 | 0 | 10 |
| a-165 | 125 | 100 | 80 | 30 | 100 |
| | 63 | 95 | 60 | 0 | 35 |
| a-166 | 125 | 100 | 60 | 0 | 100 |
| | 63 | 100 | 20 | 0 | 85 |
| a-167 | 250 | 100 | 95 | 60 | 35 |
| | 125 | 100 | 70 | 0 | 10 |
| a-168 | 125 | 100 | 95 | 0 | 55 |
| | 63 | 100 | 90 | 0 | 50 |
| a-169 | 125 | 100 | 40 | 0 | 90 |
| | 63 | 100 | 40 | 0 | 55 |
| a-170 | 125 | 100 | 30 | 0 | 85 |
| | 63 | 100 | 10 | 0 | 45 |
| a-171 | 250 | 70 | 0 | 0 | 0 |
| a-172 | 250 | 80 | 30 | 50 | 50 |
| a-173 | 250 | 99 | 20 | 0 | 100 |
| | 125 | 70 | — | 0 | 25 |
| a-174 | 250 | 100 | 60 | 0 | 100 |
| | 125 | 100 | 60 | 0 | 100 |
| a-175 | 250 | 80 | 50 | 0 | 0 |
| | 125 | 80 | 30 | 0 | 0 |
| a-177 | 250 | 100 | 50 | 0 | 0 |
| | 125 | 100 | 30 | 0 | 0 |
| a-178 | 250 | 100 | 30 | 0 | 10 |
| | 125 | 100 | 30 | 0 | 0 |
| a-179 | 250 | 100 | 90 | 0 | 100 |
| | 125 | 100 | 30 | 0 | 90 |
| a-180 | 250 | 100 | 30 | 0 | 80 |
| | 125 | 100 | 0 | 0 | 60 |
| a-181 | 250 | 100 | 0 | 20 | 50 |
| a-182 | 250 | 100 | 70 | 0 | 45 |
| | 125 | 100 | 0 | 0 | 15 |
| a-184 | 250 | 85 | 0 | 0 | 0 |
| a-185 | 250 | 70 | 0 | 0 | 0 |
| a-187 | 250 | 70 | 80 | 20 | 15 |
| | 125 | 30 | 80 | 0 | 0 |
| a-188 | 250 | 100 | 50 | 20 | 95 |
| | 125 | 100 | 50 | 0 | 80 |
| a-189 | 250 | 100 | 50 | 20 | 55 |
| | 125 | 100 | 50 | 0 | 50 |
| a-191 | 250 | 100 | 20 | 20 | 35 |
| | 125 | 95 | 0 | 0 | 0 |
| a-194 | 250 | 90 | 30 | 0 | 10 |
| a-200 | 250 | 100 | 90 | 0 | 70 |
| | 125 | 100 | 90 | 0 | 80 |
| a-202 | 250 | 100 | 70 | 0 | 10 |
| | 125 | 85 | 20 | 0 | 10 |
| a-203 | 250 | 100 | 100 | 95 | 100 |
| | 125 | 100 | 95 | 95 | 100 |
| a-204 | 250 | 100 | 30 | 30 | 10 |
| | 125 | 99 | 0 | 0 | 5 |
| a-205 | 250 | 85 | 0 | 0 | 5 |
| a-206 | 250 | 100 | 0 | 60 | 100 |
| | 125 | 95 | 0 | 70 | 90 |
| a-207 | 250 | 95 | 0 | 60 | 50 |
| | 125 | 80 | 0 | 80 | 25 |
| a-208 | 250 | 100 | 30 | 70 | 80 |
| | 125 | 100 | 0 | 60 | 50 |
| a-210 | 250 | 100 | 40 | 70 | 100 |
| | 125 | 100 | 70 | 60 | 85 |
| a-213 | 250 | 100 | 50 | 0 | 95 |
| | 125 | 100 | 20 | 0 | 65 |
| a-214 | 250 | 100 | 60 | 20 | 60 |
| | 125 | 99 | 60 | 0 | 15 |
| a-216 | 250 | 100 | 80 | 0 | 95 |
| | 125 | 100 | 40 | 0 | 15 |
| a-217 | 250 | 100 | 20 | 0 | 100 |
| | 125 | 95 | 0 | 0 | 50 |
| a-218 | 250 | 100 | 70 | 20 | 100 |
| | 125 | 70 | 30 | 0 | 85 |
| a-219 | 250 | 100 | 30 | 0 | 100 |
| | 125 | 100 | 0 | 0 | 70 |
| a-230 | 63 | 100 | 0 | 0 | — |
| | 31 | 100 | 0 | 0 | — |
| a-232 | 63 | 100 | 30 | — | — |
| | 31 | 100 | 0 | 0 | — |
| a-233 | 63 | 70 | 0 | 0 | — |
| | 31 | 50 | 0 | 0 | — |
| a-239 | 63 | 100 | 0 | 0 | 0 |
| | 31 | 80 | 0 | 0 | 0 |
| a-249 | 250 | 100 | 0 | 0 | 95 |
| | 125 | 100 | 0 | 0 | 40 |
| a-250 | 63 | 100 | 40 | 0 | 80 |
| | 31 | 100 | 0 | 0 | 45 |
| a-253 | 63 | 100 | 0 | 0 | 35 |
| | 31 | 100 | 0 | 0 | 30 |
| a-254 | 63 | 100 | 0 | — | 5 |
| | 31 | 100 | 0 | 0 | 0 |
| a-256 | 63 | 100 | 0 | 0 | 0 |
| | 31 | 80 | 0 | 0 | 0 |
| a-257 | 250 | 100 | 20 | 0 | 0 |
| | 125 | 100 | 0 | 0 | 0 |
| a-258 | 250 | 60 | 0 | 20 | 5 |
| | 125 | 70 | 0 | 0 | 0 |
| a-259 | 250 | 100 | 0 | 0 | 10 |
| | 125 | 100 | 0 | 0 | 0 |
| a-260 | 250 | 100 | 0 | 20 | 10 |
| | 125 | 85 | 0 | 0 | 0 |
| a-261 | 250 | 100 | 0 | 40 | 5 |
| | 125 | 70 | 0 | 40 | 0 |
| a-262 | 250 | 100 | 10 | 0 | 10 |
| | 125 | 100 | 0 | 0 | 0 |
| a-263 | 250 | 100 | 0 | 0 | 10 |
| | 125 | 95 | 0 | 0 | 0 |
| a-264 | 250 | 85 | 0 | 0 | 30 |
| | 125 | 70 | 0 | 0 | 15 |
| a-271 | 63 | 100 | 0 | 0 | — |
| | 31 | 95 | 0 | 0 | — |
| b-1 | 250 | 100 | 85 | 50 | 50 |
| | 125 | 100 | 50 | 50 | 20 |

Now, Formulation Examples of the present invention will be given. Compound Nos. in Formulation Examples correspond to Compound Nos. in Table 4a to 4b given hereinbefore.

FORMULATION EXAMPLE 1

| (1) | Compound No. a-12 | 75 parts by weight |
| (2) | Sodium N-methyl-N-oleoyl taurate (Geropon T-77, tradename, manufactured by Rhone-Poulenc) | 14.5 parts by weight |
| (3) | NaCl | 10 parts by weight |
| (4) | Dextrin | 0.5 part by weight |

The above components are placed in a high-speed mixing granulator, admixed with 20 wt % of water, granulated, and dried to form water-dispersible granules.

FORMULATION EXAMPLE 2

| | | |
|---|---|---|
| (1) | Kaolin | 78 parts by weight |
| (2) | Condensate of sodium naphthalene sulfonate and formalin (Laveline FAN, tradename, manufactured by Dai-ichi Kogyo Seiyaku Co., Ltd.) | 2 parts by weight |
| (3) | Sodium polyoxyethylene alkylaryl ether sulfate-premix with white carbon (Sorpol 5039, tradename, manufactured by Toho Chemical Industry Co., Ltd.) | 5 parts by weight |
| (4) | White carbon (Carplex, tradename, manufactured by Shionogi Seiyaku Co., Ltd.) | 15 parts by weight |

The mixture of the above components (1) to (4) and Compound No. a-6 are mixed in a weight ratio of 9:1 to obtain a wettable powder.

FORMULATION EXAMPLE 3

| | | |
|---|---|---|
| (1) | Talc micropowder (Hi-Filler No. 10, tradename, manufactured by Matsumura Sangyo Co., Ltd.) | 33 parts by weight |
| (2) | Dialkyl sulfosuccinate-premixed with white carbon (Sorpol 5050, tradename, manufactured by Toho Chemical Industry Co., Ltd.) | 3 parts by weight |
| (3) | A mixture of polyoxyethylene alkylaryl ether sulfate and a polyoxyethylene monomethyl ether carbonate, premixed with white carbon (Sorpol 5073, tradename, manufactured by Toho Chemical Industry Co., Ltd.) | 4 parts by weight |
| (4) | Compound No. a-42 | 60 parts by weight |

The above components (1) to (4) are mixed to obtain a wettable powder.

FORMULATION EXAMPLE 4

| | | |
|---|---|---|
| (1) | Compound No. a-27 | 4 parts by weight |
| (2) | Bentonite | 30 parts by weight |
| (3) | Calcium carbonate | 61.5 parts by weight |
| (4) | Polycarboxylic acid type surfactant (Toxanon GR-31A, tradename, manufactured by Sanyo Chemical Industries Co., Ltd.) | 3 parts by weight |
| (5) | Calcium lignin sulfonate | 1.5 parts by weight |

Pulverized component (1) and components (2) and (3) are preliminarily mixed, and then components (4) and (5) and water are mixed thereto. The mixture is extruded and granulated, followed by drying-and size-adjusting to obtain granules.

FORMULATION EXAMPLE 5

| | | |
|---|---|---|
| (1) | Compound No. a-22 | 30 parts by weight |
| (2) | A pulverized product of a mixture of kaolinite and sericite (Zieclite, tradename, manufactured by Zieclite Co., Ltd.) | 60 parts by weight |
| (3) | Alkyl naphthalene sulfonate (New Kalgen WG-1, tradename, manufactured by Takemoto Oils and Fats Co., Ltd.) | 5 parts by weight |
| (4) | Polyoxyalkylene allyl phenyl ether sulfate (New Kalgen FS-7, tradename, manufactured by; Takemoto Oils and Fats Co., Ltd.) | 5 parts by weight |

Components (1), (2) and (3) are mixed and passed through a pulverizer, and then component (4) is added thereto. The mixture is kneaded and then extruded and granulated, followed by drying and size-adjusting to obtain water-dispersible granules.

FORMULATION EXAMPLE 6

| | | |
|---|---|---|
| (1) | Compound No. a-13 | 28 parts by weight |
| (2) | Triethanolamine salts of oxyethylated polyarylphenol phosphate (Soprophor FL, tradename, manufactured by Rhone-Poulenc) | 2 parts by weight |
| (3) | A mixture of polyoxyethylene styryl phenyl ether and alkyl aryl sulfonate (Sorpol 355, tradename, manufactured by Toho Chemical Industry Co., Ltd.) | 1 part by weight |
| (4) | Isoparaffin hydrocarbon (IP solvent 1620, tradename, manufactured by Idemitsu Petrochemical Co., Ltd.) | 32 parts by weight |
| (5) | Ethylene glycol | 6 parts by weight |
| (6) | Water | 31 parts by weight |

The above components (1) to (6) are mixed and pulverized by a wet-grinding machine (Dyno-mill) to obtain a water-based suspension concentrate.

We claim:

1. A pyrazole compound of the formula (I) or its salt:

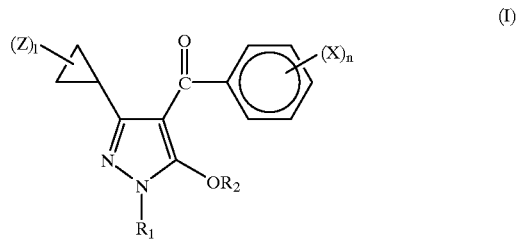

(I)

wherein $R_1$ is an alkyl group, $R_2$ is a hydrogen atom, a methyl group, —A—$R_3$, a phenyl group which may be substituted, a pyridyl group which may be substituted, or an allyl group which is substituted by a phenyl group, A is —$SO_2$—, —CO—, —CH($R_6$)— or —CH($R_7$)CO—, $R_3$ is an alkyl group which may be substituted, an alkenyl group which may be substituted, an alkynyl group which may be substituted, an alkoxy group which may be substituted, a cyano group, a dialkylamino group or a phenyl group which may be substituted, each of $R_6$ and $R_7$ is a hydrogen atom or an alkyl group, X is a hydrogen atom, a halogen atom, an alkyl group, a haloalkyl group, an alkoxy group, an alkylthio group, an alkylsulfinyl group, an alkylsulfonyl group, a nitro group, an alkoxycarbonyl group, —$SO_2N(R_8)R_9$, —N($R_{10}$)$SO_2R_{11}$, —$CH_2S(O)qR_{12}$ or —$OSO_2R_{13}$, each of $R_8$, $R_9$, $R_{10}$, $R_{11}$, $R_{12}$ and $R_{13}$ is an alkyl group, Z is an alkyl group, 1 is an integer of from 0 to 5, n is an integer of from 1 to 5, and q is an integer of from 0 to 2, provided that when 1 is at least 2, a plurality of Z may be the same or different, and when n is at least 2, a plurality of X may be the same or different.

2. The pyrazole compound or its salt according to claim 1, wherein the formula (I) is represented by the formula (I'):

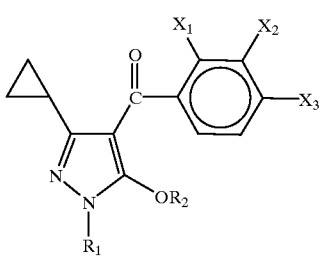

(I')

wherein $R_1$ is an alkyl group, $R_2$ is a hydrogen atom or —A—$R_3$, A is —$SO_2$—, —CO—, —$CH_2$— or —$CH_2CO$—, $R_3$ is an alkyl group which may be substituted, an alkenyl group which may be substituted, an alkynyl group which may be substituted, a cyano group or a phenyl group which may be substituted, each of $X^1$, $X^2$ and $X^3$ is a hydrogen atom, a halogen atom, an alkyl group, a haloalkyl group, an alkoxy group, an alkylthio group, an alkylsulfinyl group, an alkylsulfonyl group, a nitro group, —$SO_2N(R_8)R_9$, —$N(R_{10})SO_2R_{11}$, —$CH_2S(O)qR_{12}$ or —$OSO_2R_{13}$, each of $R_8$, $R_9$, $R_{10}$, $R_{11}$, $R_{12}$ and $R_{13}$ is an alkyl group, and q is an integer of from 0 to 2.

3. The pyrazole compound or its salt according to claim 2, wherein A is —$SO_2$—, —$CH_2$— or —$CH_2CO$—, each of $X^1$, $X^2$ and $X^3$ is a hydrogen atom, a halogen atom, an alkyl group, a haloalkyl group, an alkoxy group, an alkylthio group, an alkylsulfinyl group, an alkylsulfonyl group or a nitro group.

4. The pyrazole compound or its salt according to claim 3, wherein $X^1$ is an alkylthio group, an alkylsulfinyl group or an alkylsulfonyl group, and each of $X^2$ and $X^3$ is a hydrogen atom, a halogen atom, an alkyl group, a haloalkyl group or a nitro group.

5. A process for producing a pyrazole compound of the formula (I-1) or its salt:

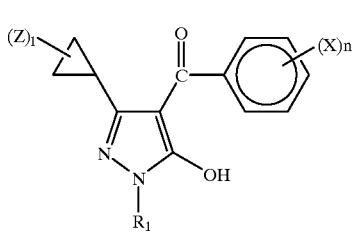

(I-1)

wherein $R_1$ is an alkyl group, Z is an alkyl group, 1 is an integer of from 0 to 5, provided that when 1 is at least 2, a plurality of Z may be the same or different, X is a hydrogen atom, a halogen atom, an alkyl group, a haloalkyl group, an alkoxy group, an alkylthio group, an alkylsulfinyl group, an alkylsulfonyl group, a nitro group, an alkoxycarbonyl group, —$SO_2N(R_8)R_9$, —$N(R_{10})SO_2R_{11}$, —$CH_2S(O)qR_{12}$ or —$OSO_2R_{13}$, each of $R_8$, $R_9$, $R_{10}$, $R_{11}$, $R_{12}$ and $R_{13}$ is an alkyl group, q is an integer of from 0 to 2, and n is an integer of from 1 to 5, provided that when n is at least 2, a plurality of X may be the same or different, which comprises reacting a compound of the formula (II):

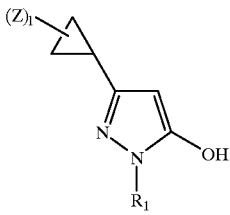

(II)

wherein $R_1$, Z and 1 are as defined above, with a compound of the formula (III):

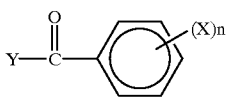

(III)

wherein X and n are as defined above, and Y is a halogen atom, to obtain a compound of the formula (IV):

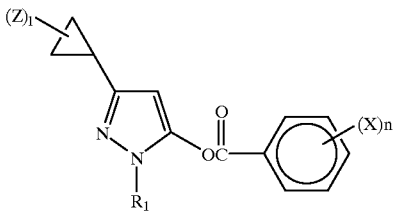

(IV)

wherein $R_1$, X, Z, 1 and n are as defined above, and subjecting the compound of the formula (IV) to a rearrangement reaction.

6. A process for producing a pyrazole compound of the formula (I-1') or its salt:

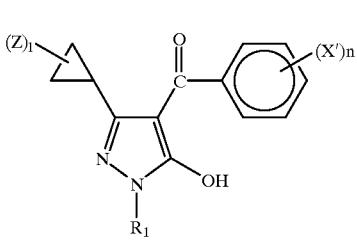

(I-1')

wherein $R_1$ is an alkyl group, Z is an alkyl group, 1 is an integer of from 0 to 5, provided that when 1 is at least 2, a plurality of Z may be the same or different, X' is a hydrogen atom, a halogen atom, an alkyl group, a haloalkyl group, an alkoxy group, an alkylthio group, an alkylsulfinyl group or an alkylsulfonyl group, and n is an integer of from 1 to 5, provided that when n is at least 2, a plurality of X' may be the same or different, which comprises reacting a compound of the formula (II):

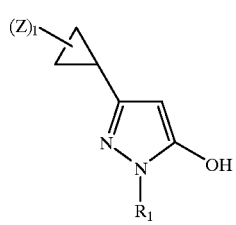

wherein $R_1$, Z and 1 are as defined above, with a compound of the formula (V):

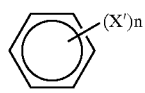

wherein X' and n are as defined above, and carbon tetrachloride, followed by a hydrolytic reaction.

7. A process for producing a pyrazole compound of the formula (I-1) or its salt:

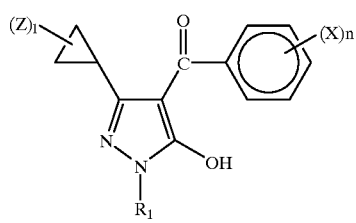

wherein $R_1$ is an alkyl group, Z is an alkyl group, 1 is an integer of from 0 to 5, provided that when 1 is at least 2, a plurality of Z may be the same or different, X is a hydrogen atom, a halogen atom, an alkyl group, a haloalkyl group, an alkoxy group, an alkylthio group, an alkylsulfinyl group, an alkylsulfonyl group, a nitro group, an alkoxycarbonyl group, $-SO_2N(R_8)R_9$, $-N(R_{10})SO_2R_{11}$, $-CH_2S(O)_qR_{12}$ or $-OSO_2R_{13}$, each of $R_8$, $R_9$, $R_{10}$, $R_{11}$, $R_{12}$ and $R_{13}$ is an alkyl group, q is an integer of from 0 to 2, and n is an integer of from 1 to 5, provided that when n is at least 2, a plurality of X may be the same or different, which comprises reacting a compound of the formula (II):

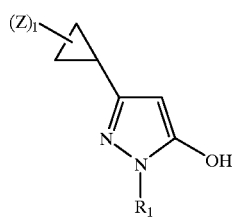

wherein $R_1$, Z and 1 are as defined above, with a compound of the formula (VI):

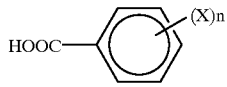

wherein X and n are as defined above.

8. A process for producing a pyrazole compound of the formula (I-1) or its salt:

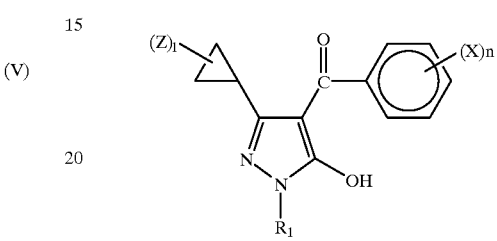

wherein $R_1$ is an alkyl group, Z is an alkyl group, 1 is an integer of from 0 to 5, provided that when 1 is at least 2, a plurality of Z may be the same or different, X is a hydrogen atom, a halogen atom, an alkyl group, a haloalkyl group, an alkoxy group, an alkylthio group, an alkylsulfinyl group, an alkylsulfonyl group, a nitro group, an alkoxycarbonyl group, $-SO_2N(R_8)R_9$, $-N(R_{10})SO_2R_{11}$, $-CH_2S(O)_qR_{12}$ or $-OSO_2R_{13}$, each of $R_8$, $R_9$, $R_{10}$, $R_{11}$, $R_{12}$ and $R_{13}$ is an alkyl group, q is an integer of from 0 to 2, and n is an integer of from 1 to 5, provided that when n is at least 2, a plurality of X may be the same or different, which comprises reacting a compound of the formula (II):

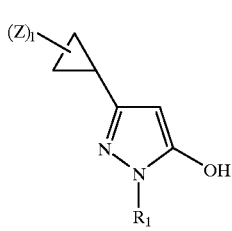

wherein $R_1$, Z and 1 are as defined above, with a compound of the formula (X):

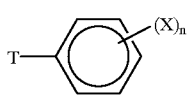

wherein X and n are as defined above, and T is a chlorine atom, a bromine atom or an iodine atom, and carbon monoxide.

9. A process for producing a pyrazole compound of the formula (I-2) or its salt:

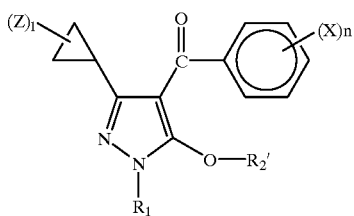

(I-2)

wherein $R_1$ is an alkyl group, $R_2'$ is a methyl group, $-A-R_3$, a phenyl group which may be substituted, a pyridyl group which may be substituted or an allyl group which is substituted by a phenyl group, A is $-SO_2-$, $-CO-$, $-CH(R_6)-$ or $-CH(R_7)CO-$, $R_3$ is an alkyl group which may be substituted, an alkenyl group which may be substituted, an alkynyl group which may be substituted, an alkoxy group which may be substituted, a cyano group, a dialkylamino group or a phenyl group which may be substituted, each of $R_6$ and $R_7$ is a hydrogen atom or an alkyl group, Z is an alkyl group, 1 is an integer of from 0 to 5, provided that when 1 is at least 2, a plurality of Z may be the same or different, X is a hydrogen atom, a halogen atom, an alkyl group, a haloalkyl group, an alkoxy group, an alkylthio group, an alkylsulfinyl group, an alkylsulfonyl group, a nitro group, an alkoxycarbonyl group, $-SO_2N(R_8)R_9$, $-N(R_{10})SO_2R_{11}$, $-CH_2S(O)_qR_{12}$ or $-OSO_2R_{13}$, each of $R_8$, $R_9$, $R_{10}$, $R_{11}$, $R_{12}$ and $R_{13}$ is an alkyl group and n is an integer of from 1 to 5, provided that when n is at least 2, a plurality of X may be the same or different, q is an integer of from 0 to 2, which comprises reacting a compound of the formula (I-1):

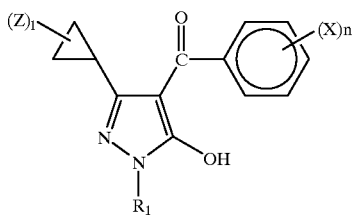

(I-1)

where $R_1$, X, Z, n and 1 are as defined above, with a compound of the formula (VII):

 (VII)

herein $R_2'$ is as defined above, and Y is a halogen atom.

10. A process for producing a pyrazole compound of the formula (I-4) or its salt:

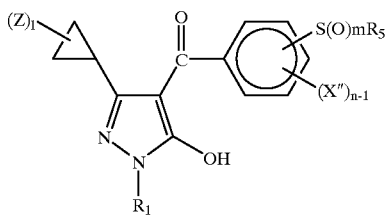

(I-4)

wherein each of $R_1$ and $R_5$ is an alkyl group, Z is an alkyl group, 1 is an integer of from 0 to 5, provided that when 1 is at least 2, a plurality of Z may be the same or different, X" is a hydrogen atom, a halogen atom, an alkyl group, a haloalkyl group, an alkoxy group, an alkylsulfinyl group, an alkylsulfonyl group, a nitro group, an alkoxycarbonyl group, $-SO_2N(R_8)R_9$, $-N(R_{10})SO_2R_{11}$, $-CH_2S(O)_qR_{12}$ or $-OSO_2R_{13}$, each of $R_8$, $R_9$, $R_{10}$, $R_{11}$, $R_{12}$ and $R_{13}$ is an alkyl group, q' is 1 or 2, m is 1 or 2, and n is an integer of from 1 to 5, provided that when n is at least 3, a plurality of X" may be the same or different, which comprises oxidizing a compound of the formula (VI-1):

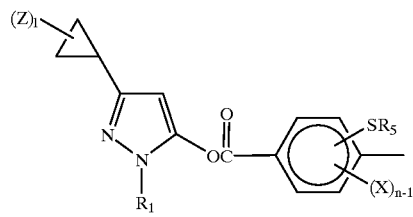

(VI-1)

where $R_1$, $R_5$, Z, 1 and n are as defined above and X is a hydrogen atom, a halogen atom, an alkyl group, a haloalkyl group, an alkoxy group, an alkylthio group, an alkylsulfinyl group, an alkylsulfonyl group, a nitro group, an alkoxycarbonyl group, $-SO_2N(R_8)R_9$, $-N(R_{10})SO_2R_{11}$, $-CH_2S(O)_qR_{12}$ or $-OSO_2R_{13}$, each of $R_8$, $R_9$, $R_{10}$, $R_{11}$, $R_{12}$ and $R_{13}$ is an alkyl group, provided that when n is at least 3, a plurality of X may be the same or different to obtain a compound of the formula (VI-2):

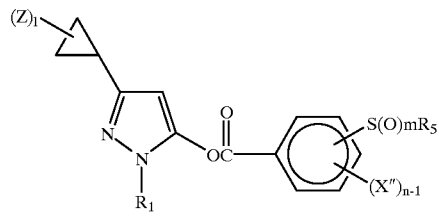

(VI-2)

wherein $R_1$, $R_5$, Z, X", 1, m and n are as defined above, and subjecting the compound of the formula (VI-2) to a rearrangement reaction.

11. A process for producing a pyrazole compound of the formula (I-7) or its salt:

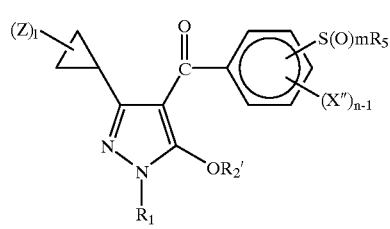

(I-7)

wherein each of $R_1$ and $R_5$ is an alkyl group, $R_2'$ is a methyl group, $-A-R_3$, a phenyl group which may be substituted, a pyridyl group which may be substituted or an allyl group which is substituted by a phenyl group, A is $-SO_2-$, $-CO-$, $-CH(R_6)-$ or $-CH(R_7)CO-$, $R_3$ is an alkyl group which may be substituted, an alkenyl group which may be substituted, an alkynyl group which may be substituted, an alkoxy group which may be substituted, a cyano group, a dialkylamino group or a phenyl group which may be substituted, each of $R_6$ and $R_7$ is a hydrogen atom or an alkyl group, Z is an alkyl group, 1 is an integer of from 0 to 5, provided that when 1 is at least 2, a plurality of Z may be the same or different, m is 1 or 2, X" is a hydrogen atom, a halogen atom, an alkyl group, a haloalkyl group, an alkoxy group, an alkylsulfinyl group, an alkylsulfonyl group, a nitro group, an alkoxycarbonyl group, —$SO_2N(R_8)R_9$, —$N(R_{10})SO_2R_{11}$, —$CH_2S(O)_{q'}R_{12}$ or —$OSO_2R_{13}$, each of $R_8$, $R_9$, $R_{10}$, $R_{11}$, $R_{12}$ and $R_{13}$ is an alkyl group, q' is 1 or 2, and n is an integer of from 1 to 5, provided that when n is at least 3, a plurality of X" may be the same or different, which comprises oxidizing a compound of the formula (I-6):

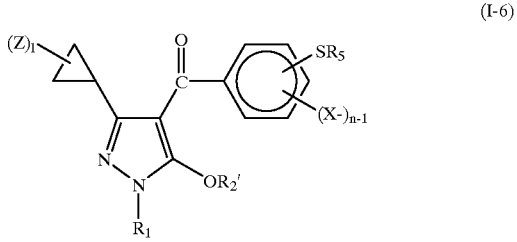

(I-6)

where $R_1$, $R_2'$, $R_5$, Z, 1 and n are as defined above, and X is a hydrogen atom, a halogen atom, an alkyl group, a haloalkyl group, an alkoxy group, an alkylthio group, an alkylsulfinyl group, an alkylsulfonyl group, a nitro group, an alkoxycarbonyl group, —$SO_2N(R_8)R_9$, —$N(R_{10})SO_2R_{11}$, —$CH_2S(O)_qR_{12}$ or —$OSO_2R_{13}$, each of $R_8$, $R_9$, $R_{10}$, $R_{11}$, $R_{12}$ and $R_{13}$ is an alkyl group, q is an integer of from 0 to 2, provided that when n is at least 3, a plurality of X may be the same or different.

12. A herbicide containing the pyrazole compound or its salt as defined in claim 1, as an active ingredient.

13. A method for controlling noxious weeds, which comprises applying an effective amount of the pyrazole compound or its salt as defined in claim 1.

14. A method for controlling noxious weeds, which comprises applying an effective amount of the pyrazole compound or its salt as defined in claim 1 to an upland field.

15. A method for controlling noxious weeds, which comprises applying an effective amount of the pyrazole compound or its salt as defined in claim 1 to a corn field.

16. A method for controlling noxious weeds, which comprises applying an effective amount of the pyrazole compound or its salt as defined in claim 1 to a wheat field.

17. A method for controlling noxious weeds, which comprises applying an effective amount of the pyrazole compound or its salt as defined in claim 1 to a paddy field.

18. A mixed herbicidal composition comprising at least one member selected from the pyrazole compound or its salt as defined in claim 1 and at least one member selected from active ingredient compounds of other herbicides.

* * * * *